US011414643B2

(12) United States Patent
Del Chase et al.

(10) Patent No.: US 11,414,643 B2
(45) Date of Patent: Aug. 16, 2022

(54) **MUTANT AND GENETICALLY MODIFIED *BACILLUS* CELLS AND METHODS THEREOF FOR INCREASED PROTEIN PRODUCTION**

(71) Applicant: DANISCO US INC., Palo Alto, CA (US)

(72) Inventors: Shannon Del Chase, Palo Alto, CA (US); Carol Marie Fioresi, Redwood City, CA (US); Ryan L. Frisch, Newark, DE (US); Helen Olivia Masson, Palo Alto, CA (US); Anita Van Kimmenade, Woodside, CA (US)

(73) Assignee: DANISCO US INC., Palo Alto, CA (US)

( * ) Notice: Subject to any disclaimer, the term of this patent is extended or adjusted under 35 U.S.C. 154(b) by 0 days.

(21) Appl. No.: 16/957,217

(22) PCT Filed: Dec. 12, 2018

(86) PCT No.: PCT/US2018/065150

§ 371 (c)(1),
(2) Date: Jun. 23, 2020

(87) PCT Pub. No.: WO2019/135868

PCT Pub. Date: Jul. 11, 2019

(65) Prior Publication Data

US 2020/0392451 A1 Dec. 17, 2020

Related U.S. Application Data

(60) Provisional application No. 62/613,339, filed on Jan. 3, 2018.

(51) Int. Cl.

| | |
|---|---|
| ***C12N 1/20*** | (2006.01) |
| ***C07K 14/32*** | (2006.01) |
| ***C12N 15/75*** | (2006.01) |
| ***C12P 21/02*** | (2006.01) |

(52) U.S. Cl.

CPC ................ *C12N 1/20* (2013.01); *C07K 14/32* (2013.01); *C12N 15/75* (2013.01); *C12P 21/02* (2013.01)

(58) Field of Classification Search

CPC .......... C12N 1/20; C12N 15/75; C07K 14/32; C07K 14/47; C12P 21/02

See application file for complete search history.

(56) References Cited

U.S. PATENT DOCUMENTS 6,518,052 B1 * 2/2003 Weinmann .............. C12N 9/90 435/183

FOREIGN PATENT DOCUMENTS

| | | | |
|---|---|---|---|
| EP | 2216640 | A1 | 8/2010 |
| WO | 03087148 | A2 | 10/2003 |
| WO | 2008066931 | | 6/2008 |
| WO | 2016099917 | A1 | 6/2016 |
| WO | 2017112733 | A1 | 6/2017 |
| WO | 2018156705 | A1 | 8/2018 |
| WO | 2019135868 | A1 | 7/2019 |

OTHER PUBLICATIONS

Schmalisch et al. Control of the Bacillus subtilis antiterminator protein GlcT by phosphorylation: Elucidation of the phosphorylation chain leading to inactivation of GlcT. JBC 278(51): 51108-51115, 2003.*

Kunst et al. The complete genome sequence of the Gram-positive bacterium *Bacillus subtilis*. Nature (1997), 390: 249-256.*

International Search Report and Written Opinion from PCT App. No. PCT/US2018/065150 dated Mar. 6, 2019, 15 pages.

International Preliminary Report on Patentability from PCT App. No. PCT/US2018/065150 dated Jul. 7, 2020, 9 pages.

Bachem et al., "Regulation of the Bacillus subtilis GlcT Antiterminator Protein by Components of the Phosphotransferase System", Oct. 15, 1998, p. 5319-5326.

Goodson et al., "LoaP is a broadly conserved antiterminator protein that regulates antibiotic gene clusters in Bacillus amyloliquefaciens", Nature Microbiology,vol. 2, No. 5, Feb. 13, 2017, 23 pages.

Himmel et al., "Structure of the RBD-PRDI fragment of the antiterminator protein GlcT", Acta Crystallographica Section F Structural Biology and Crystallization Communications,vol. 68, No. 7, Jul. 1, 2012, p. 751-756.

Muth et al., "Genetic evidence for a novel competence inhibitor in the industrially important Bacillus licheniformis", AMB Express,vol. 7, No. 1, Jul. 11, 2017, 8 pages.

Postma et al., "Phosphoenolpyruvate: Carbohydrate Phosphotransferase Systems of Bacteria", Microbiological Reviews, Sep. 1993, pp. 543-594.

Schmalisch et al., "Control of the Bacillus subtilis Antiterminator Protein GlcT by Phosphorylation : Elucidation of the Phosphorylation Chain Leading to Inactivation of GlcT", Journal of Biological Chemistry,vol. 278, No. 51, Oct. 3, 2003, pp. 51108-51115.

Stulke et al., "Regulation of carbon catabolism in *Bacillus* species", Annu Rev. Microbiol., 54, 2000, pp. 849-880.

Voigt et al., "High-resolution proteome maps of Bacillus licheniformis cells growing in minimal medium", Proteomics,vol. 15, No. 15, Aug. 1, 2015, p. 2629-2633.

(Continued)

*Primary Examiner* — Iqbal H Chowdhury

(57) ABSTRACT

The instant disclosure is generally related to novel *Bacillus* sp. mutants capable of producing increased amounts of industrially relevant proteins of interest. Certain embodiments of the disclosure are related to modified *Bacillus* sp. cells comprising an introduced polynucleotide encoding a variant GlcT protein. Other embodiments are related to methods and compositions for producing endogenous and/or heterologous proteins of interest in the modified *Bacillus* sp. (daughter) cells, whereas certain other embodiments are directed to nucleic acid sequences, particularly polynucleotide open reading frame (ORF) sequences, vectors thereof and DNA expression constructs thereof, encoding variant GlcT proteins of the disclosure.

22 Claims, 4 Drawing Sheets

Specification includes a Sequence Listing.

(56) References Cited

OTHER PUBLICATIONS

Naschkau et al, "Generation of readily transformable Bacillus licheniformis mutants", Applied Microbiology and Biotechnology, vol. 78, No. 1, Nov. 29, 2007, pp. 181-188.

* cited by examiner

```
            1        10        20        30        40        50        60        70        80
glcT        GTGAACAGATCCTTTACCGTTGAAAAGGTACTCAACAACAACGTTTTAATCGCTCTCCATGATGATTACAGAGAAGTTGTCTTGATT
glcT C199T  GTGAACAGATCCTTTACCGTTGAAAAGGTACTCAACAACAACGTTTTAATCGCTCTCCATGATGATTACAGAGAAGTTGTCTTGATT
              90       100       110       120       130       140       150       160       170
glcT        GGCAAAGGAATCGGTTTTGGTAAAAAGCGCGGAGATCTTATCGAACATGAGAACTACGAAAAAATGTTTATCCTGGAAAATGATAAG
glcT C199T  GGCAAAGGAATCGGTTTTGGTAAAAAGCGCGGAGATCTTATCGAACATGAGAACTACGAAAAAATGTTTATCCTGGAAAATGATAAG
                 180       190       200       210       220       230       240       250       260
glcT        GAACAATCGCAGTATAAGAAGCTCCTCACTTATGTCGATGAAAAAATGGTTGATATCGCCAATGATGTCATCTACCATATCGCGCAA
glcT C199T  GAACAATCGCAGTATAAGAAGCTCTTCACTTATGTCGATGAAAAAATGGTTGATATCGCCAATGATGTCATCTACCATATCGCGCAA
                    270       280       290       300       310       320       330       340
glcT        AAAATCGGCCAGCCGCTGAACGAACACATTCATGTCGCCCTGACGGACCATATCGCATTTGCAGTTAAGCGTCTAGAAAAGGGATTT
glcT C199T  AAAATCGGCCAGCCGCTGAACGAACACATTCATGTCGCCCTGACGGACCATATCGCATTTGCAGTTAAGCGTCTAGAAAAGGGATTT
             350       360       370       380       390       400       410       420       430
glcT        GATATGAAAAATCCGTTTTTGCTTGAGACGGAATCGCTTTATCCGAAGGAATACGAAGTCGCCAAGGAAGCCGTCGATATGATTAAT
glcT C199T  GATATGAAAAATCCGTTTTTGCTTGAGACGGAATCGCTTTATCCGAAGGAATACGAAGTCGCCAAGGAAGCCGTCGATATGATTAAT
                440       450       460       470       480       490       500       510       520
glcT        GAAAAATCCGACATTCAGCTGCCTGAAGGTGAAATCGGGTTCATCGCGCTTCATATCCACAGTGCGATGACAAACCGCCCGCTTTCT
glcT C199T  GAAAAATCCGACATTCAGCTGCCTGAAGGTGAAATCGGGTTCATCGCGCTTCATATCCACAGTGCGATGACAAACCGCCCGCTTTCT
                   530       540       550       560       570       580       590       600
glcT        GAAGTCAATCAGCATTCACAACTGATCTCCAGGCTTGTCCAGGTCATCGAAGATTCATTCCAGATGCAAGTCAACAGGGAAAGCGTG
glcT C199T  GAAGTCAATCAGCATTCACAACTGATCTCCAGGCTTGTCCAGGTCATCGAAGATTCATTCCAGATGCAAGTCAACAGGGAAAGCGTG
           610       620       630       640       650       660       670       680       690
glcT        AACTATTTGCGGCTGATCAGGCACTTGCGCTTTACGATTGACAGGATAAAACGGGACGAGCCGATTCAGGAACCGGAAAAATTAATG
glcT C199T  AACTATTTGCGGCTGATCAGGCACTTGCGCTTTACGATTGACAGGATAAAACGGGACGAGCCGATTCAGGAACCGGAAAAATTAATG
              700       710       720       730       740       750       760       770       780
glcT        TTGTTGTTGAAAACGGAATATCCGCTGTGTTACAATACTGCTTGGAAGATGATCAAGATCTTGCAGCAAGCGCTCAAGAAACCGGTT
glcT C199T  TTGTTGTTGAAAACGGAATATCCGCTGTGTTACAATACTGCTTGGAAGATGATCAAGATCTTGCAGCAAGCGCTCAAGAAACCGGTT
                 790       800       810       820       830       840    846
glcT        CATGAGGCAGAAGCCGTTTATTTGACATTGCATTTGTACCGTTTGACTAATAAAATTTCATAA
glcT C199T  CATGAGGCAGAAGCCGTTTATTTGACATTGCATTTGTACCGTTTGACTAATAAAATTTCATAA
```

*FIG. 1A*

```
            1       10        20        30        40        50        60
            |        |         |         |         |         |         |
glcT        VNRSFTVEKVLNNNVLIALHDDYREVVLIGKGIGFGKKRGDLIEHENYEKMFILENDKEQ
glcT L67F   VNRSFTVEKVLNNNVLIALHDDYREVVLIGKGIGFGKKRGDLIEHENYEKMFILENDKEQ

                    70        80        90       100       110       120
                     |         |         |         |         |         |
glcT        SQYKKLLTYVDEKMVDIANDVIYHIAQKIGQPLNEHIHVALTDHIAFAVKRLEKGFDMKN
glcT L67F   SQYKKLFTYVDEKMVDIANDVIYHIAQKIGQPLNEHIHVALTDHIAFAVKRLEKGFDMKN

                   130       140       150       160       170       180
                     |         |         |         |         |         |
glcT        PFLLETESLYPKEYEVAKEAVDMINEKSDIQLPEGEIGFIALHIHSAMTNRPLSEVNQHS
glcT L67F   PFLLETESLYPKEYEVAKEAVDMINEKSDIQLPEGEIGFIALHIHSAMTNRPLSEVNQHS

                   190       200       210       220       230       240
                     |         |         |         |         |         |
glcT        QLISRLVQVIEDSFQMQVNRESVNYLRLIRHLRFTIDRIKRDEPIQEPEKLMLLLKTEYP
glcT L67F   QLISRLVQVIEDSFQMQVNRESVNYLRLIRHLRFTIDRIKRDEPIQEPEKLMLLLKTEYP

                   250       260       270        281
                     |         |         |          |
glcT        LCYNTAWKMIKILQQALKKPVHEAEAVYLTLHLYRLTNKIS
glcT L67F   LCYNTAWKMIKILQQALKKPVHEAEAVYLTLHLYRLTNKIS
```

*FIG. 1B*

MUTANT AND GENETICALLY MODIFIED *BACILLUS* CELLS AND METHODS THEREOF FOR INCREASED PROTEIN PRODUCTION

CROSS REFERENCE TO RELATED APPLICATIONS

This application claims benefit to U.S. Provisional Application No. 62/613,339, filed Jan. 3, 2018, which is hereby incorporated by referenced in its entirety.

FIELD

The present disclosure is generally related to the fields of bacteriology, microbiology, genetics, molecular biology, enzymology, industrial protein production and the like. More particularly, certain embodiments of the disclosure are related to novel *Bacillus* sp. mutants capable of producing increased amounts of industrially relevant proteins of interest. Other embodiments of the disclosure are related to modified *Bacillus* sp. cells comprising an introduced polynucleotide encoding a variant GlcT protein. Other embodiments are related to methods and compositions for producing endogenous and/or heterologous proteins of interest in the modified *Bacillus* sp. (daughter) cells, whereas certain other embodiments are directed to nucleic acid sequences, particularly polynucleotide open reading frame (ORF) sequences, vectors thereof and DNA expression constructs thereof, encoding variant GlcT proteins of the disclosure.

REFERENCE TO A SEQUENCE LISTING

The contents of the electronic submission of the text file Sequence Listing, named "NB41301_WO_PCT_SEQ.txt" was created on Dec. 11, 2018 and is 137 KB in size, which is hereby incorporated by reference in its entirety.

BACKGROUND

Gram-positive bacteria such as *Bacillus subtilis, Bacillus licheniformis, Bacillus amyloliquefaciens* and the like are frequently used as microbial factories for the production of industrial relevant proteins, due to their excellent fermentation properties and high yields (e.g., up to 25 grams per liter culture; Van Dijl and Hecker, 2013). For example, *B. subtilis* is well known for its production of α-amylases (Jensen et al., 2000; Raul et al., 2014) and proteases (Brode et al., 1996) necessary for food, textile, laundry, medical instrument cleaning, pharmaceutical industries and the like (Westers et al., 2004). Because these non-pathogenic Gram-positive bacteria produce proteins that completely lack toxic by-products (e.g., lipopolysaccharides; LPS, also known as endotoxins) they have obtained the "Qualified Presumption of Safety" (QPS) status of the European Food Safety Authority, and many of their products gained a "Generally Recognized as Safe" (GRAS) status from the US Food and Drug Administration (Olempska-Beer et al., 2006; Earl et al., 2008; Caspers et al., 2010).

Thus, the production of proteins (e.g., enzymes, antibodies, receptors, etc.) in microbial host cells is of particular interest in the biotechnological arts. Likewise, the optimization of *Bacillus* host cells for the production and secretion of one or more protein(s) of interest is of high relevance, particularly in the industrial biotechnology setting, wherein small improvements in protein yield are quite significant when the protein is produced in large industrial quantities.

More particularly, *B. licheniformis* and *B. subtilis* are exemplary *Bacillus* sp. host cells of high industrial importance, and as such, the ability to genetically modify and engineer *Bacillus* sp. host cells for enhanced/increased protein expression/production is highly desirable for construction of new and improved *Bacillus* sp. production strains. Thus, the disclosure set forth herein is related to the highly desirable and unmet needs of obtaining and constructing *Bacillus* host cells (e.g., protein production host cells, cell factories) having increased protein production capabilities, increased secondary metabolite production, and the like.

SUMMARY

The instant disclosure is generally related to compositions and methods for producing and constructing *Bacillus* sp. (host) cells (e.g., protein production host cells, cell factories) having increased protein production capabilities, increased secondary metabolite production capabilities and the like.

More particularly, certain embodiments of the disclosure are related to a mutant of a parental *Bacillus licheniformis* cell comprising a glcT gene encoding a variant GlcT protein comprising a phenylalanine (F) at amino acid position 67 (F67) of SEQ ID NO: 55. In certain embodiments, the gene encoding the variant GlcT protein of SEQ ID NO: 55 comprises a nucleic acid sequence comprising at least 90% sequence identity to SEQ ID NO 22, SEQ ID NO: 81 or SEQ ID NO: 56. In other embodiments, the mutant *B. licheniformis* cell further comprises a restored rghR2 gene ($rghR2_{rest}$) encoding a RghR2 protein of SEQ ID NO: 84. In other embodiments, the mutant cell comprises an introduced polynucleotide encoding a protein of interest (POI). In certain embodiments, the POI is an amylase or a protease. In other embodiments, the introduced polynucleotide encoding the POI comprises a mod-5'-UTR sequence of SEQ ID NO: 63 operably linked and upstream (5') of the polynucleotide encoding the POI.

In other embodiments, the disclosure is related to a genetically modified *Bacillus* cell derived from a parental *Bacillus* cell comprising a wild-type glcT gene encoding a wild-type GlcT protein of SEQ ID NO: 82, wherein the modified *Bacillus* cell comprises a modified glcT gene encoding a GlcT protein comprising at least 90% sequence identity to SEQ ID NO: 55 and comprising a phenylalanine (F) at position 67 of SEQ ID NO: 55. In certain embodiments, the wild-type glcT gene encoding the wild-type GlcT protein of SEQ ID NO: 82 in the parental cell is modified with a glcT-Cas9 targeting vector, wherein the glcT-Cas9 targeting vector modifies codon 67 of the wild-type glcT gene, wherein modified glcT gene encodes a GlcT protein comprising at least 90% sequence identity to SEQ ID NO: 55 and comprising a phenylalanine (F) at position 67 of SEQ ID NO: 55.

Thus, in other embodiments, the disclosure is related to a genetically modified *Bacillus* cell comprising an introduced polynucleotide encoding a variant GlcT protein comprising at least 90% sequence identity to SEQ ID NO: 55 and comprising a phenylalanine (F) at amino acid position 67 (F67) of SEQ ID NO: 55. In certain embodiments, The modified cell further comprises an inactivated endogenous chromosomal glcT gene encoding a GlcT protein comprising at least 90% sequence identity to SEQ ID NO: 82 and comprising a leucine (L) at amino acid position 67 (L67) of SEQ ID NO: 82. In other embodiments, the modified *Bacillus* cell is a *Bacillus licheniformis* cell, wherein the modified *B. licheniformis* further comprises a restored rghR2 gene ($rghR2_{rest}$) encoding a RghR2 protein of SEQ ID NO: 84. In related embodiments, the modified cell of the disclosure comprises an introduced polynucleotide encoding a heterologous POI. In certain embodiments, the POI is an amylase or a protease. In another embodiment, the introduced polynucleotide integrates into a targeted *Bacillus* cell chromosomal gene locus. In certain other embodiments, the introduced polynucleotide encoding the POI comprises a mod-5'-UTR sequence of SEQ ID NO: 63 operably linked and upstream (5') of the polynucleotide sequence encoding the POI.

In other embodiments, the disclosure is related to a modified *Bacillus* cell derived from a parental *Bacillus* cell comprising a glcT gene encoding a wild-type GlcT protein comprising a leucine (L) at amino acid position 67 (L67) of SEQ ID NO: 82, wherein the modified *Bacillus* cell comprises a modified glcT gene encoding a variant GlcT protein comprising a phenylalanine (F) at amino acid position 67 (F67) of SEQ ID NO: 55, wherein the modified *Bacillus* cell produces an increased amount of a protein of interest (POI) relative to the parental cell producing the same POI. Thus, in certain embodiments, the modified cell comprises an introduced DNA construct encoding a heterologous POI, wherein the modified *Bacillus* cell produces an increased amount of the heterologous POI relative to the parental cell producing the same heterologous POI. In other embodiments, the modified cell further comprises a restored rghR2 gene encoding a RghR2 protein of SEQ ID NO: 84. In certain embodiments, the POI is an amylase or a protease. In certain other embodiments, the introduced DNA construct encoding the POI comprises a modified 5'-UTR sequence of SEQ ID NO: 63 operably linked upstream (5') of the DNA construct.

In other embodiments, the disclosure is related to an isolated polynucleotide open reading frame (ORF) encoding a variant *Bacillus* sp. GlcT (anti-termination) protein, the variant GlcT protein comprising a leucine (L) to phenylalanine (F) substitution at amino acid position 67 (L67F) of SEQ ID NO: 55. In certain embodiments, the variant protein comprises 95% or greater sequence identity to SEQ ID NO: 55 and comprises a phenylalanine (F) at amino acid position 67 (F67) of SEQ ID NO: 55. In other embodiments, the ORF comprises a nucleic acid sequence having at least 95% sequence identity to SEQ ID NO: 56.

Thus, certain embodiments are related to a vector comprising a polynucleotide encoding a variant GlcT protein of SEQ ID NO: 55. In other embodiments, the vector comprises an upstream (5') homology region (5'-HR) operably linked (5') to the ORF sequence and/or a downstream (3') homology region (3'-HR) operably linked (3') to the ORF sequence, wherein the 5'-HR and/or the 3'-HR comprise(s) sufficient homology with a targeted genomic locus of a *Bacillus* sp. host cell to effect integration of the vector into the targeted genomic locus by homologous recombination, when the vector is transformed into a competent *Bacillus* sp. host cell.

In other embodiments, the disclosure is related to an expression construct comprising a polynucleotide ORF encoding a variant GlcT protein of SEQ ID NO: 55. In certain embodiments, the construct comprises a promoter nucleic acid sequence functional in *Bacillus* sp. cells, wherein the promoter sequence is operably linked and upstream (5') of the ORF sequence. In other embodiments, the construct further comprises a modified *B. subtilis* aprE 5'-untranslated region sequence (5'-UTR) of SEQ ID NO: 63, wherein the modified 5'-UTR is downstream (3') and operably linked to the promoter sequence and upstream (5') and operably linked to the ORF sequence. In certain other embodiments, the construct further comprises a terminator sequence downstream (3') and operably linked to the ORF sequence.

In other embodiments, the disclosure is related to a method for producing increased amounts of a protein of interest (POI) in a mutant of a parental *Bacillus licheniformis* cell comprising (a) obtaining a mutant of a parental *B. licheniformis* cell comprising a glcT gene encoding a GlcT protein comprising a phenylalanine (F) at amino acid position 67 (F67) of SEQ ID NO: 55 and introducing into the mutant cell a polynucleotide construct encoding a heterologous POI, (b) cultivating the mutant cell of step (a) in a medium suitable for the production of a POI, and (c) recovering the POI from the cultivation medium, wherein the mutant *B. licheniformis* cell produces an increased amount of the POI relative to the parental *B. licheniformis* cell producing the same POI, when cultivated under the same conditions.

Other embodiments are related to a method for producing increased amounts of a protein of interest (POI) in a modified *Bacillus* cell derived from an unmodified *Bacillus* parental cell comprising (a) obtaining a parental *Bacillus* cell comprising an endogenous chromosomal glcT gene encoding a wild-type GlcT protein comprising a leucine (L) at amino acid position 67 (L67) of SEQ ID NO: 82 and modifying the parental cell by introducing (i) a polynucleotide encoding a variant GlcT protein comprising at least 90% sequence identity to SEQ ID NO: 55 and comprising a phenylalanine (F) at amino acid position 67 (F67) of SEQ ID NO: 55 and (ii) a polynucleotide encoding a POI, (b) cultivating the modified cell of step (a) in a medium suitable for the production of a POI, and (c) recovering the POI from the cultivation medium, wherein the modified *Bacillus* cell produces an increased amount of the POI relative to the parental cell producing the same POI when cultivated under the same conditions. In certain other embodiments, the introduced polynucleotide encoding the GlcT variant protein integrates into the chromosomal glcT gene locus by homologous recombination, thereby replacing and eliminating the endogenous chromosomal glcT gene encoding the GlcT protein of SEQ ID NO: 82.

In another embodiment, the disclosure is related to a method for producing increased amounts of a protein of interest (POI) in a modified *Bacillus* cell derived from an unmodified *Bacillus* parental cell comprising (a) obtaining a parental *Bacillus* cell comprising an endogenous chromosomal glcT gene encoding a wild-type GlcT protein comprising a leucine (L) at amino acid position 67 (L67) of SEQ ID NO: 82, (b) modifying the parental cell of step (a) with a glcT-Cas9 targeting vector, wherein the glcT-Cas9 targeting vector modifies codon 67 of the wild-type glcT gene, wherein modified glcT gene encodes a GlcT protein comprising at least 90% sequence identity to SEQ ID NO: 55 and comprising a phenylalanine (F) at position 67 of SEQ ID NO: 55, (c) cultivating the modified cell of step (b) in a medium suitable for the production of a POI, and (c) recovering the POI from the cultivation medium, wherein the modified *Bacillus* cell produces an increased amount of the POI relative to the parental cell producing the same POI when cultivated under the same conditions. In certain embodiments, n the POI is an endogenous POI or a heterologous POI. In particular embodiments, the POI is a heterologous POI.

BRIEF DESCRIPTION OF DRAWINGS

FIG. 1 presents a nucleic acid sequence alignment (FIG. 1A) and an amino acid sequence alignment (FIG. 1B) of glcT wild-type (SEQ ID NO: 22) and glcT mutant (SEQ ID NO: 56) nucleic acid sequences, encoding GlcT wild-type (SEQ ID NO: 82) and GlcT variant (SEQ ID NO: 55) protein sequences, respectively. More particularly, FIG. 1A shows a nucleic acid sequence alignment of a *B. licheniformis* ORF (SEQ ID NO: 22) encoding a wild-type GlcT protein (SEQ ID NO: 82) relative to a mutant *B. licheniformis* ORF (SEQ ID NO: 56) encoding a variant GlcT protein (SEQ ID NO: 55). For example, as shown in FIG. 1A, the two aligned ORF sequences (SEQ ID NO: 22 vs. SEQ ID NO: 56) differ by a single nucleotide polymorphism (SNP) at nucleotide position 199, wherein position 199 of SEQ ID NO: 22 comprises a cytosine (C) and position 199 of SEQ ID NO: 56 comprises a thymine (T); e.g., see FIG. 1A black boxed nucleotides (C) and (T) at position 199). Similarly, FIG. 1B shows an alignment of the encoded wild-type GlcT protein (SEQ ID NO: 82) and the encoded variant GlcT protein (SEQ ID NO: 55), wherein the (C) to (T) SNP at position 199 of SEQ ID NO: 56 (see, FIG. 1A), results in a leucine (L) to phenylalanine (F) substitution at amino acid residue position 67 of SEQ ID NO: 55 (e.g., see FIG. 1B, black boxed (L) and (F) amino acids at residue position 67 of SEQ ID NO: 22 and SEQ ID NO: 55, respectively).

BRIEF DESCRIPTION OF THE BIOLOGICAL SEQUENCES

Figure 2A:
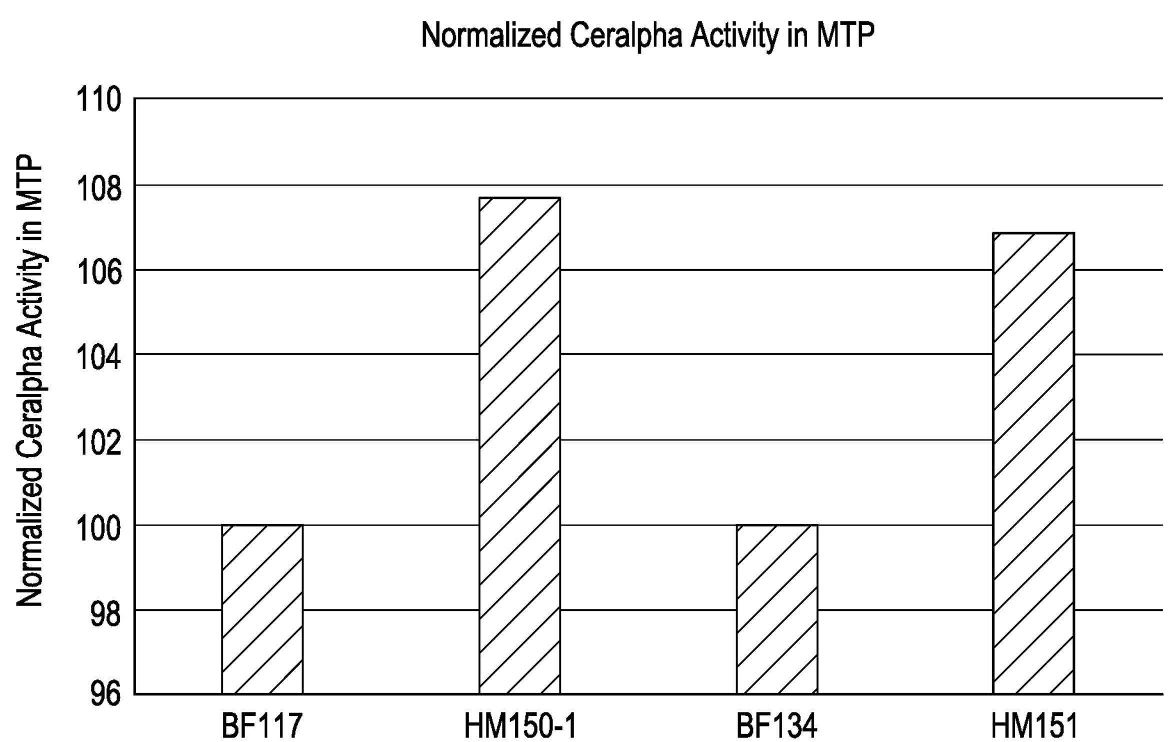
FIG. 2 shows normalized α-amylase Ceralpha activity (FIG. 2A) and α-amylase specific productivity (FIG. 2B) in microtiter plates, wherein *Bacillus* host cells BF117 (WT glcT+mod-5'-UTR), BF134 (WT glcT+WT-5'-UTR), HM150-1 (variant glcT1+mod-5'-UTR) and HM151 (variant glcT1+WT-5'-UTR) were screened. As presented in FIG. 2B, the normalized α-amylase Qp of host cell HM151 (variant glcT1+WT-5'-UTR) is approximately 4-5% increased relative to the α-amylase Qp of either host cell BF134 (WT glcT+WT-5'-UTR) or BF117 (WT glcT+mod-5'-UTR). Furthermore, as presented in FIG. 2B, the α-amylase Qp of *Bacillus* host cell HM150-1 (variant glcT1+mod-5'-UTR) is approximately 9% increased relative to the α-amylase Qp of either host cell BF134 (WT glcT+WT-5'-UTR) or BF117 (WT glcT+mod-5'-UTR), and approximately 4-5% increased relative to the α-amylase Qp of host cell HM151 (variant glcT1+WT-5'-UTR).

SEQ ID NO: 1 is a synthetic nucleic acid sequence encoding a Cas9 protein.

SEQ ID NO: 2 is an amino acid sequence of an N-terminal Nuclear Localization Signal (NLS) sequence.

SEQ ID NO: 3 is an amino acid sequence of a C-terminal NLS sequence.

SEQ ID NO: 4 is an amino acid sequence comprising a deca-histidine (10-H) tag.

SEQ ID NO: 5 is a nucleic acid sequence comprising a *B. subtilis* aprE promoter.

SEQ ID NO: 6 is an Cas9 forward primer nucleic acid sequence.

SEQ ID NO: 7 is an Cas9 reverse primer nucleic acid sequence.

SEQ ID NO: 8 is a nucleic acid sequence of plasmid pKB320 backbone.

SEQ ID NO: 9 is a nucleic acid sequence of plasmid pKB320.

SEQ ID NO: 10 is a pKB320 forward primer nucleic acid sequence.

SEQ ID NO: 11 is a pKB320 reverse primer nucleic acid sequence.

SEQ ID NO: 12 is a Cas9 "reverse sequencing primer 1" nucleic acid sequence.

SEQ ID NO: 13 is a Cas9 "reverse sequencing primer 2" nucleic acid sequence.

SEQ ID NO: 14 is a Cas9 "forward sequencing primer 1" nucleic acid sequence.

SEQ ID NO: 15 is a Cas9 "forward sequencing primer 2" nucleic acid sequence.

SEQ ID NO: 16 is a Cas9 "forward sequencing primer 3" nucleic acid sequence.

SEQ ID NO: 17 is a Cas9 "forward sequencing primer 4" nucleic acid sequence.

SEQ ID NO: 18 is a Cas9 "forward sequencing primer 5" nucleic acid sequence.

SEQ ID NO: 19 is a Cas9 "forward sequencing primer 6" nucleic acid sequence.

SEQ ID NO: 20 is a Cas9 "forward sequencing primer 7" nucleic acid sequence.

SEQ ID NO: 21 is a nucleic acid sequence of pRF694.

SEQ ID NO: 22 is a *Bacillus licheniformis* wild-type glcT ORF sequence.

SEQ ID NO: 23 is a nucleic acid sequence of a *B. licheniformis* glcT gene target site.

SEQ ID NO: 24 is a synthetic nucleic acid sequence encoding glcT VT domain.

SEQ ID NO: 25 (AGG) is a three nucleotide PAM sequence of a *B. licheniformis* glcT target site.

SEQ ID NO: 26 is a synthetic nucleic acid sequence encoding Cas9 endonuclease recognition domain.

SEQ ID NO: 27 is a synthetic RNA sequence comprising a glcT guide-RNA (gRNA) nucleic acid sequence SEQ ID NO: 28 is a synthetic DNA sequence encoding a glcT gRNA.

SEQ ID NO: 29 is a *Bacillus subtilis* nucleic acid sequence comprising a rrnIp2 promoter sequence.

SEQ ID NO: 30 is a lambda phage t0 terminator nucleic acid sequence.

SEQ ID NO: 31 is a nucleic acid sequence comprising a glcT gRNA expression cassette.

SEQ ID NO: 32 is a *B. licheniformis* nucleic acid sequence comprising a 500 bp (homology arm) which is upstream (5') of nucleotide position 199 encoding a leucine (L) at amino acid residue position 67 (L67).

SEQ ID NO: 33 is a glcT 5' forward primer nucleic acid sequence.

SEQ ID NO: 34 is a glcT 5' reverse primer nucleic acid sequence.

SEQ ID NO: 35 is a *B. licheniformis* nucleic acid sequence comprising a 500 bp (homology arm) which is downstream (3') of nucleotide position 199 encoding a leucine (L) at amino acid residue position 67 (L67).

SEQ ID NO: 36 is a glcT 3' forward primer nucleic acid sequence.

SEQ ID NO: 37 is a glcT 3' reverse primer nucleic acid sequence.

SEQ ID NO: 38 is a nucleic acid sequence of pRF731.

SEQ ID NO: 39 is a nucleic acid sequence of pRF724.

SEQ ID NO: 40 is a *B. licheniformis* nucleic acid sequence comprising a duplication of rghR2 gene codons 24-29.

SEQ ID NO: 41 is a *B. licheniformis* rghR2 nucleic acid sequence comprising a rghR2 gene with duplication SEQ ID NO: 42 is an 8.3 kb PCR product of pRF694.

SEQ ID NO: 43 is a pRF694 forward primer.

SEQ ID NO: 44 is a pRF694 reverse primer.

SEQ ID NO: 45 is a synthetic rghR2 editing template gRNA cassette.

SEQ ID NO: 46 is a synthetic rghR2 nucleic acid sequence editing template.

SEQ ID NO: 47 is a rghR2 gRNA expression cassette.

SEQ ID NO: 48 is a rghR2 cassette forward primer.

SEQ ID NO: 49 is a rghR2 cassette reverse primer.

SEQ ID NO: 50 is a nucleic acid sequence comprising plasmid pBL.comK.

SEQ ID NO: 51 is a *B. licheniformis* glcT gene locus.

SEQ ID NO: 52 is a synthetic glcT locus forward primer.

SEQ ID NO: 53 is a synthetic glcT locus reverse primer.

SEQ ID NO: 54 is a synthetic glcT locus forward sequencing primer.

SEQ ID NO: 55 is an amino acid sequence of the variant GlcT (L67F) protein encoded by the glcT ORF of SEQ ID NO: 56.

SEQ ID NO: 56 is a synthetic nucleic acid sequence comprising a mutant glcT ORF (C199T) encoding the variant GlcT (L67F) protein of SEQ ID NO: 55.

SEQ ID NO: 57 is a *B. licheniformis* nucleic acid sequence comprising a rghr2 locus.

SEQ ID NO: 58 is a synthetic rghR2 locus forward primer.

SEQ ID NO: 59 is a synthetic rghR2 locus reverse primer.

SEQ ID NO: 60 is a synthetic rghR2 locus sequencing primer.

SEQ ID NO: 61 is a *B. licheniformis* nucleic acid sequence comprising arghR2 restored locus.

SEQ ID NO: 62 is a *B. subtilis* nucleic acid sequence comprising an aprE 5'-UTR.

SEQ ID NO: 63 is a synthetic nucleic acid sequence comprising a modified aprE 5'-UTR, referred to hereinafter as "aprE mod-5' UTR"

SEQ ID NO: 64 is a synthetic nucleic acid sequence comprising a wild-type 5'-UTR (WT 5'-UTR) expression construct.

SEQ ID NO: 65 is a synthetic nucleic acid sequence comprising a modified 5'-UTR expression construct.

SEQ ID NO: 66 is a *B. licheniformis* nucleic acid sequence comprising a 5' catH homology arm.

SEQ ID NO: 67 is a *B. licheniformis* nucleic acid sequence comprising a catH gene.

SEQ ID NO: 68 is a synthetic nucleic acid sequence comprising a spoVGrrnIp hybrid promoter.

SEQ ID NO: 69 is a *B. licheniformis* nucleic acid sequence comprising a lat signal sequence.

SEQ ID NO: 70 is a *G. stearothermophilus* nucleic acid sequence encoding variant *G. stearothermophilus* α-amylase.

SEQ ID NO: 71 is a *B. licheniformis* nucleic acid sequence comprising a lat terminator.

SEQ ID NO: 72 is a *B. licheniformis* nucleic acid sequence comprising a 3' catH homology arm.

SEQ ID NO: 73 is an amino acid sequence of a variant *G. stearothermophilus* α-amylase.

SEQ ID NO: 74 is a synthetic nucleic acid sequence comprising a wild-type catH locus construct.

SEQ ID NO: 75 is a synthetic nucleic acid sequence comprising a modified 5'-UTR catH locus construct.

SEQ ID NO: 76 is a synthetic catH locus forward primer.

SEQ ID NO: 77 is a synthetic catH locus reverse primer.

SEQ ID NO: 78 is a synthetic catH forward sequencing primer 1.

SEQ ID NO: 79 is a synthetic catH forward sequencing primer 2.

SEQ ID NO: 80 is a synthetic catH forward sequencing primer 3.

SEQ ID NO: 81 is nucleic acid sequence comprising a *B. licheniformis* wild-type glcT gene, encoding a wild-type GlcT protein of SEQ ID NO: 82.

SEQ ID NO: 82 is the amino acid sequence of a *B. licheniformis* wild-type GlcT protein, encoded by a *B. licheniformis* glcT ORF of SEQ ID NO: 22 or a *B. licheniformis* glcT gene of SEQ ID NO: 81.

SEQ ID NO: 83 is the amino acid sequence of a *B. licheniformis* variant RghR2 protein comprising a repeat (duplication) of six amino acids (AAAISR): $A_{32}A_{33}A_{34}I_{35}S_{36}R_{37}$-$A_{38}A_{39}A_{40}I_{41}S_{42}R_{43}$.

SEQ ID NO: 84 is the amino acid sequence of a restored (native) *B. licheniformis* RghR2 protein.

DETAILED DESCRIPTION

The instant disclosure is generally related to compositions and methods for producing and constructing *Bacillus* sp. (host) cells (e.g., protein production host cells, cell factories) having increased protein production capabilities, increased secondary metabolite production capabilities and the like. More particularly, certain embodiments of the disclosure are directed to mutant *Bacillus* sp. cells comprising a glcT gene encoding a variant GlcT (transcriptional anti-termination) protein comprising a phenylalanine (F) at amino acid position 67 (F67) of SEQ ID NO: 55. Certain other embodiments are related to genetically modified *Bacillus* sp. cells comprising an introduced polynucleotide encoding a variant GlcT protein comprising a phenylalanine (F) at amino acid position 67 (F67) of SEQ ID NO: 55.

Other embodiments of the disclosure are directed to modified *Bacillus* sp. cells comprising an edited (modified) glcT gene encoding a variant GlcT protein comprising a phenylalanine (F) at amino acid position 67 (F67) of SEQ ID NO: 55. For example, certain embodiments of the disclosure (Example 2) are related to glcT Cas9 targeting vectors and modified *Bacillus* cells thereof comprising a Cas9 edited (modified) glcT gene encoding a variant GlcT protein comprising a phenylalanine (F) at amino acid position 67 (F67) of SEQ ID NO: 55.

In certain other embodiments, the disclosure is related to modified *Bacillus* (daughter) cells comprising an inactivated (endogenous) native chromosomal glcT gene (i.e., encoding a wild-type GlcT protein comprising a leucine (L) at amino acid position 67 (L67) of SEQ ID NO: 82) and comprising an introduced polynucleotide encoding a variant GlcT protein comprising a phenylalanine (F) at amino acid position 67 (F67) of SEQ ID NO: 55. Thus, in certain embodiments, the disclosure is related to such modified *Bacillus* cells (e.g., comprising a modified glcT gene encoding a GlcT protein comprising a phenylalanine (F) at amino acid position 67 (F67) of SEQ ID NO: 55), wherein the modified *Bacillus* cells produce an increased amount of a protein of interest (POI) relative to the parental cell from which they were derived (i.e., expressing/producing the same POI).

In certain other embodiments, the disclosure is directed to an isolated polynucleotide comprising an open reading frame (ORF) encoding a variant *Bacillus* sp. GlcT (anti-termination) protein, the variant GlcT protein comprising a leucine (L) to phenylalanine (F) substitution at amino acid position 67 (L67F) of SEQ ID NO: 55. In related embodiments, the polynucleotide ORF encodes a variant GlcT protein comprising at least about 80%, 85%, 90%, 95%, 96%, 97%, 98% or 99% sequence identity to SEQ ID NO: 55 or SEQ ID NO: 82, and comprises a phenylalanine (F) at amino acid position 67 (F67) of SEQ ID NO: 55. In another embodiment, the polynucleotide comprises a nucleic acid sequence having at least about 80%, 85%, 90%, 95%, 96%, 97%, 98% or 99% sequence identity to SEQ ID NO: 22, SEQ ID NO: 81 or SEQ ID NO: 56, wherein the polynucleotide encodes a variant GlcT protein comprising a phenylalanine (F) at amino acid position 67 (F67) of SEQ ID NO: 55.

In other embodiments, the disclosure is related to a vector, a DNA expression construct and the like, comprising a polynucleotide encoding a variant GlcT protein of the disclosure. For example, in certain embodiments, a vector comprising an ORF encoding a variant GlcT protein, further comprises an upstream (5') homology region (5'-HR) operably linked (5') to the ORF sequence and/or a downstream (3') homology region (3'-HR) operably linked (3') to the ORF sequence, wherein the 5'-HR and/or the 3'-HR comprise(s) sufficient homology with a targeted genomic locus of a *Bacillus* (host) cell to effect integration of the vector into the targeted genomic locus by homologous recombination (i.e., when the vector is transformed into a competent *Bacillus* cell). For example, in certain embodiments, such vectors are introduced into a parental *Bacillus* cell comprising a glcT gene having an open reading frame (ORF) encoding a wild-type GlcT protein of SEQ ID NO: 82 (i.e., comprising a leucine (L) at amino acid position 67 (L67) of SEQ ID NO: 82), wherein the introduced vector comprises an ORF encoding the variant GlcT protein of SEQ ID NO: 55 (i.e., comprising a phenylalanine (F) at amino acid position 67 (F67) of SEQ ID NO: 55), flanked by a 5'-HR and/or 3'-HR comprising sufficient homology to the parental *Bacillus* (endogenous) nucleic acid sequence immediately upstream (5') and/or immediately downstream (3') of the glcT gene ORF chromosomal locus, to effect integration of the vector by homologous recombination, thereby deleting the ORF encoding the GlcT protein of SEQ ID NO: 82 and replacing the ORF encoding the GlcT protein of SEQ ID NO: 55.

Thus, as set forth above, certain embodiments of the disclosure are related to such genetically modified *Bacillus* (daughter) cells producing increased amounts of one or more proteins of interest (i.e., relative to the *Bacillus* parental cells producing the same protein of interest, wherein the daughter and parental cells are cultivated under similar conditions). More particularly, as described in the Examples section of the disclosure (e.g., see, Example 1), Applicant performed routine NTG mutagenesis to create a pool of *B. licheniformis* mutants (i.e., *Bacillus* daughter cells), which NTG modified (mutant) daughter cells were subsequently screened to identify *B. licheniformis* (mutant) daughter cell mutations that can increase the production of industrially relevant proteins of interest (e.g., an amylase, a protease, etc.). As presented in Example 1, a particular *B. licheniformis* (mutant) daughter cell capable of producing increased amounts of amylase protein was identified, wherein the (mutant) daughter cell differed from its parent by a single nucleotide polymorphism (SNP) in a gene encoding a variant GlcT protein. More particularly, the parental *B. licheniformis* cell comprises a glcT gene encoding a wild-type GlcT protein of SEQ ID NO: 82 (comprising a Leucine (L) amino acid at position 67 of SEQ ID NO: 82), whereas the *B. licheniformis* (mutant) daughter cell comprises a glcT gene encoding a variant GlcT protein of SEQ ID NO: 55 (comprising a Phenylalanine (F) amino acid at position 67 of SEQ ID NO: 55).

Furthermore, as presented in Example 2, Applicant constructed certain glcT Cas9 targeting vectors which change the first position of codon 67 from CTC to TTC (i.e., codon 67 of the glcT gene), thereby converting codon 67 from a Leucine (L) to a Phenylalanine (F). As presented and described in Example 3, such glcT Cas9 targeting vectors were transformed into competent (parental) *B. licheniformis* cells to generate and select modified *B. licheniformis* (daughter) cells comprising the Cas9 edited glcT gene, which modified cells thereby encode the variant GlcT protein comprising the L67F substitution. For example, as set forth in Example 3, sequence alignments comparing the sequencing data to the wild-type glcT locus revealed that some of the recovered colonies contained the desired genome edit causing the L67F mutation in the GlcT protein (SEQ ID NO: 55). More specifically, a *B. licheniformis* colony containing the modified/edited glcT gene (SEQ ID NO: 56) encoding the L67F GlcT protein (SEQ ID NO: 55), referred to herein as allele "glcT1", was stored as strain BF63 (glcT1 pBL.comK).

In certain other embodiments, a modified *Bacillus licheniformis* (daughter) cell of the disclosure, comprising a modified glcT gene (e.g., allele glcT1) encoding a variant GlcT protein, further comprises a genetic modification which restores a mutated/variant rghr2 gene. For example, Applicant's pending U.S. Provisional Patent Application Ser. No. 62/463,268, filed Feb. 24, 2017 (incorporated herein by reference in its entirety), fully describes such modified *B. licheniformis* (host) cells comprising a restored rghr2 gene (hereinafter, "rghr$2_{rest}$") and methods for producing the same. More particularly, as described in the above-referenced Provisional Application, the genomes of certain *B. licheniformis* strains/host cells were sequenced, which revealed that these sequenced strains comprise a duplication (i.e., a repeat) of 18 nucleotides (18-bp) in the rghr2 gene, wherein this 18-nucleotide (repeat) sequence encodes amino acids "AAAISR", such that the variant RghR2 protein comprises a repeat of the AAAISR amino acid sequence (i.e., AAAISR-AAAISR). Furthermore, as described in the above-referenced Application, *B. licheniformis* (daughter) cells which were genetically modified to remove the 18-bp duplication (referred to as rghr$2_{rest}$) were capable of producing increased amounts of industrially relevant proteins in comparison (vis-à-vis) to the parental *B. licheniformis* cells comprising the 18-bp duplication (un-restored rghr2).

Thus, in certain embodiments, a modified *Bacillus licheniformis* cell of the disclosure comprises a modified glcT gene encoding a variant GlcT protein. In certain other embodiments, a modified *Bacillus licheniformis* cell of the disclosure comprises a modified glcT gene and a modified rghr2 gene (i.e., rghr$2_{rest}$). More particularly, as presented in Examples 4-6 of the disclosure, Applicant further constructed rghr2 Cas9 targeting vectors (Example 4), and generated modified *Bacillus licheniformis* (daughter) cells comprising a restored rghr2 allele (i.e., rghr$2_{rest}$; Example 5, BF62 cell) and modified *Bacillus* (daughter) cells comprising a restored rghr2 allele and a modified glcT allele (i.e., rghr$2_{rest}$ and modified glcT allele; Example 6, BF169 cell).

As described in Example 7 of the disclosure, heterologous α-amylase expression cassettes were introduced into parental and modified *B. licheniformis* (daughter) cells BF62, BF63 and BF169 (e.g., see, Table 17). More specifically, the α-amylase expression cassettes presented in Example 7 were constructed to additionally test the effect of an operably linked "wild-type-5'-UTR sequence" versus an operably linked "modified-5'-UTR sequence" on the expression/production of the heterologous α-amylase. Thus, the α-amylase expression cassettes comprised either a wild-type *B. subtilis* aprE 5'-UTR (SEQ ID NO: 62) or a modified-5'-UTR (SEQ ID NO: 63) operably linked to an upstream (5') promoter and a downstream (3') open reading frame encoding the α-amylase. Thus, the parental and modified *B. licheniformis* cells constructed in Example 7 (comprising and expressing a heterologous α-amylase expression cassette), were screened for the production of α-amylase in Example 8.

As presented in Example 8 (Table 18), the following *B. licheniformis* cells were screened for α-amylase production: (i) a *B. licheniformis* cell comprising an introduced "WT-5'-UTR α-amylase expression cassette" (SEQ ID NO: 62), referred to herein as strain/cell "BF134", (ii) a *B. licheniformis* cell comprising an introduced "modified-5'-UTR α-amylase expression cassette" (SEQ ID NO: 63), referred to herein as strain/cell "BF117", (iii) a *B. licheniformis* cell comprising allele glcT1 and an introduced "WT-5'-UTR α-amylase expression cassette" (SEQ ID NO: 62), referred to herein as strain/cell "HM151" and (iv) a *B. licheniformis* cell comprising allele glcT1 and an introduced "modified-5'-UTR α-amylase expression cassette" (SEQ ID NO: 63), referred to herein as strain/cell "HM150-1". Furthermore, as presented in FIG. 2A and FIG. 2B, there is a significant increase in α-amylase activity and specific productivity from the *Bacillus* host cells comprising allele glcT1 (i.e., HM150-1 and HM151 cells) relative to the *Bacillus* host cells comprising the wild-type glcT gene (i.e., BF117 and BF134 cells).

As stated briefly above, certain other embodiments of the disclosure are related to modified *Bacillus licheniformis* cells comprising allele glcT1 and further comprising a restored rghr2 gene ($rghr2_{rest}$). For example, as presented in Example 9 of the disclosure, modified *Bacillus* cells BF118 ($rghr2_{rest}$+mod-5'-UTR amylase cassette), BF171 ($rghr2_{rest}$+glcT1+mod-5'-UTR amylase cassette), BF169 ($rghr2_{rest}$+WT-5'-UTR amylase cassette) and BF260 ($rghr2_{rest}$+glcT1+WT-5'-UTR amylase cassette) were screened for amylase production at small scale, wherein the relative amylase production of *Bacillus* cells BF171 and BF260 were significantly increased compared to the amylase production of *Bacillus* cells BF118 and BF169.

Thus, in certain other embodiments the disclosure is related to DNA expression constructs comprising an ORF of the disclosure, wherein the DNA construct further comprises a promoter nucleic acid sequence functional in *Bacillus* sp. cells, wherein the promoter sequence is operably linked and upstream (5') of the ORF sequence. In certain embodiments, the DNA construct further comprises a modified *B. subtilis* aprE 5'-untranslated region sequence (mod-5'-UTR) of SEQ ID NO: 63, wherein the mod-5'-UTR is downstream (3') and operably linked to the promoter sequence and upstream (5') and operably linked to the ORF sequence. In another embodiment, the DNA construct further comprises a terminator sequence downstream (3') and operably linked to the ORF sequence.

Other embodiments of the disclosure are related to compositions and methods for producing increased amounts of an endogenous protein of interest (POI) and/or a heterologous POI in a modified *Bacillus* (host) cell of the disclosure. For example, in certain embodiments, a method for producing increased amounts of an endogenous protein of interest (POI) in a modified *Bacillus* (host) cell of the disclosure comprises (a) cultivating a modified *Bacillus* (host) cell comprising a glcT gene encoding a GlcT protein comprising a phenylalanine (F) at amino acid position 67 (F67) of SEQ ID NO: 55, in a medium suitable for the production of an endogenous POI and (b) recovering the endogenous POI from the cultivation medium, wherein the modified *Bacillus* cell produces an increased amount of the endogenous POI relative to an unmodified (parental) *Bacillus* cell producing the same endogenous POI, when cultivated under identical conditions.

In certain other embodiments, the disclosure is related to a method for producing increased amounts of a heterologous POI in a modified *Bacillus* (host) cell of the disclosure comprising (a) cultivating a modified *Bacillus* (host) cell comprising a modified glcT gene encoding a variant GlcT protein (i.e., comprising a phenylalanine (F) at amino acid position 67 (F67) of SEQ ID NO: 55) in a medium suitable for the production of a heterologous POI, wherein the modified cell and parental cell comprise an introduced polynucleotide sequence directing synthesis of the heterologous POI and (b) recovering the heterologous POI from the cultivation medium, wherein the modified *Bacillus* cell produces an increased amount of the heterologous POI relative to the parental *Bacillus* cell (i.e., comprising a wild-type glcT gene encoding a wild-type GlcT protein of SEQ ID NO: 82), when cultivated under identical conditions.

Thus, certain other embodiments of the disclosure are related to compositions and methods for constructing such modified *Bacillus* cells capable of producing increased amounts heterologous and/or endogenous proteins of interest. For example, certain compositions and methods are related to modified *Bacillus* (daughter) cells derived from unmodified *Bacillus* (parental) cells comprising (a) obtaining a parental *Bacillus* cell comprising an endogenous chromosomal wild-type glcT gene encoding a GlcT protein comprising at least 90% sequence identity to SEQ ID NO: 82 and comprising a leucine (L) at amino acid position 67 (L67) of SEQ ID NO: 82, (b) modifying the parental cell of step (a) by introducing a polynucleotide sequence directing synthesis of a variant GlcT protein comprising 90% sequence identity to SEQ ID NO: 55, comprising a phenylalanine (F) at amino acid position 67 (F67) of SEQ ID NO: 55, and (c) cultivating the modified *B. licheniformis* (daughter) cell in a medium suitable for the production of the POI, wherein the modified *B. licheniformis* (daughter) cell produces an increased amount of the POI relative to the parental *B. licheniformis* cell producing the same POI, when daughter and parental cells are cultivated under identical conditions. Thus, in certain other embodiments, a modified *Bacillus* (daughter) cell of the disclosure is derived from an unmodified *Bacillus* (parental) cell, wherein the endogenous chromosomal wild-type glcT gene (i.e., comprising a leucine (L) at amino acid position 67 (L67) of SEQ ID NO: 82) in the parental cell is modified by means of a Cas9 targeting vector, wherein the edited (modified) glcT gene encodes a variant GlcT protein comprising a phenylalanine (F) at amino acid position 67 (F67) of SEQ ID NO: 55. Thus, certain embodiments of the disclosure are related to Cas9 edited genes, including, but not limited to, a Cas9 edited glcT gene, a Cas9 edited rghr2 gene, combinations thereof and the like.

In certain embodiments, the POI is a heterologous POI, wherein a polynucleotide sequence directing synthesis of the heterologous POI is introduced into the daughter and parental cells. In other embodiments, the POI is an endogenous or heterologous enzyme.

I. Definitions

In view of the modified *Bacillus* sp. cells producing one or more heterologous and/or endogenous proteins of interest, and methods thereof described herein, the following terms and phrases are defined. Terms not defined herein should be accorded their ordinary meaning as used in the art.

Unless defined otherwise, all technical and scientific terms used herein have the same meaning as commonly understood by one of ordinary skill in the art to which the present compositions and methods apply. Although any methods and materials similar or equivalent to those described herein can also be used in the practice or testing of the present compositions and methods, representative illustrative methods and materials are now described. All publications and patents cited herein are incorporated by reference in their entirety.

It is further noted that the claims may be drafted to exclude any optional element. As such, this statement is intended to serve as antecedent basis for use of such exclusive terminology as "solely," "only", "excluding", "not including" and the like, in connection with the recitation of claim elements, or use of a "negative" limitation or proviso thereof.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

As used herein, "host cell" refers to a cell that has the capacity to act as a host or expression vehicle for a newly introduced DNA sequence. Thus, in certain embodiments of the disclosure, the host cells are *Bacillus* sp. cells or *E. coli* cells.

As defined herein, a "parental cell" or a "parental (host) cell" may be used interchangeably and refer to "unmodified" parental cells. For example, a "parental" cell refers to any cell or strain of microorganism in which the genome of the "parental" cell is altered (e.g., via one or more mutations/modifications introduced into the parental cell) to generate a modified "daughter" cell thereof.

As used herein, a "modified cell" or a "modified (host) cell" may be used interchangeably and refer to recombinant (host) cells that comprise at least one genetic modification which is not present in the "parental" host cell from which the modified cells are derived.

In certain embodiments, the "unmodified" (parental) cell may be referred to as a "control cell", particularly when being compared with, or relative to, a "modified" *Bacillus* sp. (daughter) cell. As used herein, when the expression and/or production of a protein of interest (POI) in an "unmodified" (parental) cell (e.g., a control cell) is being compared to the expression and/or production of the same POI in a "modified" (daughter) cell, it will be understood that the "modified" and "unmodified" cells are grown/cultivated/fermented under the same conditions (e.g., the same conditions such as media, temperature, pH and the like).

As used herein, "the genus *Bacillus*" or "*Bacillus* sp." cells include all species within the genus "*Bacillus*" as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulars, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*".

As used herein, a polynucleotide sequence of SEQ ID NO: 22 encodes a wild-type GlcT protein of SEQ ID NO: 82, and a polynucleotide sequence of SEQ ID NO: 56 encodes a variant GlcT protein of SEQ ID NO: 55. For example, as presented in FIG. 1A of the disclosure, the two aligned polynucleotide (ORF) sequences (SEQ ID NO: 22 vs. SEQ ID NO: 56), differ by a SNP at nucleotide position 199, wherein position 199 of SEQ ID NO: 22 comprises a cytosine (C) and position 199 of SEQ ID NO: 56 comprises a thymine (T) (e.g., see FIG. 1A black boxed nucleotides (C) and (T) at position 199). Similarly, FIG. 1B presents an alignment of the encoded wild-type GlcT protein (SEQ ID NO: 82) and the encoded variant GlcT protein (SEQ ID NO: 55), wherein the (C) to (T) SNP at position 199 of SEQ ID NO: 56 (see, FIG. 1A), results in a leucine (L) to phenylalanine (F) substitution at amino acid residue position 67 of SEQ ID NO: 55 (e.g., see FIG. 1B, black boxed (L) and (F) amino acids at residue position 67 of SEQ ID NO: 22 and SEQ ID NO: 55, respectively).

As used herein, the term "glcT1" or "allele glcT1" particularly refers to a *Bacillus* sp. cell comprising a mutated, modified, edited or introduced glcT gene (i.e., allele glcT1; SEQ ID NO: 56) encoding the L67F GlcT protein of SEQ ID NO: 55. In certain embodiments, allele glcT1 encodes a GlcT protein having about 90%, 91%, 92%, 93%, 94%, 95%, 96%, 97%, 98% or 99% sequence identity to SEQ ID NO: 55 and comprises a L67F substation at amino acid position 67 of SEQ ID NO: 55.

As used herein, a "wild-type *B. subtilis* aprE 5'-UTR" (abbreviated hereinafter, "WT-5'-UTR") comprises SEQ ID NO: 62 and a "modified aprE 5'-UTR" (abbreviated hereinafter, "mod-5'-UTR") comprises SEQ ID NO: 63. For example, the α-amylase expression cassettes described in Example 7 (i.e., SEQ ID NO: 64 and SEQ ID NO: 65) were constructed to additionally test the effect of an operably linked "WT-5'-UTR sequence" versus an operably linked "mod-5'-UTR sequence" on the expression/production of the heterologous α-amylase. Thus, the α-amylase expression cassettes comprised either a WT-5'-UTR sequence (SEQ ID NO: 62) or a mod-5'-UTR sequence (SEQ ID NO: 63) operably linked to an upstream (5') promoter and a downstream (3') open reading frame encoding the α-amylase.

As used herein, a "*Bacillus* (daughter) cell/strain" named "BF134" comprises an introduced amylase expression construct of SEQ ID NO: 64.

As used herein, a "*Bacillus* (daughter) cell/strain" named "BF117" comprises an introduced amylase expression construct of SEQ ID NO: 65.

As used herein, a "*Bacillus* (daughter) cell/strain" named "BF63" comprises allele glcT1 (glcT1 (L67F)/pBL.comK) encoding the L67F GlcT protein of SEQ ID NO: 55 and plasmid pBL.comK encoding/expressing a ComK protein.

As used herein, a "*Bacillus* (daughter) cell/strain" named "HM151" comprises allele glcT1 and an introduced amylase expression construct of SEQ ID NO: 64.

As used herein, a "*Bacillus* (daughter) cell/strain" named "HM150-1" comprises allele glcT1 and an introduced amylase expression construct of SEQ ID NO: 65.

As used herein, a "*Bacillus* (daughter) cell/strain" named "BF62" comprises a restored rghr2 gene (hereinafter, "$rghr2_{rest}$"). The rghr2 gene and its restored form "$rghr2_{rest}$" are further described below.

As used herein, a "*Bacillus* (daughter) cell/strain" named "BF165" comprises $rghr2_{rest}$ and an introduced amylase expression construct of SEQ ID NO: 64.

As used herein, a "*Bacillus* (daughter) cell/strain" named "BF118" comprises $rghr2_{rest}$ and an introduced amylase expression construct of SEQ ID NO: 65.

As used herein, a "*Bacillus* (daughter) cell/strain" named "BF260" comprises allele glcT1 and rghr$2_{rest}$; and an introduced amylase expression construct of SEQ ID NO: 64.

As used herein, a "*Bacillus* (daughter) cell/strain" named "BF171" comprises allele glcT1 and rghr$2_{rest}$; and an introduced amylase expression construct of SEQ ID NO: 65.

As used herein, a "variant *B. licheniformis* chromosomal rghR2 gene" of SEQ ID NO: 41 comprises an 18-nucleotide (18-bp) duplication encoding a consecutive repeat of six (6) amino acids which are "Ala-Ala-Ala-Ile-Ser-Arg" (hereinafter "AAAISR"), wherein the primary (1°) amino acid sequence of the encoded variant RghR2 protein of SEQ ID NO: 83 comprises a linear (consecutive) repeat of these six (6) amino acids as follows: "Ala-Ala-Ala-Ile-Ser-Arg-Ala-Ala-Ala-Ile-Ser-Arg"; hereinafter, "AAAISRAAAISR". For example, the six amino acid repeat present in RghR2 protein of SEQ ID NO: 83 is set forth below in Table 1, wherein the repeated amino acid residues of this 140 amino acid protein comprise the bold text amino acids at positions 38-43 of SEQ ID NO: 83.

In contrast, a "restored *B. licheniformis* chromosomal rghR2 gene" of the disclosure (SEQ ID NO: 61) does not comprise this 18-nucleotide (18-bp) duplication. Thus, the restored rghR2 gene of SEQ ID NO: 61 encodes a native RghR2 protein of SEQ ID NO: 84 (i.e., which does not comprise the consecutive repeat "AAAISR").

TABLE 1

VARIANT AND RESTORED (NATIVE) RghR2 PROTEINS

| SEQ | RghR2 PROTEIN SEQUENCE |
|---|---|
| 83 | MAMTRFGERLKELREQRSLSVNQLAMYAGVS$A_{32}A_{33}A_{34}I_{35}S_{36}R_{37}A_{38}A_{39}A_{40}I_{41}S_{42}R_{43}$IENGHRGVPKPATIRKLAEALKMPYEQLMDIAGYMRADEIREQPRGYVTMQEIAAKHGVEDLWLFKPEKWDCLSREDLLNLEQYFHFLVNEAKKRQS |
| 84 | MAMTRFGERLKELREQRSLSVNQLAMYAGVS$A_{32}A_{33}A_{34}I_{35}S_{36}R_{37}$IENGHRGVPKPATIRKLAEALKMPYEQLMDIAGYMRADEIREQPRGYVTMQEIAAKHGVEDLWLFKPEKWDCLSREDLLNLEQYFHFLVNEAKKRQS |

Thus, as used herein, the phrases "deleting the 18-nucleotide duplication", or "deleting the 18-bp duplication" or "modifying the cell by deleting the 18-nucleotide duplication" particularly refer to a genetic modification of a parental *Bacillus* cell comprising a variant rghR2 gene comprising an 18-nucleotide duplication, which duplication encodes a repeat of amino acids "AAAISR" in the variant RghR2 protein (e.g., see Table 1; SEQ ID NO: 83, wherein amino acids "AAAISR" at positions 32-37 of SEQ ID NO: 83 are consecutively repeated at positions 38-43 of SEQ ID NO: 83). Thus, in certain embodiments, a modified *Bacillus* cell of the disclosure is derived from a parental *Bacillus* cell comprising a variant chromosomal rghR2 gene comprising an 18-nucleotide duplication encoding the "AAAISR" repeated sequence, wherein the modified *Bacillus* cell is modified by "deleting the 18-nucleotide duplication", thereby resulting in a modified *Bacillus* cell comprising a "restored" rghR2 gene (rghR$2_{rest}$) sequence encoding a native rghR2 protein of SEQ ID NO: 84. For a more detailed description of the rghR2 gene, the (18-bp duplication) rghR2 variant thereof (SEQ ID NO: 83) and the restoration of the rghR2 variant back to a native rghR2 gene (rghR$2_{rest}$; SEQ ID NO: 84), see Applicant's U.S. Provisional Patent Application Ser. No. 62/463,268, filed Feb. 24, 2017, incorporated herein by reference in its entirety.

As defined herein, the terms "increased expression", "enhanced expression", "increased expression of a POI", "increased production", "increased production of a POI" and the like refer to a "modified" *Bacillus* (daughter) cell, wherein the "increase" is always relative (vis-à-vis) to an "unmodified" *Bacillus* (parental) cell expressing/producing the same POI.

As used herein, the term "expression" refers to the transcription and stable accumulation of sense (mRNA) or anti-sense RNA, derived from a nucleic acid molecule of the disclosure. Expression may also refer to translation of mRNA into a polypeptide. Thus, the term "expression" includes any step involved in the production of the polypeptide including, but not limited to, transcription, post-transcriptional modification, translation, post-translational modification, secretion and the like.

As defined herein, the combined term "expresses/produces", as used in phrases such as "a modified host cell expresses/produces an increased amount of a protein of interest relative to the (unmodified) parental host cell", the term ("expresses/produces") is meant to include any steps involved in the expression and production of a protein of interest in host cell of the disclosure.

Likewise, as used herein, an "increased amount", when used in phrases such as "a modified host cell 'expresses/produces an increased amount' of one or more proteins of interest relative to the (unmodified) parental host cell", particularly refers to an "increased amount" of any protein of interest (POI) expressed/produced in the modified host cell, which "increased amount" is always relative to the (unmodified) parental *Bacillus* cells expressing/producing the same POI, wherein the modified and unmodified cells are grown/cultured/fermented under essentially the same conditions (e.g., the same conditions such as media, temperature, pH and the like). For example, an increased amount of a POI may be an endogenous *Bacillus* POI or a heterologous POI expressed in a modified *Bacillus* cell of the disclosure.

Thus, as used herein, "increasing" protein production or "increased" protein production is meant an increased amount of protein produced (e.g., a protein of interest). The protein may be produced inside the host cell, or secreted (or transported) into the culture medium. In certain embodiments, the protein of interest is produced (secreted) into the culture medium. Increased protein production may be detected for example, as higher maximal level of protein or enzymatic activity (e.g., such as protease activity, amylase activity, cellulase activity, hemicellulase activity and the like), or total extracellular protein produced as compared to the parental host cell.

As used herein, "nucleic acid" refers to a nucleotide or polynucleotide sequence, and fragments or portions thereof, as well as to DNA, cDNA, and RNA of genomic or synthetic origin, which may be double-stranded or single-stranded, whether representing the sense or antisense strand. It will be understood that as a result of the degeneracy of the genetic code, a multitude of nucleotide sequences may encode a given protein.

It is understood that the polynucleotides (or nucleic acid molecules) described herein include "genes", "vectors" and "plasmids".

Accordingly, the term "gene", refers to a polynucleotide that codes for a particular sequence of amino acids, which comprise all, or part of a protein coding sequence, and may include regulatory (non-transcribed) DNA sequences, such as promoter sequences, which determine for example the conditions under which the gene is expressed. The transcribed region of the gene may include untranslated regions (UTRs), including introns, 5'-untranslated regions (UTRs), and 3'-UTRs, as well as the coding sequence.

As used herein, the term "coding sequence" refers to a nucleotide sequence, which directly specifies the amino acid sequence of its (encoded) protein product. The boundaries of the coding sequence are generally determined by an open reading frame (hereinafter, "ORF"), which usually begins with an ATG start codon. The coding sequence typically includes DNA, cDNA, and recombinant nucleotide sequences.

As defined herein, the term "open reading frame" (hereinafter, "ORF") means a nucleic acid or nucleic acid sequence (whether naturally occurring, non-naturally occurring, or synthetic) comprising an uninterrupted reading frame consisting of (i) an initiation codon, (ii) a series of two (2) or more codons representing amino acids, and (iii) a termination codon, the ORF being read (or translated) in the 5' to 3' direction.

The term "promoter" as used herein refers to a nucleic acid sequence capable of controlling the expression of a coding sequence or functional RNA. In general, a coding sequence is located 3' (downstream) to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" as used herein refers to the association of nucleic acid sequences on a single nucleic acid fragment so that the function of one is affected by the other. For example, a promoter is operably linked with a coding sequence (e.g., an ORF) when it is capable of affecting the expression of that coding sequence (i.e., that the coding sequence is under the transcriptional control of the promoter). Coding sequences can be operably linked to regulatory sequences in sense or antisense orientation.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, "a functional promoter sequence controlling the expression of a gene of interest (or open reading frame thereof) linked to the gene of interest's protein coding sequence" refers to a promoter sequence which controls the transcription and translation of the coding sequence in *Bacillus*. For example, in certain embodiments, the present disclosure is directed to a polynucleotide comprising a 5' promoter (or 5' promoter region, or tandem 5' promoters and the like), wherein the promoter region is operably linked to a nucleic acid sequence encoding a protein of interest. Thus, in certain embodiments, a functional promoter sequence controls the expression of a gene of interest encoding a protein of interest. In other embodiments, a functional promoter sequence controls the expression of a heterologous gene or an endogenous gene encoding a protein of interest in a *Bacillus* cell.

As defined herein, "suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As defined herein, the term "introducing", as used in phrases such as "introducing into a bacterial cell" or "introducing into a *Bacillus* cell" at least one polynucleotide open reading frame (ORF), or a gene thereof, or a vector thereof, includes methods known in the art for introducing polynucleotides into a cell, including, but not limited to protoplast fusion, natural or artificial transformation (e.g., calcium chloride, electroporation), transduction, transfection, conjugation and the like (e.g., see Ferrari et al., 1989).

As used herein, "transformed" or "transformation" mean a cell has been transformed by use of recombinant DNA techniques. Transformation typically occurs by insertion of one or more nucleotide sequences (e.g., a polynucleotide, an ORF or gene) into a cell. The inserted nucleotide sequence may be a heterologous nucleotide sequence (i.e., a sequence that is not naturally occurring in cell that is to be transformed). As used herein, "transformation" refers to introducing an exogenous DNA into a host cell so that the DNA is maintained as a chromosomal integrant or a self-replicating extra-chromosomal vector. As used herein, "transforming DNA", "transforming sequence", and "DNA construct" refer to DNA that is used to introduce sequences into a host cell or organism. Transforming DNA is DNA used to introduce sequences into a host cell or organism. The DNA may be generated in vitro by PCR or any other suitable techniques. In some embodiments, the transforming DNA comprises an incoming sequence, while in other embodiments it further comprises an incoming sequence flanked by homology boxes. In yet a further embodiment, the transforming DNA comprises other non-homologous sequences, added to the ends (i.e., stuffer sequences or flanks). The ends can be closed such that the transforming DNA forms a closed circle, such as, for example, insertion into a vector.

As used herein "an incoming sequence" refers to a DNA sequence that is introduced into the *Bacillus* chromosome. In some embodiments, the incoming sequence is part of a DNA construct. In other embodiments, the incoming sequence encodes one or more proteins of interest. In some embodiments, the incoming sequence comprises a sequence that may or may not already be present in the genome of the cell to be transformed (i.e., it may be either a homologous or heterologous sequence). In some embodiments, the incoming sequence encodes one or more proteins of interest, a gene, and/or a mutated or modified gene. In alternative embodiments, the incoming sequence encodes a functional wild-type gene or operon, a functional mutant gene or operon, or a nonfunctional gene or operon. In some embodiments, the non-functional sequence may be inserted into a gene to disrupt function of the gene. In another embodiment, the incoming sequence includes a selective marker. In a further embodiment the incoming sequence includes two homology boxes (e.g., up-stream and down-stream homology arms).

As used herein, "homology box" refers to a nucleic acid sequence, which is homologous to a sequence in the *Bacillus* chromosome. More specifically, a homology box is an upstream or downstream region having between about 80 and 100% sequence identity, between about 90 and 100% sequence identity, or between about 95 and 100% sequence identity with the immediate flanking coding region of a gene or part of a gene to be deleted, disrupted, inactivated, down-regulated and the like, according to the invention. These sequences direct where in the *Bacillus* chromosome a DNA construct is integrated and directs what part of the *Bacillus* chromosome is replaced by the incoming sequence. While not meant to limit the present disclosure, a homology box may include about between 1 base pair (bp) to 200 kilobases (kb). Preferably, a homology box includes about between 1 bp and 10.0 kb; between 1 bp and 5.0 kb; between 1 bp and 2.5 kb; between 1 bp and 1.0 kb, and between 0.25 kb and 2.5 kb. A homology box may also include about 10.0 kb, 5.0 kb, 2.5 kb, 2.0 kb, 1.5 kb, 1.0 kb, 0.5 kb, 0.25 kb and 0.1 kb. In some embodiments, the 5' and 3' ends of a selective marker are flanked by a homology box (homology arms) wherein the homology box comprises nucleic acid sequences immediately flanking the coding region of the gene.

In still another embodiment of the disclosure, the deletion, disruption, inactivation or down-regulation of a gene active at an inappropriate time, as determined by DNA array analysis (e.g., transcriptome analysis, as described herein) provides enhanced expression of a protein of interest. As used herein, "transcriptome analysis" refers to the analysis of gene transcription.

As used herein, the term "selectable marker-encoding nucleotide sequence" refers to a nucleotide sequence which is capable of expression in the host cells and where expression of the selectable marker confers to cells containing the expressed gene the ability to grow in the presence of a corresponding selective agent or lack of an essential nutrient.

As used herein, the terms "selectable marker" and "selective marker" refer to a nucleic acid (e.g., a gene) capable of expression in host cell which allows for ease of selection of those hosts containing the vector. Examples of such selectable markers include, but are not limited to, antimicrobials. Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation.

A "residing selectable marker" is one that is located on the chromosome of the microorganism to be transformed. A residing selectable marker encodes a gene that is different from the selectable marker on the transforming DNA construct. Selective markers are well known to those of skill in the art. As indicated above, the marker can be an antimicrobial resistance marker (e.g., $amp^R$, $phleo^R$, $spec^R$, $kan^R$, $ery^R$, $tet^R$, $cmp^R$ and $neo^R$ (see e.g., Guerot-Fleury, 1995; Palmeros et al., 2000; and Trieu-Cuot et al., 1983). In some embodiments, the present invention provides a chloramphenicol resistance gene (e.g., the gene present on pC194, as well as the resistance gene present in the *Bacillus licheniformis* genome). This resistance gene is particularly useful in the present invention, as well as in embodiments involving chromosomal amplification of chromosomally integrated cassettes and integrative plasmids (See e.g., Albertini and Galizzi, 1985; Stahl and Ferrari, 1984). Other markers useful in accordance with the invention include, but are not limited to auxotrophic markers, such as serine, lysine, tryptophan; and detection markers, such as β-galactosidase.

As defined herein, a host cell "genome", a bacterial (host) cell "genome", or a *Bacillus* (host) cell "genome" includes chromosomal and extrachromosomal genes.

As used herein, the terms "plasmid", "vector" and "cassette" refer to extrachromosomal elements, often carrying genes which are typically not part of the central metabolism of the cell, and usually in the form of circular double-stranded DNA molecules. Such elements may be autonomously replicating sequences, genome integrating sequences, phage or nucleotide sequences, linear or circular, of a single-stranded or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A used herein, a "transformation cassette" refers to a specific vector comprising a gene (or ORF thereof), and having elements in addition to the foreign gene that facilitate transformation of a particular host cell.

As used herein, the term "vector" refers to any nucleic acid that can be replicated (propagated) in cells and can carry new genes or DNA segments into cells. Thus, the term refers to a nucleic acid construct designed for transfer between different host cells. Vectors include viruses, bacteriophage, pro-viruses, plasmids, phagemids, transposons, and artificial chromosomes such as YACs (yeast artificial chromosomes), BACs (bacterial artificial chromosomes), PLACs (plant artificial chromosomes), and the like, that are "episomes" (i.e., replicate autonomously or can integrate into a chromosome of a host organism).

An "expression vector" refers to a vector that has the ability to incorporate and express heterologous DNA in a cell. Many prokaryotic and eukaryotic expression vectors are commercially available and know to one skilled in the art. Selection of appropriate expression vectors is within the knowledge of one skilled in the art.

As used herein, the terms "expression cassette" and "expression vector" refer to a nucleic acid construct generated recombinantly or synthetically, with a series of specified nucleic acid elements that permit transcription of a particular nucleic acid in a target cell (i.e., these are vectors or vector elements, as described above). The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In some embodiments, DNA constructs also include a series of specified nucleic acid elements that permit transcription of a particular nucleic acid in a target cell. In certain embodiments, a DNA construct of the disclosure comprises a selective marker and an inactivating chromosomal or gene or DNA segment as defined herein.

As used herein, a "targeting vector" is a vector that includes polynucleotide sequences that are homologous to a region in the chromosome of a host cell into which the targeting vector is transformed and that can drive homologous recombination at that region. For example, targeting vectors find use in introducing mutations into the chromosome of a host cell through homologous recombination. In some embodiments, the targeting vector comprises other non-homologous sequences, e.g., added to the ends (i.e., stuffer sequences or flanking sequences). The ends can be closed such that the targeting vector forms a closed circle, such as, for example, insertion into a vector. Selection and/or construction of appropriate vectors is well within the knowledge of those having skill in the art.

As used herein, the term "plasmid" refers to a circular double-stranded (ds) DNA construct used as a cloning vector, and which forms an extrachromosomal self-replicating genetic element in many bacteria and some eukaryotes. In some embodiments, plasmids become incorporated into the genome of the host cell.

As used herein, the term "protein of interest" or "POI" refers to a polypeptide of interest that is desired to be expressed in a modified *Bacillus* (daughter) cell, wherein the POI is preferably expressed at increased levels (i.e., relative to the "unmodified" (parental) cell). Thus, as used herein, a POI may be an enzyme, a substrate-binding protein, a surface-active protein, a structural protein, a receptor protein, an antibody and the like Similarly, as defined herein, a "gene of interest" or "GOT" refers a nucleic acid sequence (e.g., a polynucleotide, a gene or an ORF) which encodes a POI. A "gene of interest" encoding a "protein of interest" may be a naturally occurring gene, a mutated gene or a synthetic gene.

In certain embodiments, a modified cell of the disclosure produces an increased amount of a heterologous POI or an endogenous POI relative to the parental cell. In particular embodiments, an increased amount of a POI produced by a modified cell of the disclosure is at least a 0.05% increase, at least 0.10%, at least a 1.0% increase, at least a 5.0% increase, or a greater than 5.0% increase, relative to the parental cell. As a non-limiting example, in certain embodiments, the POI is an enzyme (e.g., amylase, a protease, etc.), wherein an increased level of the POI produced by the modified cell (i.e., relative to its unmodified parent) is detected or measured as an increase in enzymatic activity and/or an increase specific productivity (Qp).

As used herein, the terms "polypeptide" and "protein" are used interchangeably, and refer to polymers of any length comprising amino acid residues linked by peptide bonds. The conventional one (1) letter or three (3) letter codes for amino acid residues are used herein. The polypeptide may be linear or branched, it may comprise modified amino acids, and it may be interrupted by non-amino acids. The term polypeptide also encompasses an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

In certain embodiments, a gene of the instant disclosure encodes a commercially relevant industrial protein of interest, such as an enzyme (e.g., a acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof).

As used herein, a "variant" polypeptide refers to a polypeptide that is derived from a parent (or reference) polypeptide by the substitution, addition, or deletion of one or more amino acids, typically by recombinant DNA techniques. Variant polypeptides may differ from a parent polypeptide by a small number of amino acid residues and may be defined by their level of primary amino acid sequence homology/identity with a parent (reference) polypeptide.

Preferably, variant polypeptides have at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity with a parent (reference) polypeptide sequence. As used herein, a "variant" polynucleotide refers to a polynucleotide encoding a variant polypeptide, wherein the "variant polynucleotide" has a specified degree of sequence homology/identity with a parent polynucleotide, or hybridizes with a parent polynucleotide (or a complement thereof) under stringent hybridization conditions. Preferably, a variant polynucleotide has at least 70%, at least 75%, at least 80%, at least 85%, at least 90%, at least 91%, at least 92%, at least 93%, at least 94%, at least 95%, at least 96%, at least 97%, at least 98%, or even at least 99% nucleotide sequence identity with a parent (reference) polynucleotide sequence.

As used herein, a "mutation" refers to any change or alteration in a nucleic acid sequence. Several types of mutations exist, including point mutations, deletion mutations, silent mutations, frame shift mutations, splicing mutations and the like. Mutations may be performed specifically (e.g., via site directed mutagenesis) or randomly (e.g., via chemical agents, passage through repair minus bacterial strains).

As used herein, in the context of a polypeptide or a sequence thereof, the term "substitution" means the replacement (i.e., substitution) of one amino acid with another amino acid.

As defined herein, an "endogenous gene" refers to a gene in its natural location in the genome of an organism.

As defined herein, a "heterologous" gene, a "non-endogenous" gene, or a "foreign" gene refer to a gene (or ORF) not normally found in the host organism, but that is introduced into the host organism by gene transfer. As used herein, the term "foreign" gene(s) comprise native genes (or ORFs) inserted into a non-native organism and/or chimeric genes inserted into a native or non-native organism.

As defined herein, a "heterologous" nucleic acid construct or a "heterologous" nucleic acid sequence has a portion of the sequence which is not native to the cell in which it is expressed.

As defined herein, a "heterologous control sequence", refers to a gene expression control sequence (e.g., a promoter or enhancer) which does not function in nature to regulate (control) the expression of the gene of interest. Generally, heterologous nucleic acid sequences are not endogenous (native) to the cell, or a part of the genome in which they are present, and have been added to the cell, by infection, transfection, transformation, microinjection, electroporation, and the like. A "heterologous" nucleic acid construct may contain a control sequence/DNA coding (ORF) sequence combination that is the same as, or different, from a control sequence/DNA coding sequence combination found in the native host cell.

As used herein, the terms "signal sequence" and "signal peptide" refer to a sequence of amino acid residues that may participate in the secretion or direct transport of a mature protein or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "derived" encompasses the terms "originated" "obtained," "obtainable," and "created," and generally indicates that one specified material or composition finds its origin in another specified material or composition, or has features that can be described with reference to the another specified material or composition.

As used herein, the term "homology" relates to homologous polynucleotides or polypeptides. If two or more polynucleotides or two or more polypeptides are homologous, this means that the homologous polynucleotides or polypeptides have a "degree of identity" of at least 60%, more preferably at least 70%, even more preferably at least 85%, still more preferably at least 90%, more preferably at least 95%, and most preferably at least 98%. Whether two polynucleotide or polypeptide sequences have a sufficiently high degree of identity to be homologous as defined herein, can suitably be investigated by aligning the two sequences using a computer program known in the art, such as "GAP" provided in the GCG program package (Program Manual for the Wisconsin Package, Version 8, August 1994, Genetics Computer Group, 575 Science Drive, Madison, Wis., USA 53711) (Needleman and Wunsch, (1970). Using GAP with the following settings for DNA sequence comparison: GAP creation penalty of 5.0 and GAP extension penalty of 0.3.

As used herein, the term "percent (%) identity" refers to the level of nucleic acid or amino acid sequence identity between the nucleic acid sequences that encode a polypeptide or the polypeptide's amino acid sequences, when aligned using a sequence alignment program.

As used herein, "specific productivity" is total amount of protein produced per cell per time over a given time period.

As defined herein, the terms "purified", "isolated" or "enriched" are meant that a biomolecule (e.g., a polypeptide or polynucleotide) is altered from its natural state by virtue of separating it from some, or all of, the naturally occurring constituents with which it is associated in nature. Such isolation or purification may be accomplished by art-recognized separation techniques such as ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis or separation on a gradient to remove whole cells, cell debris, impurities, extraneous proteins, or enzymes undesired in the final composition. It is further possible to then add constituents to a purified or isolated biomolecule composition which provide additional benefits, for example, activating agents, anti-inhibition agents, desirable ions, compounds to control pH or other enzymes or chemicals.

As used herein, a "variant *Geobacillus stearothermophilus* amylase" is a variant G. *stearothermophilus* α-amylase disclosed in International PCT Publication No. WO2009/149130.

As used herein, the term "ComK polypeptide" is defined as the product of a comK gene; a transcription factor that acts as the final auto-regulatory control switch prior to competence development; involved with activation of the expression of late competence genes involved in DNA-binding and uptake and in recombination (Liu and Zuber, 1998, Hamoen et al., 1998). A plasmid (pBL.comK) comprising and expressing the comK nucleic acid sequence is set forth in SEQ ID NO: 50.

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "orthologue" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "homology" refers to sequence similarity or identity, with identity being preferred. This homology is determined using standard techniques known in the art (See e.g., Smith and Waterman, 1981; Needleman and Wunsch, 1970; Pearson and Lipman, 1988; programs such as GAP, BESTFIT, FASTA, and TFASTA in the Wisconsin Genetics Software Package (Genetics Computer Group, Madison, Wis.) and Devereux et. al., 1984).

As used herein, an "analogous sequence" is one wherein the function of the gene is essentially the same as the gene derived from a *Bacillus* cell. Additionally, analogous genes include at least 60%, 65%, 70%, 75%, 80%, 85%, 90%, 95%, 97%, 98%, 99% or 100% sequence identity with the sequence of the *Bacillus* sp. cell. Analogous sequences are determined by known methods of sequence alignment. A commonly used alignment method is BLAST, although there are other methods that also find use in aligning sequences.

As used herein, the term "hybridization" refers to the process by which a strand of nucleic acid joins with a complementary strand through base pairing, as known in the art. A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature ($T_m$) of the nucleic acid binding complex or probe. For example, "maximum stringency" typically occurs at about $T_m$−5° C. (5° below the $T_m$ of the probe); "high stringency" at about 5-10° C. below the $T_m$; "intermediate stringency" at about 10-20° C. below the $T_m$ of the probe; and "low stringency" at about 20-25° C. below the $T_m$. Functionally, maximum stringency conditions may be used to identify sequences having strict identity or near-strict identity with the hybridization probe; while an intermediate or low stringency hybridization can be used to identify or detect polynucleotide sequence homologs. Moderate and high stringency hybridization conditions are well known in the art. An example of high stringency conditions includes hybridization at about 42° C. in 50% formamide, 5×SSC, 5×Denhardt's solution, 0.5% SDS and 100 pg/ml denatured carrier DNA, followed by washing two times in 2×SSC and 0.5% SDS at room temperature (RT) and two additional times in 0.1×SSC and 0.5% SDS at 42° C. An example of moderate stringent conditions including overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denaturated sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination", "recombining" or generating a "recombined" nucleic acid is generally the assembly of two or more nucleic acid fragments wherein the assembly gives rise to a chimeric gene.

As used herein, a "flanking sequence" refers to any sequence that is either upstream or downstream of the sequence being discussed (e.g., for genes A-B-C, gene B is flanked by the A and C gene sequences). In certain embodiments, the incoming sequence is flanked by a homology box on each side. In another embodiment, the incoming sequence and the homology boxes comprise a unit that is flanked by stuffer sequence on each side. In some embodiments, a flanking sequence is present on only a single side (either 3' or 5'), but in preferred embodiments, it is on each side of the sequence being flanked. The sequence of each homology box is homologous to a sequence in the *Bacillus* chromosome. These sequences direct where in the *Bacillus* chromosome the new construct gets integrated and what part of the *Bacillus* chromosome will be replaced by the incoming sequence. In other embodiments, the 5' and 3' ends of a selective marker are flanked by a polynucleotide sequence comprising a section of the inactivating chromosomal segment. In some embodiments, a flanking sequence is present on only a single side (either 3' or 5'), while in other embodiments, it is present on each side of the sequence being flanked.

As used herein, the term "stuffer sequence" refers to any extra DNA that flanks homology boxes (typically vector sequences). However, the term encompasses any non-homologous DNA sequence. Not to be limited by any theory, a stuffer sequence provides a non-critical target for a cell to initiate DNA uptake.

II. GlcT Antitermination Protein

As described below in the Examples section, Applicant performed routine whole host mutagenesis (NTG) to create a pool of *B. licheniformis* mutants (i.e., modified *B. licheniformis* daughter cells) and used routine screening procedures to identify such modified *B. licheniformis* daughter cells capable of producing increased amounts of industrially relevant proteins of interest (e.g., heterologous enzymes, endogenous enzymes). More particularly, Applicant identified a modified *Bacillus licheniformis* (daughter) cell comprising a single nucleotide polymorphism (SNP) in a gene encoding a variant GlcT protein, which modified *B. licheniformis* (daughter) cell was capable of producing increased amounts of amylase protein, relative to a parental *B. licheniformis* cell comprising a gene encoding a wild-type GlcT protein (i.e., when the modified and parental *B. licheniformis* cells are cultivated under similar conditions).

As generally described in Schmalisch et al. (2003), the *Bacillus subtilis* GlcT protein is a member of the BglG family of transcriptional anti-terminators, which anti-terminators comprise an N-terminal RNA binding domain (about 60 amino acids), and two reiterated phosphotransferase system (PTS) regulation domains (PRDs; PRD-I and PRD-II), that modulate the regulatory output of the protein in response to the availability of the inducer (Manival et al., 1997; Stulke et al., 1998). For example, in *Escherichia coli, Bacillus subtilis*, and several other bacteria, glucose is taken up and concomitantly phosphorylated by the phosphoenolpyruvate: sugar phosphotransferase system (PTS) (Postma et al., 1993). The phosphotransferase system (PTS) is made up of two general energy-coupling proteins, Enzyme I (EI) and HPr, and several multi-domain sugar specific permeases (e.g., Enzyme II, (EII)), which may exist as individual proteins or fused in a single polypeptide.

For example, in *B. subtilis*, all domains of the glucose permease (EII) are fused to form a single polypeptide, with the domain arrangement (EIIC)-(EIIB)-(EIIA) (e.g., see, Postma et al., 1993; Stulke and Hillen, 2000). Furthermore, it was long considered that the genes encoding the components of the glucose PTS are constitutively expressed in bacteria. Although this is the case for the ptsI and ptsH genes encoding the general proteins, the ptsG gene encoding the glucose-specific permease ($EII^{Glc}$) is induced by glucose in both *E. coli* and *B. subtilis* (Postma et al., 1993; Stulke and Hillen, 2000; Plumbridge, 2002.) In *B. subtilis*, glucose induction of ptsG expression is mediated by transcriptional anti-termination. For example, in the absence of glucose, transcription initiated at the ptsG promoter is terminated in the leader region of the mRNA. If glucose is present, the GlcT anti-termination protein is active (i.e., a dimer), and prevents transcription termination by binding to the RNA anti-terminator (RAT) sequence, which overlaps the terminator. The binding of GlcT to the RAT is thought to stabilize the RAT structure and to prevent formation of the terminator (Stulke et al., 1997; Langbein et al., 1999).

Without wishing to be bound by any particular theory, mechanism, or mode of action, Applicant surprisingly discovered that modified *B. licheniformis* (daughter) cells of the disclosure, comprising a gene or ORF thereof encoding a variant GlcT protein, were capable of producing increased amounts of industrially relevant proteins of interest. More particularly, Applicant identified a modified *Bacillus licheniformis* (daughter) cell comprising a single nucleotide polymorphism (SNP) in a gene encoding a variant GlcT protein, which modified *B. licheniformis* (daughter) cell was capable of producing increased amounts of amylase protein, relative to a parental *B. licheniformis* cell comprising a gene encoding a wild-type GlcT protein (i.e., when the modified and parental *B. licheniformis* cells are cultivated under identical conditions).

For example, FIG. 1A shows a nucleic acid sequence alignment of a parental *B. licheniformis* ORF (SEQ ID NO: 22) encoding a wild-type GlcT protein (SEQ ID NO: 82), relative to the modified *B. licheniformis* ORF (SEQ ID NO: 56) encoding the variant GlcT protein (SEQ ID NO: 55). As shown in FIG. 1A, the two aligned ORF sequences (SEQ ID NO: 22 vs. SEQ ID NO: 56), differ by a SNP at nucleotide position 199, wherein position 199 of SEQ ID NO: 22 comprises a cytosine (C) and position 199 of SEQ ID NO: 56 comprises a thymine (T) (e.g., see FIG. 1A black boxed nucleotides (C) and (T) at position 199). Similarly, FIG. 1B shows an alignment of the encoded wild-type GlcT protein (SEQ ID NO: 82) and the encoded variant GlcT protein (SEQ ID NO: 55), wherein the (C) to (T) SNP at position 199 of SEQ ID NO: 56 (see, FIG. 1A), results in a leucine (L) to phenylalanine (F) substitution at amino acid residue position 67 of SEQ ID NO: 55 (e.g., see FIG. 1B, black boxed (L) and (F) amino acids at residue position 67 of SEQ ID NO: 22 and SEQ ID NO: 55, respectively).

Applicant further performed a BLAST protein sequence search, alignment and analysis thereof using the wild-type GlcT protein sequence of SEQ ID NO: 82, which analysis revealed that the leucine (L) amino acid at position 67 of SEQ ID NO: 82 is highly conserved among *Bacillus* sp. cells. Likewise, the sequence identity of the full length GlcT protein sequence is highly conserved (e.g., 80-100% amino acid sequence identity) among *Bacillus* sp. cells. Thus, in certain embodiments, allele glcT1 encodes a GlcT protein comprising about 90%, 91%, 92%, 93%, 94%, 95%, 96%, 97%, 98% or 99% sequence identity to SEQ ID NO: 55 and comprises a phenylalanine (F) at amino acid residue position 67 of SEQ ID NO: 55.

III. RghR2$_{rest}$ *B. licheniformis* Cells

As generally set forth above in Section II, certain embodiments of the disclosure are related to modified *Bacillus* (host) cells (i.e., comprising a modified glcT gene encoding a variant GlcT protein, e.g., comprising a phenylalanine (F) at amino acid position 67 (F67) of SEQ ID NO: 55), wherein the modified cells produce an increased amount of a protein of interest (POI) relative to a parental *Bacillus* cell producing the same POI. In certain related embodiments, a modified *Bacillus* cell of the disclosure is a modified *B. licheniformis* cell, comprising a restored rghR2 gene (rghR2$_{rest}$) described and set forth in U.S. Provisional Patent Application Ser. No. 62/463,268.

For example, in certain embodiments of the instant disclosure, a modified *Bacillus licheniformis* cell comprises a restored rghR2 gene comprising 90% sequence identity to the rghR2 gene of SEQ ID NO: 61. In other embodiments, a modified *B. licheniformis* cell comprises a restored rghR2 gene comprising 95% sequence identity to the rghR2 gene of SEQ ID NO: 61. In yet other embodiments, a modified *B. licheniformis* cell comprises a restored rghR2 gene of SEQ ID NO: 61.

In other embodiments, a modified *B. licheniformis* cell comprises a restored rghR2 gene encoding a RghR2 protein comprising 90% sequence identity to the RghR2 protein of SEQ ID NO: 84. In certain other embodiments, a modified *B. licheniformis* cell comprises a restored rghR2 gene encoding a RghR2 protein comprising 95% sequence identity to the RghR2 protein of SEQ ID NO: 84. In yet other embodiments, a modified *B. licheniformis* cell comprises a restored rghR2 gene encoding a RghR2 protein of SEQ ID NO: 84. Thus, certain embodiments of the disclosure are related to modified *B. licheniformis* cells comprising a restored rghR2 (rghR2$_{rest}$) gene and allele glcT1.

IV. Modified *B. subtilis* aprE 5'-UTR Nucleic Acid Sequences

As generally set forth above, certain embodiments the disclosure are related to modified *Bacillus* (host) cells comprising allele glcT1 wherein the modified *Bacillus* cells are capable of producing increased amounts of endogenous and/or heterologous proteins of interest relative to a parental *Bacillus* cell comprising a native/wild-type glcT gene. Thus, in certain related embodiments, the *Bacillus* parental cell and modified daughter cells thereof (e.g., comprising allele glcT1) are transformed with an expression construct encoding a protein of interest. For example, in certain embodiments, parental and modified *Bacillus* cells are transformed with an expression construct encoding a POI (e.g., an amylase, a protease, a lipase, etc.).

Thus, in certain related embodiments, a nucleic acid sequence (e.g., an ORF) encoding a POI is operably linked to a modified *B. subtilis* aprE 5'-untranslated region (mod-5'-UTR) sequence (SEQ ID NO: 63). For example, Applicant's U.S. Provisional Patent Application Ser. No. 62/558,304, filed Sep. 13, 2017 (incorporated herein by reference in its entirety) discloses and fully describes such mod-5'-UTR sequences, vectors thereof, modified host cells thereof and the like.

More particularly, as presented in Example 7 of the instant disclosure, Applicant tested the effect of a modified aprE 5' untranslated region (mod-5'-UTR) sequence on expression of genes encoding proteins of interest in *Bacillus* cells, (e.g., by constructing α-amylase expression cassettes comprising either the wild-type *B. subtilis* aprE 5'-UTR (SEQ ID NO: 62) or a modified aprE 5'-UTR (SEQ ID NO: 63). Thus, the Example 7 describes the creation of *Bacillus* host cells for the assessment of various (modified) 5'-UTR constructs, and their impact/influence on the production of proteins of interest when such modified 5'-UTR constructs are operably linked to an upstream (5') promoter and a downstream (3') open reading frame encoding the protein of interest.

For example, parental and modified *B. licheniformis* (daughter) cells BF63, BF62, and BF169 (see, Table 17 and Table 18), comprising a plasmid (pBL.ComK) carrying a xylose-inducible comK expression cassette (SEQ ID NO: 50) were constructed. More particularly, as described in the Examples section below, either the wild-type (WT) 5'-UTR expression construct (SEQ ID NO: 64) or the modified 5'-UTR expression construct (SEQ ID NO: 65) were constructed and tested, wherein each expression cassette (i.e., SEQ ID NO: 64 or SEQ ID NO: 65) comprised (in the 5' to 3' direction) the same 5' catH homology arm (SEQ ID NO: 66), catH gene (SEQ ID NO: 67) and spoVGrrnIp hybrid promoter (SEQ ID NO: 68), operably linked to either the WT-5'-UTR (SEQ ID NO: 62) or the mod-5'-UTR (SEQ ID NO: 63). In addition, the 5'-UTR was operably linked to the DNA encoding the lat signal sequence (SEQ ID NO: 69), followed by DNA (ORF) encoding a variant *G. stearothermophilus* α-amylase (SEQ ID NO: 70). The 3' end of the DNA (ORF) encoding the variant *G. stearothermophilus* α-amylase (SEQ ID NO: 70), was operably linked to the lat terminator (SEQ ID NO: 71), which was operably linked to the 3' catH homology arm (SEQ ID NO: 72).

V. Molecular Biology

As generally set forth above, certain embodiments of the disclosure are related to modified *Bacillus* (daughter) cells derived from parental *Bacillus* cells. More particularly, certain embodiments of the disclosure are related to modified *Bacillus* (daughter) cells and methods thereof for producing and constructing such modified *Bacillus* (host) cells (e.g., protein production host cells, cell factories) having increased protein production capabilities, increased secondary metabolite production capabilities and the like.

More specifically, certain embodiments of the disclosure are directed to mutants of a parental *Bacillus* cell comprising a glcT gene encoding a variant GlcT protein comprising a phenylalanine (F) at amino acid position 67 (F67) of SEQ ID NO: 55. Certain other embodiments of the disclosure are related to modified *Bacillus* cells derived from parental *Bacillus* cells comprising a wild-type glcT gene encoding a GlcT protein comprising a leucine (L) at amino acid position 67 (F67) of SEQ ID NO: 82, wherein the modified *Bacillus* cells comprise an edited (modified) glcT gene encoding a variant GlcT protein of SEQ ID NO: 55. Certain other embodiments are related to modified *Bacillus* (daughter) cells comprising an introduced polynucleotide encoding a variant GlcT protein comprising of SEQ ID NO: 55, comprising a phenylalanine (F) at amino acid position 67 (F67) of SEQ ID NO: 55. In other embodiments, modified *Bacillus* cells of the disclosure comprise an inactivated (endogenous) native chromosomal glcT gene (i.e., encoding a GlcT protein comprising at least 95% sequence identity to SEQ ID NO: 82 and comprising a leucine (L) at amino acid position 67 (L67) of SEQ ID NO: 55).

In certain other embodiments, a modified *Bacillus licheniformis* cell of the disclosure comprising and expressing a polynucleotide encoding a variant GlcT protein, further comprises a modification of an rghR2 gene which encodes a RghR2 protein comprising 90% sequence identity to SEQ ID NO: 84. In other embodiments the disclosure is related to modified *B. licheniformis* cells derived from parental *B. licheniformis* cells comprising a rghR2 gene encoding a RghR2 protein of SEQ ID NO: 83, wherein the modified cells comprise a restored rghR2 gene encoding a RghR2 protein of SEQ ID NO: 84.

Thus, certain embodiments of the disclosure provide compositions and methods for genetically modifying (altering) a parental *Bacillus* cell of the disclosure to generate modified *Bacillus* cells thereof, and more particularly, modified *Bacillus* cells which produce an increased amount of endogenous and/or heterologous proteins of interest relative to (unmodified) parental *B. licheniformis* cells.

Thus, certain embodiments of the disclosure are directed to methods for genetically modifying *Bacillus* cells, wherein the modification comprises (a) the introduction, substitution, or removal of one or more nucleotides in a gene (or an ORF thereof), or the introduction, substitution, or removal of one or more nucleotides in a regulatory element required for the transcription or translation of the gene or ORF thereof, (b) a gene disruption, (c) a gene conversion, (d) a gene deletion, (e) a gene down-regulation, (f) site specific mutagenesis and/or (g) random mutagenesis.

In certain embodiments, a modified *Bacillus* cell of the disclosure is constructed by reducing or eliminating the expression of a gene set forth above, using methods well known in the art, for example, insertions, disruptions, replacements, or deletions. The portion of the gene to be modified or inactivated may be, for example, the coding region or a regulatory element required for expression of the coding region. An example of such a regulatory or control sequence may be a promoter sequence or a functional part thereof, (i.e., a part which is sufficient for affecting expression of the nucleic acid sequence). Other control sequences for modification include, but are not limited to, a leader sequence, a pro-peptide sequence, a signal sequence, a transcription terminator, a transcriptional activator and the like.

In certain other embodiments a modified *Bacillus* cell is constructed by gene deletion to eliminate or reduce the expression of at least one of the aforementioned genes of the disclosure. Gene deletion techniques enable the partial or complete removal of the gene(s), thereby eliminating their expression, or expressing a non-functional (or reduced activity) protein product. In such methods, the deletion of the gene(s) may be accomplished by homologous recombination using a plasmid that has been constructed to contiguously contain the 5' and 3' regions flanking the gene. The contiguous 5' and 3' regions may be introduced into a *Bacillus* cell, for example, on a temperature-sensitive plasmid, such as pE194, in association with a second selectable marker at a permissive temperature to allow the plasmid to become established in the cell. The cell is then shifted to a non-permissive temperature to select for cells that have the plasmid integrated into the chromosome at one of the homologous flanking regions. Selection for integration of the plasmid is effected by selection for the second selectable marker. After integration, a recombination event at the second homologous flanking region is stimulated by shifting the cells to the permissive temperature for several generations without selection. The cells are plated to obtain single colonies and the colonies are examined for loss of both selectable markers (see, e.g., Perego, 1993). Thus, a person of skill in the art may readily identify nucleotide regions in the gene's coding sequence and/or the gene's non-coding sequence suitable for complete or partial deletion.

In other embodiments, a modified *Bacillus* cell of the disclosure is constructed by introducing, substituting, or removing one or more nucleotides in the gene or a regulatory element required for the transcription or translation thereof. For example, nucleotides may be inserted or removed so as to result in the introduction of a stop codon, the removal of the start codon, or a frame-shift of the open reading frame. Such a modification may be accomplished by site-directed mutagenesis or PCR generated mutagenesis in accordance with methods known in the art (e.g., see, Botstein and Shortie, 1985; Lo et al., 1985; Higuchi et al., 1988; Shimada, 1996; Ho et al., 1989; Horton et al., 1989 and Sarkar and Sommer, 1990). Thus, in certain embodiments, a gene of the disclosure is inactivated by complete or partial deletion.

In another embodiment, a modified *Bacillus* cell is constructed by the process of gene conversion (e.g., see Iglesias and Trautner, 1983). For example, in the gene conversion method, a nucleic acid sequence corresponding to the gene(s) is mutagenized in vitro to produce a defective nucleic acid sequence, which is then transformed into the parental *Bacillus* cell to produce a defective gene. By homologous recombination, the defective nucleic acid sequence replaces the endogenous gene. It may be desirable that the defective gene or gene fragment also encodes a marker which may be used for selection of transformants containing the defective gene. For example, the defective gene may be introduced on a non-replicating or temperature-sensitive plasmid in association with a selectable marker. Selection for integration of the plasmid is effected by selection for the marker under conditions not permitting plasmid replication. Selection for a second recombination event leading to gene replacement is effected by examination of colonies for loss of the selectable marker and acquisition of the mutated gene (Perego, 1993). Alternatively, the defective nucleic acid sequence may contain an insertion, substitution, or deletion of one or more nucleotides of the gene, as described below.

In other embodiments, a modified *Bacillus* cell is constructed by established anti-sense techniques using a nucleotide sequence complementary to the nucleic acid sequence of the gene (Parish and Stoker, 1997). More specifically, expression of the gene by a *Bacillus* cell may be reduced (down-regulated) or eliminated by introducing a nucleotide sequence complementary to the nucleic acid sequence of the gene, which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated. Such anti-sense methods include, but are not limited to RNA interference (RNAi), small interfering RNA (siRNA), microRNA (miRNA), antisense oligonucleotides, and the like, all of which are well known to the skilled artisan.

In other embodiments, a modified *Bacillus* cell is produced/constructed via CRISPR-Cas9 editing. For example, a gene encoding a GlcT protein can be edited or disrupted (or deleted or down-regulated) by means of nucleic acid guided endonucleases, that find their target DNA by binding either a guide RNA (e.g., Cas9) and Cpf1 or a guide DNA (e.g., NgAgo), which recruits the endonuclease to the target sequence on the DNA, wherein the endonuclease can generate a single or double stranded break in the DNA. This targeted DNA break becomes a substrate for DNA repair, and can recombine with a provided editing template to disrupt or delete the gene. For example, the gene encoding the nucleic acid guided endonuclease (for this purpose Cas9 from *S. pyogenes*) or a codon optimized gene encoding the Cas9 nuclease is operably linked to a promoter active in the *Bacillus* cell and a terminator active in *Bacillus* cell, thereby creating a *Bacillus* Cas9 expression cassette. Likewise, one or more target sites unique to the gene of interest are readily identified by a person skilled in the art. For example, to build a DNA construct encoding a gRNA-directed to a target site within the gene of interest, the variable targeting domain (VT) will comprise nucleotides of the target site which are 5' of the (PAM) proto-spacer adjacent motif (TGG), which nucleotides are fused to DNA encoding the Cas9 endonuclease recognition domain for *S. pyogenes* Cas9 (CER). The combination of the DNA encoding a VT domain and the DNA encoding the CER domain thereby generate a DNA encoding a gRNA. Thus, a *Bacillus* expression cassette for the gRNA is created by operably linking the DNA encoding the gRNA to a promoter active in *Bacillus* cells and a terminator active in *Bacillus* cells.

In certain embodiments, the DNA break induced by the endonuclease is repaired/replaced with an incoming sequence. For example, to precisely repair the DNA break generated by the Cas9 expression cassette and the gRNA expression cassette described above, a nucleotide editing template is provided, such that the DNA repair machinery of the cell can utilize the editing template. For example, about 500 bp 5' of targeted gene can be fused to about 500 bp 3' of the targeted gene to generate an editing template, which template is used by the *Bacillus* host's machinery to repair the DNA break generated by the RGEN.

The Cas9 expression cassette, the gRNA expression cassette and the editing template can be co-delivered to filamentous fungal cells using many different methods (e.g., protoplast fusion, electroporation, natural competence, or induced competence). The transformed cells are screened by PCR amplifying the target gene locus, by amplifying the locus with a forward and reverse primer. These primers can amplify the wild-type locus or the modified locus that has been edited by the RGEN. These fragments are then sequenced using a sequencing primer to identify edited colonies.

In yet other embodiments, a modified *Bacillus* cell is constructed by random or specific mutagenesis using methods well known in the art, including, but not limited to, chemical mutagenesis (see, e.g., Hopwood, 1970) and transposition (see, e.g., Youngman et al., 1983). Modification of the gene may be performed by subjecting the parental cell to mutagenesis and screening for mutant cells in which expression of the gene has been reduced or eliminated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosoguanidine (NTG), O-methyl hydroxylamine, nitrous acid, ethyl methane sulphonate (EMS), sodium bisulphite, formic acid, and nucleotide analogues. When such agents are used, the mutagenesis is typically performed by incubating the parental cell to be mutagenized in the presence of the mutagenizing agent of choice under suitable conditions, and selecting for mutant cells exhibiting reduced or no expression of the gene.

In certain other embodiments, a modified *Bacillus* cell comprises a deletion of an endogenous gene. In other embodiments, a modified *Bacillus* cell comprises a disruption of an endogenous gene. In certain embodiments, a polynucleotide disruption cassette of the disclosure comprises a marker gene.

In other embodiments, a modified *Bacillus* cell comprises a down-regulated endogenous gene. For example, in certain embodiments, down-regulating one or more genes set forth above comprises deleting or disrupting the gene's upstream or downstream regulatory elements.

PCT Publication No. WO2003/083125 discloses methods for modifying *Bacillus* cells, such as the creation of *Bacillus* deletion strains and DNA constructs using PCR fusion to bypass *E. coli*.

PCT Publication No. WO2002/14490 discloses methods for modifying *Bacillus* cells including (1) the construction and transformation of an integrative plasmid (pComK), (2) random mutagenesis of coding sequences, signal sequences and pro-peptide sequences, (3) homologous recombination, (4) increasing transformation efficiency by adding non-homologous flanks to the transformation DNA, (5) optimizing double cross-over integrations, (6) site directed mutagenesis and (7) marker-less deletion.

Those of skill in the art are well aware of suitable methods for introducing polynucleotide sequences into bacterial cells (e.g., *E. coli* and *Bacillus* spp.) (e.g., Ferrari et al., 1989; Saunders et al., 1984; Hoch et al., 1967; Mann et al., 1986; Holubova, 1985; Chang et al., 1979; Vorobjeva et al., 1980; Smith et al., 1986; Fisher et. al., 1981 and McDonald, 1984). Indeed, such methods as transformation including protoplast transformation and congression, transduction, and protoplast fusion are known and suited for use in the present disclosure. Methods of transformation are particularly preferred to introduce a DNA construct of the present disclosure into a host cell.

In addition to commonly used methods, in some embodiments, host cells are directly transformed (i.e., an intermediate cell is not used to amplify, or otherwise process, the DNA construct prior to introduction into the host cell). Introduction of the DNA construct into the host cell includes those physical and chemical methods known in the art to introduce DNA into a host cell, without insertion into a plasmid or vector. Such methods include, but are not limited to, calcium chloride precipitation, electroporation, naked DNA, liposomes and the like. In additional embodiments, DNA constructs are co-transformed with a plasmid without being inserted into the plasmid. In further embodiments, a selective marker is deleted or substantially excised from the modified *Bacillus* strain by methods known in the art (e.g., Stahl et al., 1984 and Palmeros et al., 2000). In some embodiments, resolution of the vector from a host chromosome leaves the flanking regions in the chromosome, while removing the indigenous chromosomal region.

Promoters and promoter sequence regions for use in the expression of genes, open reading frames (ORFs) thereof and/or variant sequences thereof in *Bacillus* cells are generally known on one of skill in the art. Promoter sequences of the disclosure of the disclosure are generally chosen so that they are functional in the *Bacillus* cells (e.g., *B. licheniformis* cells, *B. subtilis* cells and the like). Certain exemplary *Bacillus* promoter sequences are presented in Table 6. Likewise, promoters useful for driving gene expression in *Bacillus* cells include, but are not limited to, the *B. subtilis* alkaline protease (aprE) promoter (Stahl et al., 1984), the α-amylase promoter of *B. subtilis* (Yang et al., 1983), the α-amylase promoter of *B. amyloliquefaciens* (Tarkinen et al., 1983), the neutral protease (nprE) promoter from *B. subtilis* (Yang et al., 1984), a mutant aprE promoter (PCT Publication No. WO2001/51643) or any other promoter from *B. licheniformis* or other related Bacilli. In certain other embodiments, the promoter is a ribosomal protein promoter or a ribosomal RNA promoter (e.g., the rrnI promoter) disclosed in U.S. Patent Publication No. 2014/0329309. Methods for screening and creating promoter libraries with a range of activities (promoter strength) in *Bacillus* cells is describe in PCT Publication No. WO2003/089604.

VI. Culturing *Bacillus* Cells for Production of a Protein of Interest

In other embodiments, the present disclosure provides methods for increasing the protein productivity of a modified bacterial cell, as compared (i.e., relative) to an unmodified (parental) cell. In certain embodiments, the instant disclosure is directed to methods of producing a protein of interest (POI) comprising fermenting/cultivating a modified bacterial cell, wherein the modified cell secrets the POI into the culture medium. Fermentation methods well known in the art can be applied to ferment the modified and unmodified *Bacillus* cells of the disclosure.

In some embodiments, the cells are cultured under batch or continuous fermentation conditions. A classical batch fermentation is a closed system, where the composition of the medium is set at the beginning of the fermentation and is not altered during the fermentation. At the beginning of the fermentation, the medium is inoculated with the desired organism(s). In this method, fermentation is permitted to occur without the addition of any components to the system. Typically, a batch fermentation qualifies as a "batch" with respect to the addition of the carbon source, and attempts are often made to control factors such as pH and oxygen concentration. The metabolite and biomass compositions of the batch system change constantly up to the time the fermentation is stopped. Within typical batch cultures, cells can progress through a static lag phase to a high growth log phase, and finally to a stationary phase, where growth rate is diminished or halted. If untreated, cells in the stationary phase eventually die. In general, cells in log phase are responsible for the bulk of production of product.

A suitable variation on the standard batch system is the "fed-batch fermentation" system. In this variation of a typical batch system, the substrate is added in increments as the fermentation progresses. Fed-batch systems are useful when catabolite repression likely inhibits the metabolism of the cells and where it is desirable to have limited amounts of substrate in the medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are common and known in the art.

Continuous fermentation is an open system where a defined fermentation medium is added continuously to a bioreactor, and an equal amount of conditioned medium is removed simultaneously for processing. Continuous fermentation generally maintains the cultures at a constant high density, where cells are primarily in log phase growth. Continuous fermentation allows for the modulation of one or more factors that affect cell growth and/or product concentration. For example, in one embodiment, a limiting nutrient, such as the carbon source or nitrogen source, is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

Thus, in certain embodiments, a POI produced by a transformed (modified) host cell may be recovered from the culture medium by conventional procedures including separating the host cells from the medium by centrifugation or filtration, or if necessary, disrupting the cells and removing the supernatant from the cellular fraction and debris. Typically, after clarification, the proteinaceous components of the supernatant or filtrate are precipitated by means of a salt, e.g., ammonium sulfate. The precipitated proteins are then solubilized and may be purified by a variety of chromatographic procedures, e.g., ion exchange chromatography, gel filtration.

VII. Proteins of Interest Produced by Modified (Host) Cells

A protein of interest (POI) of the instant disclosure can be any endogenous or heterologous protein, and it may be a variant of such a POI. The protein can contain one or more disulfide bridges or is a protein whose functional form is a monomer or a multimer, i.e., the protein has a quaternary structure and is composed of a plurality of identical (homologous) or non-identical (heterologous) subunits, wherein the POI or a variant POI thereof is preferably one with properties of interest.

For example, as set forth in the Examples below, the modified *Bacillus* cells of the disclosure produce an increased amount of endogenous and/or heterologous proteins of interests. Thus, in certain embodiments, a modified cell of the disclosure expresses an endogenous POI, a heterologous POI or a combination of one or more of such POIs. For example, in certain embodiments, a modified *Bacillus* (daughter) cell of the disclosure produces an increased amount of an endogenous POI relative to a parental *Bacillus* cell. In other embodiments, a modified *Bacillus* (daughter) cell of the disclosure produces an increased amount of a heterologous POI relative to a parental *Bacillus* cell.

Thus, in certain embodiments, a modified *Bacillus* (daughter) cell of the disclosure produces an increased amount of a POI relative to a parental *Bacillus* (control) cell, wherein the increased amount of the POI is at least about a 0.01% increase, at least about a 0.10% increase, at least about a 0.50% increase, at least about a 1.0% increase, at least about a 2.0% increase, at least about a 3.0% increase, at least about a 4.0% increase, at least about a 5.0% increase, or an increase greater than 5.0%. In certain embodiments, the increased amount of the POI is determined by assaying enzymatic activity and/or by assaying/quantifying the specific productivity (Qp) thereof. Likewise, one skilled in the art may utilize other routine methods and techniques known in the art for detecting, assaying, measuring, etc. the expression or production of one or more proteins of interest.

In certain embodiments, a modified *Bacillus* cell of the disclosure exhibits an increased specific productivity (Qp) of a POI relative the (unmodified) parental *Bacillus* cell. For example, the detection of specific productivity (Qp) is a suitable method for evaluating protein production. The specific productivity (Qp) can be determined using the following equation:

$$\text{“}Qp=gP/g\text{DCW}\cdot hr\text{”}$$

wherein, “gP” is grams of protein produced in the tank; “gDCW” is grams of dry cell weight (DCW) in the tank and “hr” is fermentation time in hours from the time of inoculation, which includes the time of production as well as growth time.

Thus, in certain other embodiments, a modified *Bacillus* cell of the disclosure comprises a specific productivity (Qp) increase of at least about 0.1%, at least about 1%, at least about 5%, at least about 6%, at least about 7%, at least about 8%, at least about 9%, or at least about 10% or more as compared to the unmodified (parental) cell.

In certain embodiments, a POI or a variant POI thereof is selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, ligases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof.

Thus, in certain embodiments, a POI or a variant POI thereof is an enzyme selected from Enzyme Commission (EC) Number EC 1, EC 2, EC 3, EC 4, EC 5 or EC 6.

For example, in certain embodiments a POI is an oxidoreductase enzyme, including, but not limited to, an EC 1 (oxidoreductase) enzyme selected from EC 1.10.3.2 (e.g., a laccase), EC 1.10.3.3 (e.g., L-ascorbate oxidase), EC 1.1.1.1 (e.g., alcohol dehydrogenase), EC 1.11.1.10 (e.g., chloride peroxidase), EC 1.11.1.17 (e.g., peroxidase), EC 1.1.1.27 (e.g., L-lactate dehydrogenase), EC 1.1.1.47 (e.g., glucose 1-dehydrogenase), EC 1.1.3.X (e.g., glucose oxidase), EC 1.1.3.10 (e.g., pyranose oxidase), EC 1.13.11.X (e.g., dioxygenase), EC 1.13.11.12 (e.g., lineolate 13S-lipozygenase), EC 1.1.3.13 (e.g., alcohol oxidase), EC 1.14.14.1 (e.g., monooxygenase), EC 1.14.18.1 (e.g., monophenol monooxigenase) EC 1.15.1.1 (e.g., superoxide dismutase), EC 1.1.5.9 (formerly EC 1.1.99.10, e.g., glucose dehydrogenase), EC 1.1.99.18 (e.g., cellobiose dehydrogenase), EC 1.1.99.29 (e.g., pyranose dehydrogenase), EC 1.2.1.X (e.g., fatty acid reductase), EC 1.2.1.10 (e.g., acetaldehyde dehydrogenase), EC 1.5.3.X (e.g., fructosyl amine reductase), EC 1.8.1.X (e.g., disulfide reductase) and EC 1.8.3.2 (e.g., thiol oxidase).

In certain embodiments a POI is a transferase enzyme, including, but not limited to, an EC 2 (transferase) enzyme selected from EC 2.3.2.13 (e.g., transglutaminase), EC 2.4.1.X (e.g., hexosyltransferase), EC 2.4.1.40 (e.g., alternasucrase), EC 2.4.1.18 (e.g., 1,4 alpha-glucan branching enzyme), EC 2.4.1.19 (e.g., cyclomaltodextrin glucanotransferase), EC 2.4.1.2 (e.g., dextrin dextranase), EC 2.4.1.20 (e.g., cellobiose phosphorylase), EC 2.4.1.25 (e.g., 4-alpha-glucanotransferase), EC 2.4.1.333 (e.g., 1,2-beta-oligoglucan phosphor transferase), EC 2.4.1.4 (e.g., amylosucrase), EC 2.4.1.5 (e.g., dextransucrase), EC 2.4.1.69 (e.g., galactoside 2-alpha-L-fucosyl transferase), EC 2.4.1.9 (e.g., inulosucrase), EC 2.7.1.17 (e.g., xylulokinase), EC 2.7.7.89 (formerly EC 3.1.4.15, e.g., [glutamine synthetase]-adenylyl-L-tyrosine phosphorylase), EC 2.7.9.4 (e.g., alpha glucan kinase) and EC 2.7.9.5 (e.g., phosphoglucan kinase).

In other embodiments a POI is a hydrolase enzyme, including, but not limited to, an EC 3 (hydrolase) enzyme selected from EC 3.1.X.X (e.g., an esterase), EC 3.1.1.1 (e.g., pectinase), EC 3.1.1.14 (e.g., chlorophyllase), EC 3.1.1.20 (e.g., tannase), EC 3.1.1.23 (e.g., glycerol-ester acylhydrolase), EC 3.1.1.26 (e.g., galactolipase), EC 3.1.1.32 (e.g., phospholipase A1), EC 3.1.1.4 (e.g., phospholipase A2), EC 3.1.1.6 (e.g., acetylesterase), EC 3.1.1.72 (e.g., acetylxylan esterase), EC 3.1.1.73 (e.g., feruloyl esterase), EC 3.1.1.74 (e.g., cutinase), EC 3.1.1.86 (e.g., rhamnogalacturonan acetylesterase), EC 3.1.1.87 (e.g., fumosin B1 esterase), EC 3.1.26.5 (e.g., ribonuclease P), EC 3.1.3.X (e.g., phosphoric monoester hydrolase), EC 3.1.30.1 (e.g., *Aspergillus* nuclease S1), EC 3.1.30.2 (e.g., *Serratia marcescens* nuclease), EC 3.1.3.1 (e.g., alkaline phosphatase), EC 3.1.3.2 (e.g., acid phosphatase), EC 3.1.3.8 (e.g., 3-phytase), EC 3.1.4.1 (e.g., phosphodiesterase I), EC 3.1.4.11 (e.g., phosphoinositide phospholipase C), EC 3.1.4.3 (e.g., phospholipase C), EC 3.1.4.4 (e.g., phospholipase D), EC 3.1.6.1 (e.g., arylsufatase), EC 3.1.8.2 (e.g., diisopropyl-fluorophosphatase), EC 3.2.1.10 (e.g., oligo-1, 6-glucosidase), EC 3.2.1.101 (e.g., mannan endo-1,6-alpha-mannosidase), EC 3.2.1.11 (e.g., alpha-1,6-glucan-6-glucanohydrolase), EC 3.2.1.131 (e.g., xylan alpha-1,2-glucuronosidase), EC 3.2.1.132 (e.g., chitosan N-acetylglucosaminohydrolase), EC 3.2.1.139 (e.g., alpha-glucuronidase), EC 3.2.1.14 (e.g., chitinase), EC 3.2.1.151 (e.g., xyloglucan-specific endo-beta-1,4-glucanase), EC 3.2.1.155 (e.g., xyloglucan-specific exo-beta-1,4-glucanase), EC 3.2.1.164 (e.g., galactan endo-1,6-beta-galactosidase), EC 3.2.1.17 (e.g., lysozyme), EC 3.2.1.171 (e.g., rhamnogalacturonan hydrolase), EC 3.2.1.174 (e.g., rhamnogalacturonan rhamnohydrolase), EC 3.2.1.2 (e.g., beta-amylase), EC 3.2.1.20 (e.g., alpha-glucosidase), EC 3.2.1.22 (e.g., alpha-galactosidase), EC 3.2.1.25 (e.g., beta-mannosidase), EC 3.2.1.26 (e.g., beta-fructofuranosidase), EC 3.2.1.37 (e.g., xylan 1,4-beta-xylosidase), EC 3.2.1.39 (e.g., glucan endo-1,3-beta-D-glucosidase), EC 3.2.1.40 (e.g., alpha-L-rhamnosidase), EC 3.2.1.51 (e.g., alpha-L-fucosidase), EC 3.2.1.52 (e.g., beta-N-Acetylhexosaminidase), EC 3.2.1.55 (e.g., alpha-N-arabinofuranosidase), EC 3.2.1.58 (e.g., glucan 1,3-beta-glucosidase), EC 3.2.1.59 (e.g., glucan endo-1,3-alpha-glucosidase), EC 3.2.1.67 (e.g., galacturan 1,4-alpha-galacturonidase), EC 3.2.1.68 (e.g., isoamylase), EC 3.2.1.7 (e.g., 1-beta-D-fructan fructanohydrolase), EC 3.2.1.74 (e.g., glucan 1,4-β-glucosidase), EC 3.2.1.75 (e.g., glucan endo-1,6-beta-glucosidase), EC 3.2.1.77 (e.g., mannan 1,2-(1,3)-alpha-mannosidase), EC 3.2.1.80 (e.g., fructan beta-fructosidase), EC 3.2.1.82 (e.g., exo-poly-alpha-galacturonosidase), EC 3.2.1.83 (e.g., kappa-carrageenase), EC 3.2.1.89 (e.g., arabinogalactan endo-1,4-beta-galactosidase), EC 3.2.1.91 (e.g., cellulose 1,4-beta-cellobiosidase), EC 3.2.1.96 (e.g., mannosyl-glycoprotein endo-beta-N-acetylglucosaminidase), EC 3.2.1.99 (e.g., arabinan endo-1,5-alpha-L-arabinanase), EC 3.4.X.X (e.g., peptidase), EC 3.4.11.X (e.g., aminopeptidase), EC 3.4.11.1 (e.g., leucyl aminopeptidase), EC 3.4.11.18 (e.g., methionyl aminopeptidase), EC 3.4.13.9 (e.g., Xaa-Pro dipeptidase), EC 3.4.14.5 (e.g., dipeptidyl-peptidase IV), EC 3.4.16.X (e.g., serine-type carboxypeptidase), EC 3.4.16.5 (e.g., carboxypeptidase C), EC 3.4.19.3 (e.g., pyroglutamyl-peptidase I), EC 3.4.21.X (e.g., serine endopeptidase), EC 3.4.21.1 (e.g., chymotrypsin), EC 3.4.21.19 (e.g., glutamyl endopeptidase), EC 3.4.21.26 (e.g., prolyl oligopeptidase), EC 3.4.21.4 (e.g., trypsin), EC 3.4.21.5 (e.g., thrombin), EC 3.4.21.63 (e.g., oryzin), EC 3.4.21.65 (e.g., thermomycolin), EC 3.4.21.80 (e.g., streptogrisin A), EC 3.4.22.X (e.g., cysteine endopeptidase), EC 3.4.22.14 (e.g., actinidain), EC 3.4.22.2 (e.g., papain), EC 3.4.22.3 (e.g., ficain), EC 3.4.22.32 (e.g., stem bromelain), EC 3.4.22.33 (e.g., fruit bromelain), EC 3.4.22.6 (e.g., chymopapain), EC 3.4.23.1 (e.g., pepsin A), EC 3.4.23.2 (e.g., pepsin B), EC 3.4.23.22 (e.g., endothiapepsin), EC 3.4.23.23 (e.g., mucorpepsin), EC 3.4.23.3 (e.g., gastricsin), EC 3.4.24.X (e.g., metalloendopeptidase), EC 3.4.24.39 (e.g., deuterolysin), EC 3.4.24.40 (e.g., serralysin), EC 3.5.1.1 (e.g., asparaginase), EC 3.5.1.11 (e.g., penicillin amidase), EC 3.5.1.14 (e.g., N-acyl-aliphatic-L-amino acid amidohydrolase), EC 3.5.1.2 (e.g., L-glutamine amidohydrolase), EC 3.5.1.28 (e.g., N-acetylmuramoyl-L-alanine amidase), EC 3.5.1.4 (e.g., amidase), EC 3.5.1.44 (e.g., protein-L-glutamine amidohydrolase), EC 3.5.1.5 (e.g., urease), EC 3.5.1.52 (e.g., peptide-N(4)-(N-acetyl-beta-glucosaminyl)asparagine amidase), EC 3.5.1.81 (e.g., N-Acyl-D-amino-acid deacylase), EC 3.5.4.6 (e.g., AMP deaminase) and EC 3.5.5.1 (e.g., nitrilase).

In other embodiments a POI is a lyase enzyme, including, but not limited to, an EC 4 (lyase) enzyme selected from EC 4.1.2.10 (e.g., mandelonitrile lyase), EC 4.1.3.3 (e.g., N-acetylneuraminate lyase), EC 4.2.1.1 (e.g., carbonate dehydratase), EC 4.2.2-(e.g., rhamnogalacturonan lyase), EC 4.2.2.10 (e.g., pectin lyase), EC 4.2.2.22 (e.g., pectate trisaccharide-lyase), EC 4.2.2.23 (e.g., rhamnogalacturonan endolyase) and EC 4.2.2.3 (e.g., mannuronate-specific alginate lyase).

In certain other embodiments a POI is an isomerase enzyme, including, but not limited to, an EC 5 (isomerase) enzyme selected from EC 5.1.3.3 (e.g., aldose 1-epimerase), EC 5.1.3.30 (e.g., D-psicose 3-epimerase), EC 5.4.99.11 (e.g., isomaltulose synthase) and EC 5.4.99.15 (e.g., (1→4)-α-D-glucan 1-α-D-glucosylmutase).

In yet other embodiments, a POI is a ligase enzyme, including, but not limited to, an EC 6 (ligase) enzyme selected from EC 6.2.1.12 (e.g., 4-coumarate:coenzyme A ligase) and EC 6.3.2.28 (e.g., L-amino-acid alpha-ligase)9

Thus, in certain embodiments, industrial protease producing *Bacillus* host cells provide particularly preferred expression hosts. Likewise, in certain other embodiments, industrial amylase producing *Bacillus* host cells provide particularly preferred expression hosts.

For example, there are two general types of proteases which are typically secreted by *Bacillus* spp., namely neutral (or "metalloproteases") and alkaline (or "serine") proteases. For example, *Bacillus* subtilisin proteins (enzymes) are exemplary serine proteases for use in the present disclosure. A wide variety of *Bacillus* subtilisins have been identified and sequenced, for example, subtilisin 168, subtilisin BPN', subtilisin Carlsberg, subtilisin DY, subtilisin 147 and subtilisin 309 (e.g., WO 1989/06279 and Stahl et al., 1984). In some embodiments of the present disclosure, the modified *Bacillus* cells produce mutant (i.e., variant) proteases. Numerous references provide examples of variant proteases, such as PCT Publication Nos. WO1999/20770; WO1999/20726; WO1999/20769; WO1989/06279; U.S. Pat. Nos. RE34,606; 4,914,031; 4,980,288; 5,208,158; 5,310,675; 5,336,611; 5,399,283; 5,441,882; 5,482,849; 5,631,217; 5,665,587; 5,700,676; 5,741,694; 5,858,757; 5,880,080; 6,197,567 and 6,218,165. Thus, in certain embodiments, a modified *Bacillus* cells of the disclosure comprises an expression construct encoding a protease.

In certain other embodiments, a modified *Bacillus* cells of the disclosure comprises an expression construct encoding an amylase. A wide variety of amylase enzymes and variants thereof are known to one skilled in the art. For example, International PCT Publication NO. WO2006/037484 and WO 2006/037483 describe variant α-amylases having improved solvent stability, Publication No. WO1994/18314 discloses oxidatively stable α-amylase variants, Publication No. WO1999/19467, WO2000/29560 and WO2000/60059 disclose Termamyl-like α-amylase variants, Publication No. WO2008/112459 discloses α-amylase variants derived from *Bacillus* sp. number 707, Publication No. WO1999/43794 discloses maltogenic α-amylase variants, Publication No. WO1990/11352 discloses hyper-thermostable α-amylase variants, Publication No. WO2006/089107 discloses α-amylase variants having granular starch hydrolyzing activity.

In other embodiments, a POI or variant POI expressed and produced in a modified cell of the disclosure is a peptide, a peptide hormone, a growth factor, a clotting factor, a chemokine, a cytokine, a lymphokine, an antibody, a receptor, an adhesion molecule, a microbial antigen (e.g., HBV surface antigen, HPV E7, etc.), variants thereof, fragments thereof and the like. Other types of proteins (or variants thereof) of interest may be those that are capable of providing nutritional value to a food or to a crop. Non-limiting examples include plant proteins that can inhibit the formation of anti-nutritive factors and plant proteins that have a more desirable amino acid composition (e.g., a higher lysine content than a non-transgenic plant).

There are various assays known to those of ordinary skill in the art for detecting and measuring activity of intracellularly and extracellularly expressed proteins. In particular, for proteases, there are assays based on the release of acid-soluble peptides from casein or hemoglobin measured as absorbance at 280 nm or colorimetrically, using the Folin method (e.g., Bergmeyer et al., 1984). Other assays involve the solubilization of chromogenic substrates (See e.g., Ward, 1983). Other exemplary assays include succinyl-Ala-Ala-Pro-Phe-para-nitroanilide assay (SAAPFpNA) and the 2,4,6-trinitrobenzene sulfonate sodium salt assay (TNBS assay). Numerous additional references known to those in the art provide suitable methods (See e.g., Wells et al., 1983; Christianson et al., 1994 and Hsia et al., 1999).

International PCT Publication No. WO2014/164777 discloses Ceralpha α-amylase activity assays useful for amylase activities described herein.

Means for determining the levels of secretion of a protein of interest in a host cell and detecting expressed proteins include the use of immunoassays with either polyclonal or monoclonal antibodies specific for the protein. Examples include enzyme-linked immunosorbent assay (ELISA), radioimmunoassay (RIA), fluorescence immunoassay (FIA), and fluorescent activated cell sorting (FACS).

EXAMPLES

Certain aspects of the present invention may be further understood in light of the following examples, which should not be construed as limiting. Modifications to materials and methods will be apparent to those skilled in the art.

Example 1

A Mutant *Bacillus licheniformis* Daughter Cell Comprising a Single Nucleotide Polymorphism (SNP) in a Gene Encoding a Variant GlcT Protein As briefly set forth above in the Detailed Description, Applicant of the present disclosure performed routine NTG (N-methyl-N'-nitro-N-nitrosoguanidine) mutagenesis to create a pool of *B. licheniformis* mutants (i.e., *B. licheniformis* daughter cells), which NTG modified daughter cells were subsequently screened to identify *B. licheniformis* daughter cell mutations that can increase the production of industrially relevant proteins of interest (e.g., an amylase, a protease, etc.). More specifically, via routine Ceralpha α-amylase assays, Applicant identified a mutant *B. licheniformis* (daughter) cell comprising a SNP in a gene encoding a variant GlcT protein (i.e., allele glcT1; SEQ ID NO: 56), which variant *B. licheniformis* cell was capable of producing increased amounts of heterologous amylase protein, relative to a parental *B. licheniformis* cell comprising a gene encoding a wild-type GlcT protein (e.g., see, Example 8 below), wherein the variant and parental cells are cultivated under identical conditions. The Ceralpha α-amylase assay, further described below in Example 8, generally involves incubating whole culture broth with a substrate mixture under defined conditions, wherein the reaction is terminated (and color developed) by the addition of a base solution (e.g., as described in PCT publication No. WO2014/164777).

Thus, as generally set forth above in the Detailed Description, a wild-type *B. licheniformis* glcT gene encodes a wild-type GlcT protein of SEQ ID NO: 82 (comprising a Leucine (L) at amino acid position 67 of SEQ ID NO: 82), which wild-type GlcT protein is a transcriptional anti-terminator protein (e.g., see, Schmalisch et al., 2003; Manival et al., 1997; Stulke et al., 1998; Postma et al., 1993; Stulke and Hillen, 2000; Plumbridge, 2002; Stulke et al., 1997 and Langbein et al., 1999). The mutant glcT gene (i.e., allele glcT1; SEQ ID NO: 56) encodes a variant GlcT protein of SEQ ID NO: 55, comprising a Leucine (L) to Phenylalanine (F) amino acid substitution at amino acid position 67 (F67; SEQ ID NO: 55; e.g., see FIG. 1A and FIG. 1B).

Example 2

Construction of GlcT Cas9 Targeting Vectors

A synthetic polynucleotide encoding the Cas9 protein from *S. pyogenes* (SEQ ID NO: 1), comprising an N-terminal nuclear localization sequence (NLS; "APKKKRKV"; SEQ ID NO: 2), a C-terminal NLS ("KKKKLK"; SEQ ID NO: 3) and a deca-histidine tag ("HHHHHHHHHH"; SEQ ID NO: 4), was operably linked to the aprE promoter from *B. subtilis* (SEQ ID NO: 5) and amplified using Q5 DNA polymerase (NEB) per manufacturer's instructions with the forward (SEQ ID NO: 6) and reverse (SEQ ID NO: 7) primer pair set forth below in Table 2.

TABLE 2

| FORWARD AND REVERSE PRIMER PAIR | | |
|---|---|---|
| Forward | ATATATGAGTAAACTTGGTCTGACAGAA TTCCTCCATTTTCTTCTGCTAT | SEQ ID NO: 6 |
| Reverse | TGCGGCCGCGAATTCGATTACGAATGCC GTCTCCC | SEQ ID NO: 7 |

The backbone (SEQ ID NO: 8) of plasmid pKB320 (SEQ ID NO: 9) was amplified using Q5 DNA polymerase (NEB) per manufacturer's instructions with the forward (SEQ ID NO: 10) and reverse (SEQ ID NO: 11) primer pair set forth below in Table 3.

TABLE 3

| FORWARD AND REVERSE PRIMER PAIR | | |
|---|---|---|
| Forward | GGGAGACGGCATTCGTAATCGAATTCGCG GCCGCA | SEQ ID NO: 10 |
| Reverse | ATAGCAGAAGAAAATGGAGGAATTCTGTC AGACCAAGTTTACTCATATAT | SEQ ID NO: 11 |

The PCR products were purified using Zymo clean and concentrate 5 columns per manufacturer's instructions. Subsequently, the PCR products were assembled using prolonged overlap extension PCR (POE-PCR) with Q5 Polymerase (NEB) mixing the two fragments at equimolar ratio. The POE-PCR reactions were cycled: 98° C. for five (5) seconds, 64° C. for ten (10) seconds, 72° C. for four (4) minutes and fifteen (15) seconds for 30 cycles. Five (5) μl of the POE-PCR (DNA) was transformed into Top10 *E. coli* (Invitrogen) per manufacturer's instructions and selected on lysogeny (L) Broth (Miller recipe; 1% (w/v) Tryptone, 0.5% Yeast extract (w/v), 1% NaCl (w/v)), containing fifty (50) μg/ml kanamycin sulfate and solidified with 1.5% Agar. Colonies were allowed to grow for eighteen (18) hours at 37° C. Colonies were picked and plasmid DNA prepared using Qiaprep DNA miniprep kit per manufacturer's instructions and eluted in fifty-five (55) μl of $ddH_2O$. The plasmid DNA was Sanger sequenced to verify correct assembly, using the sequencing primers (SEQ ID NOs: 12-20) set forth below in Table 4.

TABLE 4

| SEQUENCING PRIMERS | | |
|---|---|---|
| Reverse | CCGACTGGAGCTCCTATATTACC | SEQ ID NO: 12 |
| Reverse | GCTGTGGCGATCTGTATTCC | SEQ ID NO: 13 |
| Forward | GTCTTTTAAGTAAGTCTACTCT | SEQ ID NO: 14 |
| Forward | CCAAAGCGATTTTAAGCGCG | SEQ ID NO: 15 |
| Forward | CCTGGCACGTGGTAATTCTC | SEQ ID NO: 16 |
| Forward | GGATTTCCTCAAATCTGACG | SEQ ID NO: 17 |
| Forward | GTAGAAACGCGCCAAATTACG | SEQ ID NO: 18 |
| Forward | GCTGGTGGTTGCTAAAGTCG | SEQ ID NO: 19 |
| Forward | GGACGCAACCCTCATTCATC | SEQ ID NO: 20 |

The correctly assembled plasmid, pRF694 (SEQ ID NO: 21), was used to assemble the plasmid for the introduction of the L67F glcT mutation. More particularly, the glcT gene (SEQ ID NO: 22) of *B. licheniformis* contains a Cas9 target site that overlays the L67 codon (SEQ ID NO: 23). The target site can be converted into a DNA sequence encoding a variable targeting (VT) domain (SEQ ID NO: 24) by removing the PAM sequence (SEQ ID NO: 25). The DNA sequence encoding the VT domain (SEQ ID NO: 24) can be operably fused to the DNA sequence encoding the Cas9 Endonuclease Recognition domain (CER; SEQ ID NO: 26) such that when transcribed by RNA polymerase in the cell, it produces a functional gRNA (SEQ ID NO: 27). The DNA encoding the gRNA (SEQ ID NO: 28) can be operably linked to a promoter operable in *Bacillus* sp. cells (e.g., the rrnIp2 promoter from *B. subtilis*; SEQ ID NO: 29) and a terminator operable in *Bacillus* sp. cells (e.g., the t0 terminator of lambda phage; SEQ ID NO: 30), such that the promoter is positioned 5' of the DNA encoding the gRNA and the terminator is positioned 3' of the DNA encoding the gRNA, to create a gRNA expression cassette (SEQ ID NO: 31).

An editing template for creating the L67F mutation in glcT can be amplified from *B. licheniformis* genomic DNA (gDNA) by creating two fragments. First, the 500 bp upstream (5') of the first position of codon 67 of glcT (SEQ ID NO: 32) was amplified using Q5 DNA polymerase according to the manufacturer's instructions and the forward (SEQ ID NO: 33) and reverse (SEQ ID NO: 34) primer pair set forth below in Table 5, wherein the reverse primer in this case contains a change to the first position of codon 67 from CTC to TTC converting codon 67 from a Leucine to a Phenylalanine.

TABLE 5

| FORWARD AND REVERSE PRIMER PAIR | | |
|---|---|---|
| Forward | TGAGTAAACTTGGTCTGACATAAGC TGTGACAACCAGC | SEQ ID NO: 33 |
| Reverse | CCATTTTTTCATCGACATAAGTGAA GAGCTTCTTATACTGCGATT | SEQ ID NO: 34 |

A second fragment containing the 500 bp downstream (3') of the first position of codon 67 of glcT (SEQ ID NO: 35) was amplified from *B. licheniformis* gDNA using Q5 DNA polymerase according to the manufacturer's instructions and the forward (SEQ ID NO: 36) and reverse (SEQ ID NO: 37) primer pair set forth below in Table 6.

TABLE 6

| FORWARD AND REVERSE PRIMER PAIR | | |
|---|---|---|
| Forward | AATCGCAGTATAAGAAGCTCTTCAC TTATGTCGATGAAAAAATGG | SEQ ID NO: 36 |
| Reverse | CAGAAGAAAATGGAGGAATTCCAAC ATTAATTTTTCCGGTTCCTGA | SEQ ID NO: 37 |

The DNA fragment containing the gRNA expression cassette and the two homology arms can be assembled into pRF694 using standard molecular biology techniques generating plasmid pRF731 (SEQ ID NO: 38), generating an *E. coli*-*B. licheniformis* shuttle plasmid containing a Cas9 expression cassette, a gRNA expression cassette encoding a gRNA targeting glcT and a 1001 bp glcT editing template that will create the L67F mutation in the glcT gene and obliterate glcTts1 and alleviate Cas9 mediated cleavage of the target site.

Example 3

Generation of *Bacillus licheniformis* Cells Comprising the GlcT$^{L67F}$ Mutation In the present example, the pRF731 plasmid (SEQ ID NO: 38) described above was amplified using rolling circle amplification (Sygnis) for 18 hours according to manufacturer's instructions. The rolling circle amplified pRF731 (SEQ ID NO: 38) was transformed into competent (parental) *B. licheniformis* cells comprising (harboring) a pBL.comK plasmid (SEQ ID NO: 50) as generally described in International PCR publication Nos. WO2017/075195, WO2002/14490 and WO2008/7989. Cell/DNA transformation mixes were plated onto L-broth (Miller recipe) containing 20 μg/ml of kanamycin and solidified with 1.5% Agar. Colonies were allowed to form at 37° C. Colonies that grew on the L agar plates containing kanamycin were picked and streaked on L agar plates containing 100 μg/ml spectinomycin to select for pBL.comK plasmid (SEQ ID NO: 50). The glcT locus (SEQ ID NO: 51) was amplified from transformed cells using Q5 (NEB) DNA polymerase and standard PCR reactions using the reverse (SEQ ID NO: 52) and forward (SEQ ID NO: 53) primer pair set forth below in Table 7.

TABLE 7

| FORWARD AND REVERSE PRIMER PAIR | | |
|---|---|---|
| Forward | CGGCATCAAGTGGATATTCC | SEQ ID NO: 52 |
| Reverse | TGTAACACAGCGGATATTCC | SEQ ID NO: 53 |

Colony PCR was performed using the following steps: (1) 98° C. for 3 minutes, (2) 98° C. for 5 seconds, (3) 63° C. for 10 seconds, (4) 72° C. for 30 seconds and (5) repeating steps 2-4 29 times, 72° C. 3 minutes. Successful PCR will amplify a 1,069 bp polynucleotide from the glcT locus (SEQ ID NO: 50). Two (2) μl of the PCR was purified by mixing with 5 μl of Exo-SAP-IT and incubated at 37° C. for 15 minutes followed by 15 minutes at 80° C. The purified PCR reactions were diluted with 400 of $ddH_2O$ and Sanger sequenced with the forward primer "TGAGGATCGTGAACAGATCC" (SEQ ID NO: 54).

Sequence alignments comparing the sequencing data to the WT glcT locus (SEQ ID NO: 51) revealed that some of the recovered colonies contained the desired genome edit causing the L67F mutation in the GlcT protein (SEQ ID NO: 55). A colony containing the glcT gene (SEQ ID NO: 56) encoding the L67F GlcT protein (SEQ ID NO: 55), now named allele glcT1 that was still resistant to 100 μg/ml spectinomycin (comprising pBL.comK) was stored as strain BF63 (glcT1 pBL.comK).

Example 4

Construction of RghR2 Cas9 Targeting Vectors

Plasmid pRF724 (SEQ ID NO: 39), targeting the duplication of codons 24-29 (SEQ ID NO: 40) of the *B. licheniformis* rghR2 gene (SEQ ID NO: 41), was created by amplifying a 8.3 kb DNA fragment (SEQ ID NO: 42) from plasmid pRF694, using Q5 according to the manufacturer's instructions and the forward (SEQ ID NO: 43) and reverse (SEQ ID NO: 44) primer pairs set forth in Table 8.

TABLE 8

| FORWARD AND REVERSE PRIMER PAIR | | |
|---|---|---|
| Forward | GAATTCGCGGCCGCACG | SEQ ID NO: 43 |
| Reverse | GATTACGAATGCCGTCTCCCGGTAT CAGG | SEQ ID NO: 44 |

A synthetic DNA fragment (SEQ ID NO: 45) containing the rghR2 editing template (SEQ ID NO: 46), the rrnIp2-gRNA expression cassette (SEQ ID NO: 47) was ordered from IDT and amplified using Q5 DNA polymerase and standard PCR techniques, using the forward (SEQ ID NO: 48) and reverse (SEQ ID NO: 49) primer pairs set forth in Table 9.

TABLE 9

| FORWARD AND REVERSE PRIMER PAIR | | |
|---|---|---|
| Forward | GGCGGCGTTTTCCTGATACCGGGAG | SEQ ID NO: 48 |
| Reverse | ACCCGCGGGGATCCCCATGG | SEQ ID NO: 49 |

The editing template gRNA expression cassette fragment (SEQ ID NO: 47) comprised 5' and 3' homology to the fragment amplified from pRF694 (SEQ ID NO: 42). The two parts were assembled using prolonged overlap extension PCR, and transformed into *E. coli*. A sequence verified isolate was stored as plasmid pRF724 (SEQ ID NO: 39).

Example 5

Generation of *Bacillus licheniformis* Cells Comprising the RghR2$_{rest}$ Allele Plasmid pRF724 (SEQ ID NO: 39) was amplified using rolling circle amplification (RCA) (Sygnis) for 18 hours according to the manufacturer's instructions. The rolling circle amplified pRF724 (SEQ ID NO: 39) was transformed into competent (parental) *B. licheniformis* cells comprising (harboring) a pBL.comK plasmid (SEQ ID NO: 50), as generally described in International PCR publication Nos. WO2017/075195, WO2002/14490 and WO2008/7989. Cell/DNA transformation mixes were plated onto L-broth (miller) containing twenty (20) μg/ml of kanamycin and solidified with 1.5% (w/v) agar. Colonies were allowed to form at 37° C.

Colonies that grew on L agar containing kanamycin were picked, streaked onto agar plates containing one-hundred (100) μg/ml spectinomycin to select for plasmid pBL.comK (SEQ ID NO: 50). The rghR2 locus (SEQ ID NO: 57) was amplified from transformants using Q5 DNA polymerase (NEB) and standard PCR reactions, using the forward (SEQ ID NO: 58) and reverse (SEQ ID NO: 59) primer pairs set for in Table 10.

TABLE 10

| FORWARD AND REVERSE PRIMER PAIR | | |
|---|---|---|
| Forward | GCGAATCGAAAACGGAAAGC | SEQ ID NO: 58 |
| Reverse | TCATCGCGATCGGCATTACG | SEQ ID NO: 59 |

The PCR cycles were performed as described in Example 4, wherein the PCR reaction amplified the rghR2 locus (SEQ ID NO: 57). The PCR product was purified as described in Example 4, and sequenced using the method of Sanger with the sequencing primer (SEQ ID NO: 60) set forth in Table 11.

TABLE 11

| SEQUENCING PRIMER | | |
|---|---|---|
| Forward | TTTCGACTTTCTCGTGCAGG | SEQ ID NO: 60 |

Sequencing alignments comparing the data to the parental rghR2 locus (SEQ ID NO: 57), revealed that a majority of the recovered colonies contained the rghR2$_{rest}$ allele (SEQ ID NO: 61) comprising the deletion of the tandem duplication of codons 24-29 (SEQ ID NO: 40). A colony containing the rghR2$_{rest}$ allele that was still resistant to one hundred (100) μg/ml of spectinomycin (comprising pBL.comK), was stored as strain BF62 (rghR2$_{rest}$ pBL.comK).

Example 6

Generation of *B. licheniformis* Cells Comprising RghR2$_{rest}$ and GlcT1 Alleles Plasmid pRF724 (SEQ ID NO: 39) was amplified using RCA (Sygnis) for 18 hours according to the manufacturer's instructions. The rolling circle amplified pRF724 (SEQ ID NO: 39) was transformed into competent BF63 (glcT1) *B. licheniformis* cells (see, Example 3) comprising (harboring) a pBL.comK (SEQ ID NO: 50) plasmid. Cell/DNA transformation mixes were plated onto L-broth (miller) containing twenty (20) μg/ml of kanamycin and solidified with 1.5% (w/v) agar. Colonies were allowed to form at 37° C.

Colonies that grew on L agar containing kanamycin were picked, streaked onto agar plates containing one hundred (100) μg/ml spectinomycin. The rghR2 locus (SEQ ID NO: 57) was amplified from transformants using Q5 DNA polymerase (NEB) and standard PCR reactions, using the forward (SEQ ID NO: 58) and reverse (SEQ ID NO: 59) primer pair set forth in Table 12.

TABLE 12

| FORWARD AND REVERSE PRIMER PAIR | | |
|---|---|---|
| Forward | GCGAATCGAAAACGGAAAGC | SEQ ID NO: 58 |
| Reverse | TCATCGCGATCGGCATTACG | SEQ ID NO: 59 |

The PCR cycles were performed as described in Example 4, wherein the PCR reaction amplified the rghR2 locus (SEQ ID NO: 57). The PCR product was purified as described in Example 4, and sequenced using the method of Sanger with the sequencing primer (SEQ ID NO: 60) set forth in Table 13.

TABLE 13

| SEQUENCING PRIMER | | |
|---|---|---|
| Forward | TTTCGACTTTCTCGTGCAGG | SEQ ID NO: 60 |

Sequencing alignments comparing the data to the parental rghR2 locus (SEQ ID NO: 57) revealed that a majority of the recovered colonies contained the $rghR2_{rest}$ allele (SEQ ID NO: 61), comprising the deletion of the tandem duplication of codons 24-29 (SEQ ID NO: 40). A colony containing the $rghR2_{rest}$ allele (SEQ ID NO: 61) that was still resistant to one hundred (100) μg/ml of spectinomycin (comprising pBL.comK), was stored as strain BF169 (Host $rghR2_{rest}$glcT1 pBL.comK).

Example 7

Insertion of a Heterologous Amylase Expression Cassette into Parental and Modified *B. licheniformis* Cells BF62, BF63 and BF169

In the present example, Applicant introduced heterologous α-amylase expression cassettes into parental and modified *B. licheniformis* cells BF62, BF63 and BF169. More specifically, the α-amylase expression cassettes described below were introduced into parental and modified *B. licheniformis* cells BF63, BF62 and BF169, wherein modified *B. licheniformis* (daughter) cell "BF63" comprises the introduced allele "glcT1" (i.e., encoding the variant GlcT protein), modified *B. licheniformis* (daughter) cell "BF62" comprises the restored rghr2 gene ($rghr2_{rest}$), and modified *B. licheniformis* (daughter) cell "BF169" comprises both the introduced allele glcT1 and the restored ($rghr2_{rest}$) gene, as presented below in Table 14.

TABLE 14

| *B. LICHENIFORMIS* (DAUGHTER) CELL MODIFICATIONS | |
|---|---|
| Cell/Strain Name | Genetic Modification |
| *B. licheniformis* (parent) cell | n/a |
| BF63 (daughter) cell | glcT1 (L67F) |
| BF62 (daughter) cell | $rghr2_{rest}$ |
| BF169 (daughter) cell | glcT1 (L67F) + $rghr2_{rest}$ |

More particularly with regard to the heterologous α-amylase expression cassettes, Applicant further tested the effects of modified 5' untranslated region (mod-5'-UTR) sequences on expression of genes encoding proteins of interest in *Bacillus* cells, by creating α-amylase expression cassettes comprising either the wild-type *B. subtilis* aprE 5'-UTR (WT-5'-UTR; SEQ ID NO: 62) or a modified 5'-UTR (mod-5'-UTR; SEQ ID NO: 63). Thus, the instant example describes the creation of *Bacillus* host cells for the assessment of various (modified) 5'-UTR constructs, and their impact/influence on the production of proteins of interest when such modified 5'-UTR constructs are operably linked to an upstream (5') promoter and a downstream (3') open reading frame encoding the protein of interest.

Thus, in the present example, parental *B. licheniformis* cells and modified *B. licheniformis* (daughter) cells BF62, BF63, and BF169 (Table 14), comprising a plasmid carrying a xylose-inducible comK expression cassette (SEQ ID NO: 50), were grown overnight at 37° C. and 250 RPM in fifteen (15) ml of L broth (1% (w/v) Tryptone, 0.5% Yeast extract (w/v), 1% NaCl (w/v)), containing one hundred (100) μg/ml spectinomycin dihydrochloride in a 125 ml baffled flask. The overnight culture was diluted to 0.7 ($OD_{600}$ units) in 25 ml fresh L broth containing one hundred (100) μg/ml spectinomycin dihydrochloride in a two hundred fifty (250) ml baffle flask. Cells were grown for one (1) hour at 37° C. (250 RPM). D-xylose was added to 0.1% (w/v) from a 50% (w/v) stock. Cells were grown for an additional four (4) hours at 37° C. (250 RPM) and pelleted at 1700×g for seven (7) minutes.

The cells were resuspended in one fourth (¼) volume of original culture using the spent medium. One hundred (100) μl of concentrated cells were mixed with approximately one (1) μg of either the wild-type (WT) 5'-UTR expression construct (WT-5'-UTR; SEQ ID NO: 64) or the modified 5'-UTR expression construct (mod-5'-UTR; SEQ ID NO: 65). For example, each expression cassette comprised (in the 5' to 3' direction) the same 5' catH homology arm (SEQ ID NO: 66), catH gene (SEQ ID NO: 67) and spoVGrrnIp hybrid promoter (SEQ ID NO: 68), operably linked to either the wild-type *B. subtilis* aprE 5'-UTR (SEQ ID NO: 62) or the modified aprE 5'-UTR (SEQ ID NO: 63). In addition, the 5'-UTR was operably linked to the DNA encoding the lat signal sequence (SEQ ID NO: 69), followed by DNA (ORF) encoding variant *G. stearothermophilus* α-amylase (SEQ ID NO: 70). The 3' end of the DNA (ORF) encoding the variant *G. stearothermophilus* α-amylase (SEQ ID NO: 70), was operably linked to the lat terminator (SEQ ID NO: 71), which was operably linked to the 3' catH homology arm (SEQ ID NO: 72). Transformation reactions were incubated at 37° C., 1000 RPM for approximately ninety (90) minutes.

Transformation mixes were plated on petri plates filled with L-broth containing ten (10) μg/ml chloramphenicol solidified with 1.5% (w/v) agar. Plates were incubated at 37° C. for two (2) days. Colonies were streak purified on petri plates filled with L-broth containing 1% (w/v) insoluble corn starch solidified with 1.5% (w/v) agar. Plates were incubated at 37° C. for twenty-four (24) hours until colonies had formed. Starch hydrolysis was indicated by clearing of the insoluble starch surrounding the colony, forming a halo, and was used to select transformants expressing variant *G. stearothermophilus* α-amylase protein (SEQ ID NO: 73). Colony PCR was used to amplify the catH locus (WT construct, SEQ ID NO: 74; modified construct, SEQ ID NO: 75) from halo producing colonies using standard techniques, and the forward (SEQ ID NO: 76) and reverse (SEQ ID NO: 77) primer pairs set forth in Table 15.

TABLE 15

| FORWARD AND REVERSE PRIMER PAIR | | |
|---|---|---|
| Forward | TGTGTGACGGCTATCATGCC | SEQ ID NO: 76 |
| Reverse | TTGAGAGCCGGCGTTCC | SEQ ID NO: 77 |

PCR products were purified from excess primers and nucleotides using standard techniques and sequenced using the method of Sanger and the sequencing primers set forth in Table 16.

TABLE 16

| SEQUENCING PRIMERS | | |
|---|---|---|
| Forward | AACGAGTTGGAACGGCTTGC | SEQ ID NO: 78 |
| Forward | GGCAACACCTACTCCAGCTT | SEQ ID NO: 79 |
| Forward | GATCACTCCGACATCATCGG | SEQ ID NO: 80 |

Sequence verified *B. licheniformis* (daughter) cells comprising the WT-5'-UTR expression cassette (SEQ ID NO: 64) or sequence verified *B. licheniformis* (daughter) cells comprising the modified-5'-UTR (mod-5'-UTR) expression cassette (SEQ ID NO: 65) were stored as shown in Table 17.

TABLE 17

PARENTAL AND MODIFIED *B. LICHENIFORMIS* CELLS COMPRISING EITHER WT-5'-UTR EXPRESSION CASSETTE OR MOD-5'-UTR EXPRESSION CASSETTE

| Cell/Strain Name | Modification | Cell/Strain Name Comprising WT-5'-UTR Cassette (SEQ ID NO: 64) | Cell/Strain Name Comprising MOD-5'-UTR Cassette (SEQ ID NO: 65) |
|---|---|---|---|
| *B. licheniformis* (parent) cell | n/a | BF134 | BF117 |
| BF63 (daughter) cell | glcT1 (L67F) | HM151 | HM150-1 |
| BF62 (daughter) cell | $rghr2_{rest}$ | BF165 | BF118 |
| BF169 (daughter) cell | glcT1 (L67F) + $rghr2_{rest}$ | BF260 | BF171 |

Example 8

Production of Amylase Enzyme in Modified *B. licheniformis* Cells

In the present example, modified *B. licheniformis* cells comprising the (mutant) allele glcT1 (SNP C199T) encoding the variant GlcT protein (i.e., L67F substitution) and wild-type (parental) *B. licheniformis* cells were struck on Luria agar plates supplemented with 1% insoluble starch. More particularly, the parental and modified *B. licheniformis* (daughter) cells set forth in Table 18 were transformed with an amylase construct described above in Example 7, Table 17 (i.e., WT-5'-UTR expression cassette SEQ ID NO: 64 or mod-5'-UTR expression cassette SEQ ID NO: 65) were tested and stored as shown in Table 18.

TABLE 18

*B. LICHENIFORMIS* HOST CELLS SCREENED

| *B. licheniformis* Host Cells | 5'-UTR | glcT Variant (L67F) |
|---|---|---|
| BF117 | mod-5'-UTR | No |
| HM150-1 | mod-5'-UTR | Yes |
| BF134 | WT-5'-UTR | No |
| HM151 | WT-5'-UTR | Yes |

More specifically, a clearing zone, indicative of amylolytic activity, was clearly visible around the colonies comprising the amylase expression cassette integrated. Thus, the production of the amylase by *B. licheniformis* cells was experimentally tested by growing the cells in micro titer plates, using a MOPS base medium MBD medium, prepared essentially as known in the art (see, Neidhardt et al., 1974), except that $NH_4Cl_2$, $FeSO_4$, and $CaCl_2$ were omitted from the base medium, three (3) mM $K_2HPO_4$ was used, and the base medium was supplemented with sixty (60) mM urea, seventy-five (75) g/L glucose, and one percent (1%) soytone. The micronutrients were made up as a 100× stock solution in one liter, 400 mg $FeSO_4$ $7H_2O$, 100 mg $MnSO_4H_2O$, 100 mg $ZnSO_4$ $7H_2O$, 50 mg $CuCl_2$ $2H_2O$, 100 mg $CoCl_2$ $6H_2O$, 100 mg $NaMoO_4$ $2H_2O$, 100 mg $Na_2B_4O_7$ $10H_2O$, 10 ml of 1M $CaCl_2$, and 10 ml of 0.5 M sodium citrate. $CaCl_2$ was added to five (5) mM, and pH was adjusted to 6.8.

After seventy (70) hours of growth in an Infors incubator (37° C., 270 rpm), the amylase enzyme concentration in the whole cell broth was determined using the α-Amylase Ceralpha Assay Kit (Megazyme, Wicklow, Ireland). The Ceralpha α-amylase assay involves incubating whole culture broth with a substrate mixture under defined conditions, and the reaction is terminated (and color developed) by the addition of a base solution. The substrate is a mixture of the defined oligosaccharide "nonreducing-end blocked p-nitrophenyl maltoheptaoside" ("BPNPG7" substrate), and excess levels of glucoamylase and β-glucosidase (which have no action on the native substrate due to the presence of the "blocking group"). Upon hydrolysis of the oligosaccharide by endo-acting α-amylase (or C6 amylase), the excess quantities of α-glucosidase and glucoamylase present in the mixture give instantaneous and quantitative hydrolysis of the p-nitrophenyl maltosaccharide fragment to glucose and free p-nitrophenol. The absorbance at 405 nm is measured, and relates directly to the level of amylase in the sample analyzed. The equipment used for this set of assays includes a Biomek FX Robot (Beckman Coulter); a SpectraMAX MTP Reader (type 340-Molecular Devices) and iEMS incubator/shaker (Thermo Scientific). In this assay system, the reagent and solutions used were: (1) p-nitrophenyl maltoheptaoside (BPNPG7) substrate (Megazyme Ceralpha kit); (2) Dilution buffer: 50 mM MOPS, 0.1 mM CaCl2, 0.005% TWEEN® 80 buffer, pH 7.15; and (3) 200 mM Boric acid/NaOH buffer, pH 10.2 (STOP buffer).

Thus, a vial containing 54.5 mg BPNPG7 substrate was dissolved in ten (10) ml of milliQ water. The amylase samples (whole cell broth) were diluted 1600× with dilution buffer. The assay was performed by adding twenty-five (25) μl of diluted amylase solution into the wells of a MTP, followed by the addition of thirty-five (35) μl of the 5.45 mg/ml BPNPG7 substrate solution. The solutions were mixed and the MTP was sealed with a plate seal, and placed in an incubator/shaker (iEMS—Thermo Scientific) for eight (8) minutes at 25° C. The reaction was terminated by adding one hundred (100) μl STOP buffer and the absorbance was read at 405 nm in an MTP-Reader. A non-enzyme control was used to correct for background absorbance values. To calculate the variant amylase enzyme concentration (mg/L), a dilution series of purified variant amylase enzyme standard control sample was incorporated into the experiment.

Figure 2B:
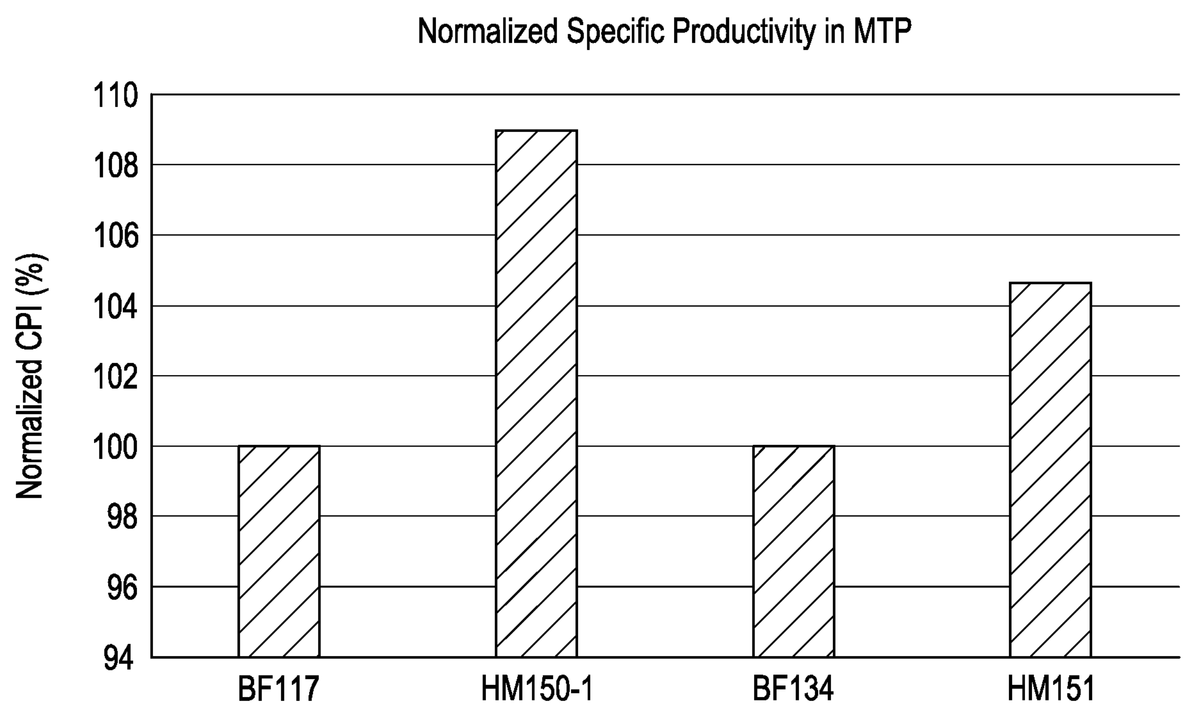

The amylase activity and specific productivity of the amylase are shown in FIG. 2A and FIG. 2B, respectively. For example, as presented in FIG. 2B, the normalized specific productivity of the BF134 cells (BF134: WT-5'-UTR and WT-GlcT) relative to the BF117 cells (BF117: mod-5'-UTR and WT-GlcT) indicates a similar amylase productivity. In contrast, as presented in FIG. 2B, the normalized specific productivity of the HM151 cells (HM151: WT-5'-UTR and allele GlcT1) relative to the BF134 cells or BF117 cells (i.e., both BF134 and BF117 cells comprising a wild-type GkT gene) indicates an approximate 5% increase in specific productivity of the HM151 cells, thereby demonstrating that modified *Bacillus* cells comprising allele glcT1 are capable of producing increased amounts of a protein of interest relative to *Bacillus* cells comprising a native, wild-type glcT gene.

Furthermore, a presented in FIG. 2B, the normalized specific productivity of the HM150-1 cells (HM150-1: mod-5'-UTR and allele GlcT1) relative to the BF134 cells or BF117 cells (i.e., comprising a wild-type GlcT gene) indicates an approximate 9% increase in specific productivity of the HM150-1 cells, further demonstrating that modified *Bacillus* cells comprising allele glcT1 are capable of producing increased amounts of a protein of interest relative to *Bacillus* cells comprising a wild-type glcT gene. Likewise, the normalized specific productivity of the HM150-1 cells (HM150-1: mod-5'-UTR and allele GlcT1) relative to the HM151 cells (HM151: WT-5'-UTR and allele GlcT1) indicates an approximate 4% increase in specific productivity of the HM150-1 relative to the HM151 cells, which demonstrates that "mod-5'-UTR" sequence present in the amylase construct further contributes to the observed increase in specific productivity of the HM150-1 cells.

Example 9

Alpha-Amylase Production at Small Scale

In the present example four *Bacillus* host strains named BF118, BF165, BF171 and BF260, comprising an α-amylase expression cassette with either the WT-5'-UTR (SEQ ID NO: 64) or the mod-5' UTR (SEQ ID NO: 65), were assessed for α-amylase production under small scale conditions. The four strains were streak purified on L agar plates containing 1% ($w{\cdot}v^{-1}$) insoluble starch and grown for approximately twenty-four (24) hours at 37° C. A single halo positive colony was inoculated into 15 ml of Tryptic Soy Broth (1.7% ($w{\cdot}v^{-1}$) Tryptone, 0.3% ($w{\cdot}v^{-1}$) soytone, 0.25% ($w{\cdot}v^{-1}$) glucose, 0.5% ($w{\cdot}v^{-1}$) sodium chloride, 0.25% ($w{\cdot}v^{-1}$) Dipotassium phosphate) and grown at 37° C. (250 RPM) for 6 hours. Subsequently, 0.025 ml of this seed culture was inoculated into 25 ml of flask growth medium (4% ($w{\cdot}v^{-1}$) MES, 0.1% ($w{\cdot}v^{-1}$) Monopotassium phosphate, 0.05% ($w{\cdot}v^{-1}$) sodium chloride, 0.03% ($w{\cdot}v^{-1}$) soytone, containing trace metals, pH 6.8 with Ammonium hydroxide). A single high glucose release feed bead (Kuhner) was added (feed rate 57 mg/L·hr). The cultures were grown at 42° C. (250 RPM) for 90 hours. The total secreted protein production was determined using the method of Bradford with a BSA standard. The relative α-amylase production averaged from repeat measurements of at least two independent flasks for each strain is shown in Table 19 below.

TABLE 19

SMALL SCALE PRODUCTION OF α-AMYLASE

| *B. licheniformis* daughter cell | Modification | Amylase Expression construct | Relative expression ± SEM |
|---|---|---|---|
| BF118 | $rghR2_{rest}$ | (mod-5'-UTR; SEQ ID NO: 65) | 1.00 ± 0.01 |
| BF171 | $rghR2_{rest}$ + glcT1 | (mod-5'-UTR; SEQ ID NO: 65) | 1.09 ± 0.02 |
| BF169 | $rghR2_{rest}$ | (WT-5'-UTR; SEQ ID NO: 64) | 1.0 ± 0.02 |
| BF260 | $rghR2_{rest}$ + glcT1 | (WT-5'-UTR; SEQ ID NO: 64) | 1.09 ± 0.04 |

Thus, as presented in Table 19, the *Bacillus* host cells BF171 and BF260 (comprising a restored rghR2 gene ($rghR2_{rest}$) and allele glcT1) demonstrate an approximately 9% increase in relative α-amylase production when compared (vis-à-vis) to *Bacillus* host cells BF118 and BF169 (comprising a restored rghR2 gene ($rghR2_{rest}$) and a wild-type glcT gene).

REFERENCES

PCT International Publication No. WO 1989/06279
PCT International Publication No. WO 1999/20726
PCT International Publication No. WO 1999/20769
PCT International Publication No. WO 1999/20770
PCT International Publication No. WO2002/14490
PCT International Publication No. WO2003/083125
PCT International Publication No. WO2003/089604
PCT International Publication No. WO2008/024372
PCT International Publication No. WO2009/149130
PCT International Publication No. WO2014/164777
U.S. Pat. No. 4,914,031
U.S. Pat. No. 4,980,288
U.S. Pat. No. 5,208,158
U.S. Pat. No. 5,310,675
U.S. Pat. No. 5,336,611
U.S. Pat. No. 5,399,283
U.S. Pat. No. 5,441,882
U.S. Pat. No. 5,482,849
U.S. Pat. No. 5,631,217
U.S. Pat. No. 5,665,587
U.S. Pat. No. 5,700,676
U.S. Pat. No. 5,741,694
U.S. Pat. No. 5,858,757
U.S. Pat. No. 5,880,080
U.S. Pat. No. 6,197,567
U.S. Pat. No. 6,218,165
U.S. Patent Publication No. 2014/0329309
U.S. RE 34,606
Albertini and Galizzi, *Bacteriol.,* 162:1203-1211, 1985.
Bergmeyer et al., "*Methods of Enzymatic Analysis" vol.* 5, *Peptidases, Proteinases and their Inhibitors, Verlag Chemie, Weinheim,* 1984.
Botstein and Shortie, *Science* 229: 4719, 1985.
Brode et al., "Subtilisin BPN' variants: increased hydrolytic activity on surface-bound substrates via decreased surface activity", *Biochemistry,* 35(10):3162-3169, 1996.
Caspers et al., "Improvement of Sec-dependent secretion of a heterologous model protein in *Bacillus subtilis* by saturation mutagenesis of the N-domain of the AmyE signal peptide", *Appl. Microbiol.* Biotechnol., 86(6): 1877-1885, 2010.

Chang et al., *Mol. Gen. Genet.,* 168:11-115, 1979.
Christianson et al., *Anal. Biochem.,* 223:119-129, 1994.
Devereux et at, *Nucl. Acid Res.,* 12: 387-395, 1984.
Earl et al., "Ecology and genomics of *Bacillus subtilis", Trends in Microbiology.,* 16(6):269-275, 2008.
Ferrari et al., "*Genetics*," in Harwood et al. (ed), *Bacillus*, Plenum Publishing Corp., 1989.
Fisher et. al., *Arch. Microbiol.,* 139:213-217, 1981.
Guerot-Fleury, *Gene,* 167:335-337, 1995.
Hamoen et al., "Controlling competence in *Bacillus subtilis*: shared used of regulators", *Microbiology,* 149:9-17, 2003.
Hamoen et al., *Genes Dev.* 12:1539-1550, 1998.
Hampton et al., *Seroloaical Methods, A Laboratory Manual*, APS Press, St. Paul, Minn. 1990.
Hardwood and Cutting (eds.) *Molecular Biological Methods for Bacillus*, John Wiley & Sons, 1990.
Hayashi et al., *Mol. Microbiol.,* 59(6): 1714-1729, 2006
Higuchi et al., *Nucleic Acids Research* 16: 7351, 1988.
Ho et al., *Gene* 77: 61, 1989.
Hoch et al., *J. Bacteriol.,* 93:1925-1937, 1967.
Holubova, *Folia Microbiol.,* 30:97, 1985.
Hopwood, *The Isolation of Mutants in Methods in Microbiology* (J. R. Norris and D. W. Ribbons, eds.) pp 363-433, Academic Press, New York, 1970.
Horton et al., *Gene* 77: 61, 1989.
Hsia et al., *Anal Biochem.,* 242:221-227, 1999.
Iglesias and Trautner, *Molecular General Genetics* 189: 73-76, 1983.
Jensen et al., "Cell-associated degradation affects the yield of secreted engineered and heterologous proteins in the *Bacillus subtilis* expression system" *Microbiology,* 146 (Pt 10:2583-2594, 2000.
Langbein et al., *J. Mol. Biol.,* 293, 795-805, 1999.
Liu and Zuber, 1998,
Lo et al., *Proceedings of the National Academy of Sciences USA* 81: 2285, 1985.
Maddox et al., *J. Exp. Med.,* 158:1211, 1983.
Manival et al., *EMBO* 1, 16, 5019-5029, 1997.
Mann et al., *Current Microbiol.,* 13:131-135, 1986.
McDonald, *J. Gen. Microbiol.,* 130:203, 1984.
Needleman and Wunsch, *J. Mol. Biol.,* 48: 443, 1970.
Neidhardt et al., "Culture medium for enterobacteria", *J. Bacteriol.,* 119(3): 736-747, 1974.
Ogura & Fujita, *FEMS Microbiol Lett.,* 268(1): 73-80. 2007.
Olempska-Beer et al., "Food-processing enzymes from recombinant microorganisms—a review" *Regul. Toxicol. Pharmacol.,* 45(2):144-158, 2006.
Palmeros et al., *Gene* 247:255-264, 2000.
Parish and Stoker, *FEMS Microbiology Letters* 154: 151-157, 1997.
Pearson and Lipman, *Proc. Natl. Acad. Sci. USA* 85: 2444, 1988.
Perego, 1993, In A. L. Sonneshein, J. A. Hoch, and R. Losick, editors, *Bacillus subtilis and Other Gram-Positive Bacteria, Chapter* 42, *American Society of Microbiology*, Washington, D.C.
Plumbridge, *Curr. Opin. Microbiol.* 5, 187-193, 2002.
Postma et al., *Microbiol. Rev.* 57, 543-594, 1993.
Raul et al., "Production and partial purification of alpha amylase from *Bacillus subtilis* (MTCC 121) using solid state fermentation", *Biochemistry Research International,* 2014.
Sarkar and Sommer, *BioTechniques* 8: 404, 1990.
Saunders et al., *J. Bacteriol.,* 157: 718-726, 1984.
Schmalisch et al., "Control of the *Bacillus subtilis* Antiterminator Protein GlcT by Phosphorylation; Elucidation of The Phosphorylation Chain Leading To Inactivation Of Glct"; *JBC,* 278 (51), 51108-51115, 2003.
Shimada, *Meth. Mol. Biol.* 57: 157; 1996
Smith and Waterman, *Adv. Appl. Math.,* 2: 482, 1981.
Smith et al., *Appl. Env. Microbiol.,* 51:634 1986.
Stahl and Ferrari, *J. Bacteriol.,* 158:411-418, 1984.
Stahl et al, *J. Bacteriol.,* 158:411-418, 1984.
Stulke and Hillen, *Annu. Rev. Microbiol.,* 54, 849-880, 2000.
Stulke et al., *Mol. Microbiol.* 28, 865-874, 1998.
Stulke et al., *Mol. Microbiol.,* 25, 65-78, 1997.
Tarkinen, et al, J. Biol. Chem. 258: 1007-1013, 1983.
Trieu-Cuot et al., *Gene,* 23:331-341, 1983.
Van Dijl and Hecker, "*Bacillus subtilis*: from soil bacterium to super-secreting cell factory", *Microbial Cell Factories,* 12(3). 2013.
Vorobjeva et al., *FEMS Microbiol. Lett.,* 7:261-263, 1980.
Ward, "*Proteinases," in Fogarty* (*ed*), *Microbial Enzymes and Biotechnology. Applied Science*, London, pp 251-317, 1983.
Wells et al., *Nucleic Acids Res.* 11:7911-7925, 1983.
Westers et al., "*Bacillus subtilis* as cell factory for pharmaceutical proteins: a biotechnological approach to optimize the host organism", *Biochimica et Biophysica Acta.,* 1694: 299-310, 2004.
Yang et al, *J. Bacteriol.,* 160: 15-21, 1984.
Yang et al., *Nucleic Acids Res.* 11: 237-249, 1983.
Youngman et al., *Proc. Natl. Acad. Sci. USA* 80: 2305-2309, 1983.

The invention claimed is:

1. A mutant of a parental *Bacillus licheniformis* cell comprising a gene encoding a variant GlcT anti-termination protein comprising at least 90% sequence identity to SEQ ID NO:55, and a phenylalanine (F) at amino acid position 67 (F67) of SEQ ID NO: 55, wherein the gene encoding the variant GlcT protein comprises a nucleic acid sequence comprising at least 90% sequence identity to SEQ ID NO 22, SEQ ID NO: 81 or SEQ ID NO: 56.

2. The mutant cell of claim 1, comprising an introduced polynucleotide encoding a protein of interest (POI).

3. The mutant cell of claim 2, wherein the introduced polynucleotide encoding the POI comprises a modified 5'-untranslated region (mod-5'-UTR) sequence of SEQ ID NO: 63 operably linked and upstream (5') of the polynucleotide encoding the POI.

4. A genetically modified *Bacillus* cell derived from a parental *Bacillus* cell comprising a wild-type gene encoding a wild-type GlcT anti-termination protein of SEQ ID NO: 82, wherein the modified *Bacillus* cell comprises a modified gene encoding a variant GlcT protein comprising at least 90% sequence identity to SEQ ID NO: 55 and comprising a phenylalanine (F) at position 67 of SEQ ID NO: 55.

5. The modified cell of claim 4, wherein the wild-type gene encoding the wild-type GlcT protein of SEQ ID NO: 82 in the parental cell is modified with a glcT transcriptional antiterminator-CRISPR associated protein 9 (glcT-Cas9) targeting vector, wherein the glcT-Cas9 targeting vector modifies codon 67 of the wild-type gene, wherein the modified gene encodes a variant GlcT protein comprising at least 90% sequence identity to SEQ ID NO: 55 and comprising a phenylalanine (F) at position 67 of SEQ ID NO: 55.

6. A genetically modified *Bacillus* cell comprising an introduced polynucleotide encoding a variant GlcT anti-termination protein comprising at least 90% sequence identity to SEQ ID NO: 55 and comprising a phenylalanine (F) at amino acid position 67 (F67) of SEQ ID NO: 55.

7. The modified cell of claim 6, further comprising an inactivated endogenous chromosomal gene encoding a GlcT protein comprising at least 90% sequence identity to SEQ ID NO: 82 and comprising a leucine (L) at amino acid position 67 (L67) of SEQ ID NO: 82.

8. The modified cell of claim 6, further comprising a restored rapG and rapH repressor (rghR2) gene (rghR$2_{rest}$) encoding a restored rapG and rapH repressor (RghR2) protein of SEQ ID NO: 84.

9. The modified cell of claim 6, comprising an introduced polynucleotide encoding a POI.

10. The modified cell of claim 9, wherein introduced polynucleotide encoding the POI comprises a modified 5'-untranslated region (mod-5'-UTR) sequence of SEQ ID NO: 63 operably linked and upstream (5') of the polynucleotide sequence encoding the POI.

11. A modified *Bacillus* cell derived from a parental *Bacillus* cell comprising a gene encoding a wild-type GlcT anti-termination protein comprising a leucine (L) at amino acid position 67 (L67) of SEQ ID NO: 82, wherein the modified *Bacillus* cell comprises a modified gene encoding a variant GlcT protein comprising at least 90% sequence identity to SEQ ID NO:55 and a phenylalanine (F) at amino acid position 67 (F67) of SEQ ID NO: 55, wherein the modified *Bacillus* cell produces an increased amount of a protein of interest (POI) relative to the parental cell producing the same POI.

12. The modified cell of claim 11, comprising an introduced DNA construct encoding a heterologous POI, wherein the modified *Bacillus* cell produces an increased amount of the heterologous POI relative to the parental cell producing the same heterologous POI.

13. The modified cell of claim 11, further comprising a restored rapG and rapH repressor (rghR2) gene (rghR$2_{rest}$) encoding a restored RghR2 protein of SEQ ID NO: 84.

14. The modified cell of claim 12, wherein introduced DNA construct encoding the POI comprises a modified 5'-untranslated region (mod-5'-UTR) sequence of SEQ ID NO: 63 operably linked upstream (5') of the DNA construct.

15. An isolated polynucleotide open reading frame (ORF) encoding a variant *Bacillus* sp. GlcT anti-termination protein, the variant GlcT protein comprising at least 90% identity to SEQ ID NO: 55 and a leucine (L) to phenylalanine (F) substitution at amino acid position 67 (L67F) of SEQ ID NO: 55.

16. A vector comprising the polynucleotide ORF of claim 15.

17. An expression construct comprising the ORF of claim 15, wherein the construct further comprises a promoter nucleic acid sequence functional in *Bacillus* sp. cells, wherein the promoter sequence is operably linked and upstream (5') of the ORF sequence.

18. The construct of claim 17, further comprising a modified *B. subtilis* aprE 5'-untranslated region sequence (5'-UTR) of SEQ ID NO: 63, wherein the modified 5'-UTR is downstream (3') and operably linked to the promoter sequence and upstream (5') and operably linked to the ORF sequence.

19. A method for producing an increased amount of a protein of interest (POI) in a mutant of a parental *Bacillus licheniformis* cell comprising:

(a) obtaining a mutant of a parental *B. licheniformis* cell comprising a glcT gene encoding a GlcT protein comprising at least 90% sequence identity to SEQ ID NO: 55 and a phenylalanine (F) at amino acid position 67 (F67) of SEQ ID NO: 55 and introducing into the mutant cell a DNA construct encoding a heterologous POI, (b) cultivating the mutant cell of step (a) in a medium suitable for the production of a POI, and (c) recovering the POI from the cultivation medium, wherein the mutant *B. licheniformis* cell produces an increased amount of the POI relative to the parental *B. licheniformis* cell producing the same POI, when cultivated under the same conditions.

20. A method for producing an increased amount of a protein of interest (POI) in a modified *Bacillus* cell derived from an unmodified *Bacillus* parental cell comprising:

(a) obtaining a parental *Bacillus* cell comprising an endogenous chromosomal glcT gene encoding a wild-type GlcT protein comprising a leucine (L) at amino acid position 67 (L67) of SEQ ID NO: 82 and modifying the parental cell by introducing (i) a polynucleotide encoding a variant GlcT protein comprising at least 90% sequence identity to SEQ ID NO: 55 and comprising a phenylalanine (F) at amino acid position 67 (F67) of SEQ ID NO: 55 and (ii) a polynucleotide encoding a POI, (b) cultivating the modified cell of step (a) in a medium suitable for the production of a POI, and (c) recovering the POI from the cultivation medium, wherein the modified *Bacillus* cell produces an increased amount of the POI relative to the parental cell producing the same POI when cultivated under the same conditions.

21. The method of claim 20, wherein the introduced polynucleotide encoding the GlcT variant protein integrates into the chromosomal glcT gene locus by homologous recombination, thereby replacing and eliminating the endogenous chromosomal glcT gene encoding the GlcT protein of SEQ ID NO: 82.

22. A method for producing an increased amount of a protein of interest (POI) in a modified *Bacillus* cell derived from an unmodified *Bacillus* parental cell comprising:

(a) obtaining a parental *Bacillus* cell comprising an endogenous chromosomal glcT gene encoding a wild-type GlcT protein comprising a leucine (L) at amino acid position 67 (L67) of SEQ ID NO: 82, (b) modifying the parental cell of step (a) with a glcT-Cas9 targeting vector, wherein the glcT-Cas9 targeting vector modifies codon 67 of the wild-type glcT gene, wherein modified glcT gene encodes a variant GlcT protein comprising at least 90% sequence identity to SEQ ID NO: 55 and comprising a phenylalanine (F) at position 67 of SEQ ID NO: 55, (c) cultivating the modified cell of step (b) in a medium suitable for the production of a POI, and (c) recovering the POI from the cultivation medium, wherein the modified *Bacillus* cell produces an increased amount of the POI relative to the parental cell producing the same POI when cultivated under the same conditions.

* * * * *

SEQUENCE LISTING

```
<160> NUMBER OF SEQ ID NOS: 84

<210> SEQ ID NO 1
<211> LENGTH: 4188
<212> TYPE: DNA
<213> ORGANISM: Artificial Sequence
<220> FEATURE:
<223> OTHER INFORMATION: synthetic polynucleotide encoding Cas9

<400> SEQUENCE: 1

gtggccccaa aaaagaaacg caaggttatg gataaaaaat acagcattgg tctggatatc      60

ggaaccaaca gcgttgggtg ggcagtaata acagatgaat acaaagtgcc gtcaaaaaaa     120

tttaaggttc tggggaatac agatcgccac agcataaaaa agaatctgat tggggcattg     180

ctgtttgatt cgggtgagac agctgaggcc acgcgtctga aacgtacagc aagaagacgt     240
```

```
tacacacgtc gtaaaaatcg tatttgctac ttacaggaaa ttttttctaa cgaaatggcc    300
aaggtagatg atagtttctt ccatcgtctc gaagaatctt ttctggttga ggaagataaa    360
aaacacgaac gtcaccctat ctttggcaat atcgtggatg aagtggccta tcatgaaaaa    420
taccctacga tttatcatct tcgcaagaag ttggttgata gtacggacaa agcggatctg    480
cgtttaatct atcttgcgtt agcgcacatg atcaaatttc gtggtcattt cttaattgaa    540
ggtgatctga atcctgataa ctctgatgtg gacaaattgt ttatacaatt agtgcaaacc    600
tataatcagc tgttcgagga aaaccccatt aatgcctctg gagttgatgc caaagcgatt    660
ttaagcgcga gactttctaa gtcccggcgt ctggagaatc tgatcgccca gttaccaggg    720
gaaaagaaaa atggtctgtt tggtaatctg attgccctca gtctggggct taccccgaac    780
ttcaaatcca attttgacct ggctgaggac gcaaagctgc agctgagcaa agatacttat    840
gatgatgacc tcgacaatct gctcgcccag attggtgacc aatatgcgga tctgtttctg    900
gcagcgaaga atctttcgga tgctatcttg ctgtcggata ttctgcgtgt taataccgaa    960
atcaccaaag cgcctctgtc tgcaagtatg atcaagagat acgacgagca ccaccaggac   1020
ctgactcttc ttaaggcact ggtacgccaa cagcttccgg agaaatacaa agaaatattc   1080
ttcgaccagt ccaagaatgg ttacgcgggc tacatcgatg gtggtgcatc acaggaagag   1140
ttctataaat ttattaaacc aatccttgag aaaatggatg gcacggaaga gttacttgtt   1200
aaacttaacc gcgaagactt gcttagaaag caacgtacat tcgacaacgg ctccatccca   1260
caccagattc atttaggtga acttcacgcc atcttgcgca gacaagaaga tttctatccc   1320
ttcttaaaag acaatcggga gaaaatcgag aagatcctga cgttccgcat tccctattat   1380
gtcggtcccc tggcacgtgg taattctcgg tttgcctgga tgacgcgcaa aagtgaggaa   1440
accatcaccc cttggaactt tgaagaagtc gtggataaag gtgctagcgc gcagtctttt   1500
atagaaagaa tgacgaactt cgataaaaac ttgcccaacg aaaaagtcct gcccaagcac   1560
tctcttttat atgagtactt tactgtgtac aacgaactga ctaaagtgaa atacgttacg   1620
gaaggtatgc gcaaacctgc ctttcttagt ggcgagcaga aaaaagcaat tgtcgatctt   1680
ctctttaaaa cgaatcgcaa ggtaactgta aaacagctga aggaagatta tttcaaaaag   1740
atcgaatgct ttgattctgt cgagatctcg ggtgtcgaag atcgtttcaa cgcttcctta   1800
gggacctatc atgatttgct gaagataata aaagacaaag actttctcga caatgaagaa   1860
aatgaagata ttctggagga tattgttttg accttgacct tattcgaaga tagagagatg   1920
atcgaggagc gcttaaaaac ctatgcccac ctgtttgatg acaaagtcat gaagcaatta   1980
aagcgccgca gatatacggg gtggggccgc ttgagccgca agttgattaa cggtattaga   2040
gacaagcaga gcggaaaaac tatcctggat ttcctcaaat ctgacggatt tgcgaaccgc   2100
aattttatgc agcttataca tgatgattcg cttacattca aagaggatat tcagaaggct   2160
caggtgtctg ggcaaggtga ttcactccac gaacatatag caaatttggc cggctctcct   2220
gcgattaaga aggggatcct gcaaacagtt aaagttgtgg atgaacttgt aaaagtaatg   2280
ggccgccaca agccggagaa tatcgtgata gaaatggcgc gcgagaatca aacgacacaa   2340
aaaggtcaaa agaactcaag agagagaatg aagcgcattg aggaggggat aaaggaactt   2400
ggatctcaaa ttctgaaaga acatccagtt gaaaacactc agctgcaaaa tgaaaaattg   2460
tacctgtact acctgcagaa tggaagagac atgtacgtgg atcaggaatt ggatatcaat   2520
agactctcgg actatgacgt agatcacatt gtccctcaga gcttcctcaa ggatgattct   2580
```

```
atagataata aagtacttac gagatcggac aaaaatcgcg gtaaatcgga taacgtccca   2640
tcggaggaag tcgttaaaaa gatgaaaaac tattggcgtc aactgctgaa cgccaagctg   2700
atcacacagc gtaagtttga taatctgact aaagccgaac gcggtggtct tagtgaactc   2760
gataaagcag gatttataaa acggcagtta gtagaaacgc gccaaattac gaaacacgtg   2820
gctcagatcc tcgattctag aatgaataca aagtacgatg aaaacgataa actgatccgt   2880
gaagtaaaag tcattacctt aaaatctaaa cttgtgtccg atttccgcaa agattttcag   2940
ttttacaagg tccgggaaat caataactat caccatgcac atgatgcata tttaaatgcg   3000
gttgtaggca cggcccttat taagaaatac cctaaactcg aaagtgagtt tgtttatggg   3060
gattataaag tgtatgacgt tcgcaaaatg atcgcgaaat cagaacagga aatcggtaag   3120
gctaccgcta aatacttttt ttattccaac attatgaatt tttttaagac cgaaataact   3180
ctcgcgaatg gtgaaatccg taaacggcct cttatagaaa ccaatggtga aacgggagaa   3240
atcgtttggg ataaaggtcg tgactttgcc accgttcgta aagtcctctc aatgccgcaa   3300
gttaacattg tcaagaagac ggaagttcaa acagggggat tctccaaaga atctatcctg   3360
ccgaagcgta acagtgataa acttattgcc agaaaaaaag attgggatcc aaaaaaatac   3420
ggaggctttg attcccctac cgtcgcgtat agtgtgctgg tggttgctaa agtcgagaaa   3480
gggaaaagca agaaattgaa atcagttaaa gaactgctgg gtattacaat tatggaaaga   3540
tcgtcctttg agaaaaatcc gatcgacttt ttagaggcca aggggtataa ggaagtgaaa   3600
aaagatctca tcatcaaatt accgaagtat agtctttttg agctggaaaa cggcagaaaa   3660
agaatgctgg cctccgcggg cgagttacag aagggaaatg agctggcgct gccttccaaa   3720
tatgttaatt ttctgtacct tgccagtcat tatgagaaac tgaagggcag ccccgaagat   3780
aacgaacaga aacaattatt cgtggaacag cataagcact atttagatga aattatagag   3840
caaattagtg aatttctaa gcgcgttatc ctcgcggatg ctaatttaga caaagtactg   3900
tcagcttata ataaacatcg ggataagccg attagagaac aggccgaaaa tatcattcat   3960
ttgtttacct taaccaacct tggagcacca gctgccttca aatatttcga taccacaatt   4020
gatcgtaaac ggtatacaag tacaaaagaa gtcttggacg caaccctcat tcatcaatct   4080
attactggat tatatgagac acgcattgat ctttcacagc tgggcggaga caagaagaaa   4140
aaactgaaac tgcaccatca tcaccatcat catcaccatc attgataa               4188
```

```
<210> SEQ ID NO 2
<211> LENGTH: 8
<212> TYPE: PRT
<213> ORGANISM: Artificial Sequence
<220> FEATURE:
<223> OTHER INFORMATION: N-terminal NLS

<400> SEQUENCE: 2

Ala Pro Lys Lys Lys Arg Lys Val
1               5


<210> SEQ ID NO 3
<211> LENGTH: 6
<212> TYPE: PRT
<213> ORGANISM: Artificial Sequence
<220> FEATURE:
<223> OTHER INFORMATION: C-terminal NLS

<400> SEQUENCE: 3

Lys Lys Lys Lys Leu Lys
1               5
```

<210> SEQ ID NO 4
<211> LENGTH: 10
<212> TYPE: PRT
<213> ORGANISM: Artificial Sequence
<220> FEATURE:
<223> OTHER INFORMATION: 10-histidine tag

<400> SEQUENCE: 4

His His His His His His His His His His
1 5 10

<210> SEQ ID NO 5
<211> LENGTH: 607
<212> TYPE: DNA
<213> ORGANISM: Bacillus subtilis

<400> SEQUENCE: 5
attcctccat tttcttctgc tatcaaaata acagactcgt gattttccaa acgagctttc 60
aaaaaagcct ctgccccttg caaatcggat gcctgtctat aaaattcccg atattggtta 120
aacagcggcg caatggcggc cgcatctgat gtctttgctt ggcgaatgtt catcttattt 180
cttcctccct ctcaataatt ttttcattct atccctttc tgtaaagttt atttttcaga 240
atacttttat catcatgctt tgaaaaaata tcacgataat atccattgtt ctcacggaag 300
cacacgcagg tcatttgaac gaatttttc gacaggaatt tgccgggact caggagcatt 360
taacctaaaa aagcatgaca tttcagcata atgaacattt actcatgtct attttcgttc 420
ttttctgtat gaaaatagtt atttcgagtc tctacggaaa tagcgagaga tgatatacct 480
aaatagagat aaaatcatct caaaaaaatg ggtctactaa aatattattc catctattac 540
aataaattca cagaatagtc ttttaagtaa gtctactctg aattttttta aaaggagagg 600
gtaacta 607

<210> SEQ ID NO 6
<211> LENGTH: 50
<212> TYPE: DNA
<213> ORGANISM: Artificial Sequence
<220> FEATURE:
<223> OTHER INFORMATION: Cas9 forward primer

<400> SEQUENCE: 6
atatatgagt aaacttggtc tgacagaatt cctccatttt cttctgctat 50

<210> SEQ ID NO 7
<211> LENGTH: 35
<212> TYPE: DNA
<213> ORGANISM: Artificial Sequence
<220> FEATURE:
<223> OTHER INFORMATION: Cas9 reverse primer

<400> SEQUENCE: 7
tgcggccgcg aattcgatta cgaatgccgt ctccc 35

<210> SEQ ID NO 8
<211> LENGTH: 3290
<212> TYPE: DNA
<213> ORGANISM: Artificial Sequence
<220> FEATURE:
<223> OTHER INFORMATION: pKB320 backbone

<400> SEQUENCE: 8
gaattcgcgg ccgcacgcgt ccatggggat ccccgcgggt cgacctcgag agttacgcta 60

```
gggataacag ggtaatatag gagctccagt cggcttaaac cagttttcgc tggtgcgaaa    120
aaagagtgtc ttgtgacacc taaattcaaa atctatcggt cagatttata ccgatttgat    180
tttatatatt cttgaataac atacgccgag ttatcacata aaagcgggaa ccaatcataa    240
aatttaaact tcattgcata atccattaaa ctcttaaatt ctacgattcc ttgttcatca    300
ataaactcaa tcatttcttt aattaattta tatctatctg ttgttgtttt ctttaataat    360
tcattaacat ctacaccgcc ataaactatc atatcttctt tttgatattt aaatttatta    420
ggatcgtcca tgtgaagcat atatctcaca agacctttca cacttcctgc aatctgcgga    480
atagtcgcat tcaattcttc tgttaattat ttttatctgt tcataagatt tattaccctc    540
atacatcact agaatatgat aatgctcttt tttcatccta ccttctgtat cagtatccct    600
atcatgtaat ggagacacta caaattgaat gtgtaactct tttaaatact ctaaccactc    660
ggcttttgct gattctggat ataaaacaaa tgtccaatta cgtcctcttg aatttttctt    720
gttttcagtt tcttttatta cattttcgct catgatataa taacggtgct aatacactta    780
acaaaattta gtcatagata ggcagcatgc cagtgctgtc tatctttttt tgtttaaaat    840
gcaccgtatt cctcctttgc atattttttt attagaatac cggttgcatc tgatttgcta    900
atattatatt tttctttgat tctatttaat atctcatttt cttctgttgt aagtcttaaa    960
gtaacagcaa ctttttctc ttcttttcta tctacaacta tcactgtacc tcccaacatc    1020
tgttttttc actttaacat aaaaaacaac cttttaacat taaaaaccca atatttattt    1080
atttgtttgg acaatggaca ctggacacct agggggagg tcgtagtacc cccctatgtt    1140
ttctccccta aataacccca aaaatctaag aaaaaaagac ctcaaaaagg tctttaatta    1200
acatctcaaa tttcgcattt attccaattt cctttttgcg tgtgatgcga gctcatcggc    1260
tccgtcgata ctatgttata cgccaacttt caaaacaact ttgaaaaagc tgttttctgg    1320
tatttaaggt tttagaatgc aaggaacagt gaattggagt tcgtcttgtt ataattagct    1380
tcttggggta tctttaaata ctgtagaaaa gaggaaggaa ataataaatg gctaaaatga    1440
gaatatcacc ggaattgaaa aaactgatcg aaaaataccg ctgcgtaaaa gatacggaag    1500
gaatgtctcc tgctaaggta tataagctgg tgggagaaaa tgaaaaccta tatttaaaaa    1560
tgacggacag ccggtataaa gggaccacct atgatgtgga acgggaaaag gacatgatgc    1620
tatggctgga aggaaagctg cctgttccaa aggtcctgca ctttgaacgg catgatggct    1680
ggagcaatct gctcatgagt gaggccgatg gcgtcctttg ctcggaagag tatgaagatg    1740
aacaaagccc tgaaaagatt atcgagctgt atgcggagtg catcaggctc tttcactcca    1800
tcgacatatc ggattgtccc tatacgaata gcttagacag ccgcttagcc gaattggatt    1860
acttactgaa taacgatctg gccgatgtgg attgcgaaaa ctgggaagaa gacactccat    1920
ttaaagatcc gcgcgagctg tatgattttt taaagacgga aaagcccgaa gaggaacttg    1980
tcttttccca cggcgacctg ggagacagca acatctttgt gaaagatggc aaagtaagtg    2040
gctttattga tcttgggaga agcggcaggg cggacaagtg gtatgacatt gccttctgcg    2100
tccggtcgat cagggaggat atcggggaag aacagtatgt cgagctattt tttgacttac    2160
tggggatcaa gcctgattgg gagaaaataa aatattatat tttactggat gaattgtttt    2220
agtgactgca gtgagatctg gtaatgactc tctagcttga ggcatcaaat aaaacgaaag    2280
gctcagtcga aagactgggc ctttcgtttt atctgttgtt tgtcggtgaa cgctctcctg    2340
agtaggacaa atccgccgct ctagctaagc agaaggccat cctgacggat ggcctttttg    2400
```

```
cgtttctaca aactcttgtt aactctagag ctgcctgccg cgtttcggtg atgaagatct   2460

tcccgatgat taattaattc agaacgctcg gttgccgccg ggcgtttttt atgaagcttc   2520

gttgctggcg tttttccata ggctccgccc ccctgacgag catcacaaaa atcgacgctc   2580

aagtcagagg tggcgaaacc cgacaggact ataaagatac caggcgtttc cccctggaag   2640

ctccctcgtg cgctctcctg ttccgaccct gccgcttacc ggatacctgt ccgcctttct   2700

cccttcggga agcgtggcgc tttctcatag ctcacgctgt aggtatctca gttcggtgta   2760

ggtcgttcgc tccaagctgg gctgtgtgca cgaacccccc gttcagcccg accgctgcgc   2820

cttatccggt aactatcgtc ttgagtccaa cccggtaaga cacgacttat cgccactggc   2880

agcagccact ggtaacagga ttagcagagc gaggtatgta ggcggtgcta cagagttctt   2940

gaagtggtgg cctaactacg gctacactag aaggacagta tttggtatct gcgctctgct   3000

gaagccagtt accttcggaa aaagagttgg tagctcttga tccggcaaac aaaccaccgc   3060

tggtagcggt ggtttttttg tttgcaagca gcagattacg cgcagaaaaa aaggatctca   3120

agaagatcct ttgatctttt ctacggggtc tgacgctcag tggaacgaaa actcacgtta   3180

agggattttg gtcatgagat tatcaaaaag gatcttcacc tagatccttt taaattaaaa   3240

atgaagtttt aaatcaatct aaagtatata tgagtaaact tggtctgaca              3290
```

```
<210> SEQ ID NO 9
<211> LENGTH: 4204
<212> TYPE: DNA
<213> ORGANISM: Artificial Sequence
<220> FEATURE:
<223> OTHER INFORMATION: pKB320

<400> SEQUENCE: 9
```

```
gcggccgcac gcgtccatgg ggatccccgc gggtcgacct cgagagttac gctagggata     60

acagggtaat ataggagctc cagtcggctt aaaccagttt tcgctggtgc gaaaaaagag    120

tgtcttgtga cacctaaatt caaaatctat cggtcagatt tataccgatt tgattttata    180

tattcttgaa taacatacgc cgagttatca cataaaagcg ggaaccaatc ataaaattta    240

aacttcattg cataatccat taaactctta aattctacga ttccttgttc atcaataaac    300

tcaatcattt ctttaattaa tttatatcta tctgttgttg ttttctttaa taattcatta    360

acatctacac cgccataaac tatcatatct tctttttgat atttaaattt attaggatcg    420

tccatgtgaa gcatatatct cacaagacct ttcacacttc ctgcaatctg cggaatagtc    480

gcattcaatt cttctgttaa ttatttttat ctgttcataa gatttattac cctcatacat    540

cactagaata tgataatgct ctttttttcat cctaccttct gtatcagtat ccctatcatg    600

taatggagac actacaaatt gaatgtgtaa ctcttttaaa tactctaacc actcggcttt    660

tgctgattct ggatataaaa caaatgtcca attacgtcct cttgaatttt tcttgttttc    720

agtttctttt attacatttt cgctcatgat ataataacgg tgctaataca cttaacaaaa    780

tttagtcata gataggcagc atgccagtgc tgtctatctt tttttgttta aaatgcaccg    840

tattcctcct ttgcatattt ttttattaga ataccggttg catctgattt gctaatatta    900

tatttttctt tgattctatt taatatctca ttttcttctg ttgtaagtct taaagtaaca    960

gcaacttttt tctcttcttt tctatctaca actatcactg tacctcccaa catctgtttt   1020

tttcacttta acataaaaaa caacctttta acattaaaaa cccaatattt atttatttgt   1080

ttggacaatg gacactggac acctaggggg gaggtcgtag taccccccta tgttttctcc   1140

cctaaataac cccaaaaatc taagaaaaaa agacctcaaa aaggtcttta attaacatct   1200
```

```
caaatttcgc atttattcca atttcctttt tgcgtgtgat gcgagctcat cggctccgtc   1260
gatactatgt tatacgccaa ctttcaaaac aactttgaaa aagctgtttt ctggtattta   1320
aggttttaga atgcaaggaa cagtgaattg gagttcgtct tgttataatt agcttcttgg   1380
ggtatcttta aatactgtag aaaagaggaa ggaaataata aatggctaaa atgagaatat   1440
caccggaatt gaaaaaactg atcgaaaaat accgctgcgt aaaagatacg gaaggaatgt   1500
ctcctgctaa ggtatataag ctggtgggag aaaatgaaaa cctatattta aaaatgacgg   1560
acagccggta taaagggacc acctatgatg tggaacggga aaaggacatg atgctatggc   1620
tggaaggaaa gctgcctgtt ccaaaggtcc tgcactttga acggcatgat ggctggagca   1680
atctgctcat gagtgaggcc gatggcgtcc tttgctcgga agagtatgaa gatgaacaaa   1740
gccctgaaaa gattatcgag ctgtatgcgg agtgcatcag gctctttcac tccatcgaca   1800
tatcggattg tccctatacg aatagcttag acagccgctt agccgaattg gattacttac   1860
tgaataacga tctggccgat gtggattgcg aaaactggga agaagacact ccatttaaag   1920
atccgcgcga gctgtatgat tttttaaaga cggaaaagcc cgaagaggaa cttgtctttt   1980
cccacggcga cctgggagac agcaacatct ttgtgaaaga tggcaaagta agtggcttta   2040
ttgatcttgg gagaagcggc agggcggaca agtggtatga cattgccttc tgcgtccggt   2100
cgatcaggga ggatatcggg gaagaacagt atgtcgagct atttttttgac ttactgggga   2160
tcaagcctga ttgggagaaa ataaaatatt atattttact ggatgaattg ttttagtgac   2220
tgcagtgaga tctggtaatg actctctagc ttgaggcatc aaataaaacg aaaggctcag   2280
tcgaaagact gggcctttcg ttttatctgt tgtttgtcgg tgaacgctct cctgagtagg   2340
acaaatccgc cgctctagct aagcagaagg ccatcctgac ggatggcctt tttgcgtttc   2400
tacaaactct tgttaactct agagctgcct gccgcgtttc ggtgatgaag atcttcccga   2460
tgattaatta attcagaacg ctcggttgcc gccgggcgtt ttttatgaag cttcgttgct   2520
ggcgtttttc cataggctcc gcccccctga cgagcatcac aaaaatcgac gctcaagtca   2580
gaggtggcga aacccgacag gactataaag ataccaggcg tttccccctg gaagctccct   2640
cgtgcgctct cctgttccga ccctgccgct taccggatac ctgtccgcct ttctcccttc   2700
gggaagcgtg gcgctttctc atagctcacg ctgtaggtat ctcagttcgg tgtaggtcgt   2760
tcgctccaag ctgggctgtg tgcacgaacc ccccgttcag cccgaccgct gcgccttatc   2820
cggtaactat cgtcttgagt ccaacccggt aagacacgac ttatcgccac tggcagcagc   2880
cactggtaac aggattagca gagcgaggta tgtaggcggt gctacagagt tcttgaagtg   2940
gtggcctaac tacggctaca ctagaaggac agtatttggt atctgcgctc tgctgaagcc   3000
agttaccttc ggaaaaagag ttggtagctc ttgatccggc aaacaaacca ccgctggtag   3060
cggtggtttt tttgtttgca agcagcagat tacgcgcaga aaaaaaggat ctcaagaaga   3120
tcctttgatc ttttctacgg ggtctgacgc tcagtggaac gaaaactcac gttaagggat   3180
tttggtcatg agattatcaa aaaggatctt cacctagatc cttttaaatt aaaaatgaag   3240
ttttaaatca atctaaagta tatatgagta aacttggtct gacagttacc aatgcttaat   3300
cagtgaggca cctatctcag cgatctgtct atttcgttca tccatagttg cctgactccc   3360
cgtcgtgtag ataactacga tacgggaggg cttaccatct ggccccagtg ctgcaatgat   3420
accgcgagac ccacgctcac cggctccaga tttatcagca ataaaccagc cagccggaag   3480
ggccgagcgc agaagtggtc ctgcaacttt atccgcctcc atccagtcta ttaattgttg   3540
```

ccgggaagct agagtaagta gttcgccagt taatagtttg cgcaacgttg ttgccattgc 3600
tacaggcatc gtggtgtcac gctcgtcgtt tggtatggct tcattcagct ccggttccca 3660
acgatcaagg cgagttacat gatcccccat gttgtgcaaa aaagcggtta gctccttcgg 3720
tcctccgatc gttgtcagaa gtaagttggc cgcagtgtta tcactcatgg ttatggcagc 3780
actgcataat tctcttactg tcatgccatc cgtaagatgc ttttctgtga ctggtgagta 3840
ctcaaccaag tcattctgag aatagtgtat gcggcgaccg agttgctctt gcccggcgtc 3900
aatacgggat aataccgcgc cacatagcag aactttaaaa gtgctcatca ttggaaaacg 3960
ttcttcgggg cgaaaactct caaggatctt accgctgttg agatccagtt cgatgtaacc 4020
cactcgtgca cccaactgat cttcagcatc ttttactttc accagcgttt ctgggtgagc 4080
aaaaacagga aggcaaaatg ccgcaaaaaa gggaataagg gcgacacgga aatgttgaat 4140
actcatactc ttcctttttc aatattattg aagcatttat cagggttatt gtctcatgga 4200
attc 4204

<210> SEQ ID NO 10
<211> LENGTH: 35
<212> TYPE: DNA
<213> ORGANISM: Artificial Sequence
<220> FEATURE:
<223> OTHER INFORMATION: pKB320 forward primer

<400> SEQUENCE: 10
gggagacggc attcgtaatc gaattcgcgg ccgca 35

<210> SEQ ID NO 11
<211> LENGTH: 50
<212> TYPE: DNA
<213> ORGANISM: Artificial Sequence
<220> FEATURE:
<223> OTHER INFORMATION: pKB320 reverse primer

<400> SEQUENCE: 11
atagcagaag aaaatggagg aattctgtca gaccaagttt actcatatat 50

<210> SEQ ID NO 12
<211> LENGTH: 23
<212> TYPE: DNA
<213> ORGANISM: Artificial Sequence
<220> FEATURE:
<223> OTHER INFORMATION: Cas9 reverse sequencing primer

<400> SEQUENCE: 12
ccgactggag ctcctatatt acc 23

<210> SEQ ID NO 13
<211> LENGTH: 20
<212> TYPE: DNA
<213> ORGANISM: Artificial Sequence
<220> FEATURE:
<223> OTHER INFORMATION: Cas9 reverse sequening primer 2

<400> SEQUENCE: 13
gctgtggcga tctgtattcc 20

<210> SEQ ID NO 14
<211> LENGTH: 22
<212> TYPE: DNA
<213> ORGANISM: Artificial Sequence
<220> FEATURE:
<223> OTHER INFORMATION: Cas9 forward sequencing primer 1

<400> SEQUENCE: 14
gtcttttaag taagtctact ct 22

<210> SEQ ID NO 15
<211> LENGTH: 20
<212> TYPE: DNA
<213> ORGANISM: Artificial Sequence
<220> FEATURE:
<223> OTHER INFORMATION: Cas9 forward seq primer 2

<400> SEQUENCE: 15
ccaaagcgat tttaagcgcg 20

<210> SEQ ID NO 16
<211> LENGTH: 20
<212> TYPE: DNA
<213> ORGANISM: Artificial Sequence
<220> FEATURE:
<223> OTHER INFORMATION: Cas9 forward seq primer 3

<400> SEQUENCE: 16
cctggcacgt ggtaattctc 20

<210> SEQ ID NO 17
<211> LENGTH: 20
<212> TYPE: DNA
<213> ORGANISM: Artificial Sequence
<220> FEATURE:
<223> OTHER INFORMATION: Cas9 forward seq primer 4

<400> SEQUENCE: 17
ggatttcctc aaatctgacg 20

<210> SEQ ID NO 18
<211> LENGTH: 21
<212> TYPE: DNA
<213> ORGANISM: Artificial Sequence
<220> FEATURE:
<223> OTHER INFORMATION: Cas9 forward seq primer 5

<400> SEQUENCE: 18
gtagaaacgc gccaaattac g 21

<210> SEQ ID NO 19
<211> LENGTH: 20
<212> TYPE: DNA
<213> ORGANISM: Artificial Sequence
<220> FEATURE:
<223> OTHER INFORMATION: Cas9 forward seq primer 6

<400> SEQUENCE: 19
gctggtggtt gctaaagtcg 20

<210> SEQ ID NO 20
<211> LENGTH: 20
<212> TYPE: DNA
<213> ORGANISM: Artificial Sequence
<220> FEATURE:
<223> OTHER INFORMATION: Cas9 forward seq primer 7

<400> SEQUENCE: 20
ggacgcaacc ctcattcatc 20

<210> SEQ ID NO 21

<211> LENGTH: 8347
<212> TYPE: DNA
<213> ORGANISM: Artificial Sequence
<220> FEATURE:
<223> OTHER INFORMATION: pRF694

<400> SEQUENCE: 21

```
gaattcctcc atttcttct gctatcaaaa taacagactc gtgattttcc aaacgagctt     60
tcaaaaaagc ctctgcccct tgcaaatcgg atgcctgtct ataaaattcc cgatattggt    120
taaacagcgg cgcaatggcg gccgcatctg atgtctttgc ttggcgaatg ttcatcttat    180
ttcttcctcc ctctcaataa ttttttcatt ctatcccttt tctgtaaagt ttatttttca    240
gaatactttt atcatcatgc tttgaaaaaa tatcacgata atatccattg ttctcacgga    300
agcacacgca ggtcatttga acgaattttt tcgacaggaa tttgccggga ctcaggagca    360
tttaacctaa aaaagcatga catttcagca taatgaacat ttactcatgt ctattttcgt    420
tcttttctgt atgaaaatag ttatttcgag tctctacgga aatagcgaga gatgatatac    480
ctaaatagag ataaaatcat ctcaaaaaaa tgggtctact aaaatattat tccatctatt    540
acaataaatt cacagaatag tcttttaagt aagtctactc tgaatttttt taaaaggaga    600
gggtaactag tggccccaaa aaagaaacgc aaggttatgg ataaaaaata cagcattggt    660
ctggatatcg gaaccaacag cgttgggtgg gcagtaataa cagatgaata caaagtgccg    720
tcaaaaaaat ttaaggttct ggggaataca gatcgccaca gcataaaaaa gaatctgatt    780
ggggcattgc tgtttgattc gggtgagaca gctgaggcca cgcgtctgaa acgtacagca    840
agaagacgtt acacacgtcg taaaaatcgt atttgctact tacaggaaat tttttctaac    900
gaaatggcca aggtagatga tagtttcttc catcgtctcg aagaatcttt tctggttgag    960
gaagataaaa aacacgaacg tcaccctatc tttggcaata tcgtggatga agtggcctat   1020
catgaaaaat accctacgat ttatcatctt cgcaagaagt tggttgatag tacggacaaa   1080
gcggatctgc gtttaatcta tcttgcgtta gcgcacatga tcaaatttcg tggtcatttc   1140
ttaattgaag gtgatctgaa tcctgataac tctgatgtgg acaaattgtt tatacaatta   1200
gtgcaaacct ataatcagct gttcgaggaa aaccccatta atgcctctgg agttgatgcc   1260
aaagcgattt taagcgcgag actttctaag tcccggcgtc tggagaatct gatcgcccag   1320
ttaccagggg aaaagaaaaa tggtctgttt ggtaatctga ttgccctcag tctggggctt   1380
accccgaact tcaaatccaa ttttgacctg gctgaggacg caaagctgca gctgagcaaa   1440
gatacttatg atgatgacct cgacaatctg ctcgcccaga ttggtgacca atatgcggat   1500
ctgtttctgg cagcgaagaa tctttcggat gctatcttgc tgtcggatat tctgcgtgtt   1560
aataccgaaa tcaccaaagc gcctctgtct gcaagtatga tcaagagata cgacgagcac   1620
caccaggacc tgactcttct taaggcactg gtacgccaac agcttccgga gaaatacaaa   1680
gaaatattct tcgaccagtc caagaatggt tacgcgggct acatcgatgg tggtgcatca   1740
caggaagagt tctataaatt tattaaacca atccttgaga aaatggatgg cacggaagag   1800
ttacttgtta aacttaaccg cgaagacttg cttagaaagc aacgtacatt cgacaacggc   1860
tccatcccac accagattca tttaggtgaa cttcacgcca tcttgcgcag acaagaagat   1920
ttctatccct tcttaaaaga caatcgggag aaaatcgaga agatcctgac gttccgcatt   1980
ccctattatg tcggtcccct ggcacgtggt aattctcggt ttgcctggat gacgcgcaaa   2040
agtgaggaaa ccatcacccc ttggaacttt gaagaagtcg tggataaagg tgctagcgcg   2100
cagtctttta tagaaagaat gacgaacttc gataaaaact tgcccaacga aaaagtcctg   2160
```

```
cccaagcact ctcttttata tgagtacttt actgtgtaca acgaactgac taaagtgaaa   2220

tacgttacgg aaggtatgcg caaacctgcc tttcttagtg gcgagcagaa aaaagcaatt   2280

gtcgatcttc tctttaaaac gaatcgcaag gtaactgtaa aacagctgaa ggaagattat   2340

ttcaaaaaga tcgaatgctt tgattctgtc gagatctcgg gtgtcgaaga tcgtttcaac   2400

gcttccttag ggacctatca tgatttgctg aagataataa aagacaaaga ctttctcgac   2460

aatgaagaaa atgaagatat tctggaggat attgttttga ccttgacctt attcgaagat   2520

agagagatga tcgaggagcg cttaaaaacc tatgcccacc tgtttgatga caaagtcatg   2580

aagcaattaa agcgccgcag atatacgggg tggggccgct tgagccgcaa gttgattaac   2640

ggtattagag acaagcagag cggaaaaact atcctggatt tcctcaaatc tgacggattt   2700

gcgaaccgca attttatgca gcttatacat gatgattcgc ttacattcaa agaggatatt   2760

cagaaggctc aggtgtctgg gcaaggtgat tcactccacg aacatatagc aaatttggcc   2820

ggctctcctg cgattaagaa ggggatcctg caaacagtta aagttgtgga tgaacttgta   2880

aaagtaatgg gccgccacaa gccggagaat atcgtgatag aaatggcgcg cgagaatcaa   2940

acgacacaaa aaggtcaaaa gaactcaaga gagagaatga agcgcattga ggaggggata   3000

aaggaacttg gatctcaaat tctgaaagaa catccagttg aaaacactca gctgcaaaat   3060

gaaaaattgt acctgtacta cctgcagaat ggaagagaca tgtacgtgga tcaggaattg   3120

gatatcaata gactctcgga ctatgacgta gatcacattg tccctcagag cttcctcaag   3180

gatgattcta tagataataa agtacttacg agatcggaca aaaatcgcgg taaatcggat   3240

aacgtcccat cggaggaagt cgttaaaaag atgaaaaact attggcgtca actgctgaac   3300

gccaagctga tcacacagcg taagtttgat aatctgacta aagccgaacg cggtggtctt   3360

agtgaactcg ataaagcagg atttataaaa cggcagttag tagaaacgcg ccaaattacg   3420

aaacacgtgg ctcagatcct cgattctaga atgaatacaa agtacgatga aaacgataaa   3480

ctgatccgtg aagtaaaagt cattacctta aaatctaaac ttgtgtccga tttccgcaaa   3540

gattttcagt tttacaaggt ccgggaaatc aataactatc accatgcaca tgatgcatat   3600

ttaaatgcgg ttgtaggcac ggcccttatt aagaaatacc ctaaactcga aagtgagttt   3660

gtttatgggg attataaagt gtatgacgtt cgcaaaatga tcgcgaaatc agaacaggaa   3720

atcggtaagg ctaccgctaa atactttttt tattccaaca ttatgaattt ttttaagacc   3780

gaaataactc tcgcgaatgg tgaaatccgt aaacggcctc ttatagaaac caatggtgaa   3840

acgggagaaa tcgtttggga taaaggtcgt gactttgcca ccgttcgtaa agtcctctca   3900

atgccgcaag ttaacattgt caagaagacg gaagttcaaa caggggggatt ctccaaagaa   3960

tctatcctgc cgaagcgtaa cagtgataaa cttattgcca gaaaaaaaga ttgggatcca   4020

aaaaaatacg gaggctttga ttcccctacc gtcgcgtata gtgtgctggt ggttgctaaa   4080

gtcgagaaag ggaaaagcaa gaaattgaaa tcagttaaag aactgctggg tattacaatt   4140

atggaaagat cgtcctttga gaaaaatccg atcgactttt tagaggccaa ggggtataag   4200

gaagtgaaaa aagatctcat catcaaatta ccgaagtata gtctttttga gctggaaaac   4260

ggcagaaaaa gaatgctggc ctccgcgggc gagttacaga agggaaatga gctggcgctg   4320

ccttccaaat atgttaattt tctgtacctt gccagtcatt atgagaaact gaagggcagc   4380

cccgaagata acgaacagaa acaattattc gtggaacagc ataagcacta tttagatgaa   4440

attatagagc aaattagtga attttctaag cgcgttatcc tcgcggatgc taatttagac   4500
```

```
aaagtactgt cagcttataa taaacatcgg gataagccga ttagagaaca ggccgaaaat   4560
atcattcatt tgtttacctt aaccaacctt ggagcaccag ctgccttcaa atatttcgat   4620
accacaattg atcgtaaacg gtatacaagt acaaaagaag tcttggacgc aaccctcatt   4680
catcaatcta ttactggatt atatgagaca cgcattgatc tttcacagct gggcggagac   4740
aagaagaaaa aactgaaact gcaccatcat caccatcatc atcaccatca ttgataactc   4800
gagaaagctt acataaaaaa ccggccttgg ccccgccggt tttttattat ttttcttcct   4860
ccgcatgttc aatccgctcc ataatcgacg gatggctccc tctgaaaatt ttaacgagaa   4920
acggcgggtt gacccggctc agtcccgtaa cggccaagtc ctgaaacgtc tcaatcgccg   4980
cttcccggtt tccggtcagc tcaatgccgt aacggtcggc ggcgttttcc tgataccggg   5040
agacggcatt cgtaatcgaa ttcgcggccg cacgcgtcca tggggatccc cgcgggtcga   5100
cctcgagagt tacgctaggg ataacagggt aatataggag ctccagtcgg cttaaaccag   5160
ttttcgctgg tgcgaaaaaa gagtgtcttg tgacacctaa attcaaaatc tatcggtcag   5220
atttataccg atttgatttt atatattctt gaataacata cgccgagtta tcacataaaa   5280
gcgggaacca atcataaaat ttaaacttca ttgcataatc cattaaactc ttaaattcta   5340
cgattccttg ttcatcaata aactcaatca tttctttaat taatttatat ctatctgttg   5400
ttgttttctt taataattca ttaacatcta caccgccata aactatcata tcttcttttt   5460
gatatttaaa tttattagga tcgtccatgt gaagcatata tctcacaaga cctttcacac   5520
ttcctgcaat ctgcggaata gtcgcattca attcttctgt taattatttt tatctgttca   5580
taagatttat taccctcata catcactaga atatgataat gctctttttt catcctacct   5640
tctgtatcag tatccctatc atgtaatgga gacactacaa attgaatgtg taactctttt   5700
aaatactcta accactcggc ttttgctgat tctggatata aaacaaatgt ccaattacgt   5760
cctcttgaat ttttcttgtt ttcagtttct tttattacat tttcgctcat gatataataa   5820
cggtgctaat acacttaaca aaatttagtc atagataggc agcatgccag tgctgtctat   5880
cttttttttgt ttaaaatgca ccgtattcct cctttgcata tttttttatt agaataccgg   5940
ttgcatctga tttgctaata ttatattttt ctttgattct atttaatatc tcattttctt   6000
ctgttgtaag tcttaaagta acagcaactt ttttctcttc ttttctatct acaactatca   6060
ctgtacctcc caacatctgt ttttttcact ttaacataaa aaacaacctt ttaacattaa   6120
aaacccaata tttatttatt tgtttggaca atggacactg gacacctagg ggggaggtcg   6180
tagtaccccc ctatgttttc tcccctaaat aaccccaaaa atctaagaaa aaaagacctc   6240
aaaaaggtct ttaattaaca tctcaaattt cgcatttatt ccaatttcct ttttgcgtgt   6300
gatgcgagct catcggctcc gtcgatacta tgttatacgc caactttcaa aacaactttg   6360
aaaaagctgt ttctggtat ttaaggtttt agaatgcaag gaacagtgaa ttggagttcg   6420
tcttgttata attagcttct tggggtatct ttaaatactg tagaaaagag gaaggaaata   6480
ataaatggct aaaatgagaa tatcaccgga attgaaaaaa ctgatcgaaa aataccgctg   6540
cgtaaaagat acggaaggaa tgtctcctgc taaggtatat aagctggtgg gagaaaatga   6600
aaacctatat ttaaaaatga cggacagccg gtataaaggg accacctatg atgtggaacg   6660
ggaaaaggac atgatgctat ggctggaagg aaagctgcct gttccaaagg tcctgcactt   6720
tgaacggcat gatggctgga gcaatctgct catgagtgag gccgatggcg tcctttgctc   6780
ggaagagtat gaagatgaac aaagccctga aaagattatc gagctgtatg cggagtgcat   6840
caggctcttt cactccatcg acatatcgga ttgtccctat acgaatagct tagacagccg   6900
```

```
cttagccgaa ttggattact tactgaataa cgatctggcc gatgtggatt gcgaaaactg   6960

ggaagaagac actccattta aagatccgcg cgagctgtat gattttttaa agacggaaaa   7020

gcccgaagag gaacttgtct tttcccacgg cgacctggga gacagcaaca tctttgtgaa   7080

agatggcaaa gtaagtggct ttattgatct tgggagaagc ggcagggcgg acaagtggta   7140

tgacattgcc ttctgcgtcc ggtcgatcag ggaggatatc ggggaagaac agtatgtcga   7200

gctatttttt gacttactgg ggatcaagcc tgattgggag aaaataaaat attatatttt   7260

actggatgaa ttgttttagt gactgcagtg agatctggta atgactctct agcttgaggc   7320

atcaaataaa acgaaaggct cagtcgaaag actgggcctt tcgttttatc tgttgtttgt   7380

cggtgaacgc tctcctgagt aggacaaatc cgccgctcta gctaagcaga aggccatcct   7440

gacggatggc ctttttgcgt ttctacaaac tcttgttaac tctagagctg cctgccgcgt   7500

ttcggtgatg aagatcttcc cgatgattaa ttaattcaga acgctcggtt gccgccgggc   7560

gtttttttatg aagcttcgtt gctggcgttt ttccataggc tccgcccccc tgacgagcat   7620

cacaaaaatc gacgctcaag tcagaggtgg cgaaacccga caggactata aagataccag   7680

gcgtttcccc ctggaagctc cctcgtgcgc tctcctgttc cgaccctgcc gcttaccgga   7740

tacctgtccg cctttctccc ttcgggaagc gtggcgcttt ctcatagctc acgctgtagg   7800

tatctcagtt cggtgtaggt cgttcgctcc aagctgggct gtgtgcacga accccccgtt   7860

cagcccgacc gctgcgcctt atccggtaac tatcgtcttg agtccaaccc ggtaagacac   7920

gacttatcgc cactggcagc agccactggt aacaggatta gcagagcgag gtatgtaggc   7980

ggtgctacag agttcttgaa gtggtggcct aactacggct acactagaag gacagtattt   8040

ggtatctgcg ctctgctgaa gccagttacc ttcggaaaaa gagttggtag ctcttgatcc   8100

ggcaaacaaa ccaccgctgg tagcggtggt ttttttgttt gcaagcagca gattacgcgc   8160

agaaaaaaag gatctcaaga agatcctttg atcttttcta cggggtctga cgctcagtgg   8220

aacgaaaact cacgttaagg gattttggtc atgagattat caaaaaggat cttcacctag   8280

atccttttaa attaaaaatg aagttttaaa tcaatctaaa gtatatatga gtaaacttgg   8340

tctgaca                                                             8347
```

<210> SEQ ID NO 22
<211> LENGTH: 846
<212> TYPE: DNA
<213> ORGANISM: Bacillus licheniformis

<400> SEQUENCE: 22

```
gtgaacagat cctttaccgt tgaaaaggta ctcaacaaca acgttttaat cgctctccat     60

gatgattaca gagaagttgt cttgattggc aaaggaatcg gttttggtaa aaagcgcgga    120

gatcttatcg aacatgagaa ctacgaaaaa atgtttatcc tggaaaatga taaggaacaa    180

tcgcagtata agaagctcct cacttatgtc gatgaaaaaa tggttgatat cgccaatgat    240

gtcatctacc atatcgcgca aaaaatcggc cagccgctga acgaacacat tcatgtcgcc    300

ctgacggacc atatcgcatt tgcagttaag cgtctagaaa agggatttga tatgaaaaat    360

ccgtttttgc ttgagacgga atcgctttat ccgaaggaat acgaagtcgc caaggaagcc    420

gtcgatatga ttaatgaaaa atccgacatt cagctgcctg aaggtgaaat cgggttcatc    480

gcgcttcata tccacagtgc gatgacaaac cgcccgcttt ctgaagtcaa tcagcattca    540

caactgatct ccaggcttgt ccaggtcatc gaagattcat tccagatgca agtcaacagg    600
```

gaaagcgtga actatttgcg gctgatcagg cacttgcgct ttacgattga caggataaaa 660
cgggacgagc cgattcagga accggaaaaa ttaatgttgt tgttgaaaac ggaatatccg 720
ctgtgttaca atactgcttg gaagatgatc aagatcttgc agcaagcgct caagaaaccg 780
gttcatgagg cagaagccgt ttatttgaca ttgcatttgt accgtttgac taataaaatt 840
tcataa 846

<210> SEQ ID NO 23
<211> LENGTH: 23
<212> TYPE: DNA
<213> ORGANISM: Bacillus licheniformis

<400> SEQUENCE: 23 tttttcatc gacataagtg agg 23

<210> SEQ ID NO 24
<211> LENGTH: 20
<212> TYPE: DNA
<213> ORGANISM: Artificial Sequence
<220> FEATURE:
<223> OTHER INFORMATION: glcT VT domain

<400> SEQUENCE: 24 tttttcatc gacataagtg 20

<210> SEQ ID NO 25
<211> LENGTH: 3
<212> TYPE: DNA
<213> ORGANISM: Artificial Sequence
<220> FEATURE:
<223> OTHER INFORMATION: glcT target site PAM sequence

<400> SEQUENCE: 25 agg 3

<210> SEQ ID NO 26
<211> LENGTH: 76
<212> TYPE: DNA
<213> ORGANISM: Artificial Sequence
<220> FEATURE:
<223> OTHER INFORMATION: Cas9 endonuclease recognition domain

<400> SEQUENCE: 26
gttttagagc tagaaatagc aagttaaaat aaggctagtc cgttatcaac ttgaaaaagt 60
ggcaccgagt cggtgc 76

<210> SEQ ID NO 27
<211> LENGTH: 96
<212> TYPE: RNA
<213> ORGANISM: Artificial Sequence
<220> FEATURE:
<223> OTHER INFORMATION: glcT RNA

<400> SEQUENCE: 27
uuuuuucauc gacauaagug guuuuagagc uagaaauagc aaguuaaaau aaggcuaguc 60
cguuaucaac uugaaaaagu ggcaccgagu cggugc 96

<210> SEQ ID NO 28
<211> LENGTH: 96
<212> TYPE: DNA
<213> ORGANISM: Artificial Sequence
<220> FEATURE:
<223> OTHER INFORMATION: DNA encoding glcT gRNA

<400> SEQUENCE: 28

```
tttttcatc gacataagtg gttttagagc tagaaatagc aagttaaaat aaggctagtc     60

cgttatcaac ttgaaaaagt ggcaccgagt cggtgc                              96
```

<210> SEQ ID NO 29
<211> LENGTH: 93
<212> TYPE: DNA
<213> ORGANISM: Bacillus subtilis

<400> SEQUENCE: 29

```
tcgctgataa acagctgaca tcaactaaaa gcttcattaa atactttgaa aaaagttgtt     60

gacttaaaag aagctaaatg ttatagtaat aaa                                 93
```

<210> SEQ ID NO 30
<211> LENGTH: 95
<212> TYPE: DNA
<213> ORGANISM: lambda phage

<400> SEQUENCE: 30

```
gactcctgtt gatagatcca gtaatgacct cagaactcca tctggatttg ttcagaacgc     60

tcggttgccg ccgggcgttt tttattggtg agaat                               95
```

<210> SEQ ID NO 31
<211> LENGTH: 284
<212> TYPE: DNA
<213> ORGANISM: Artificial Sequence
<220> FEATURE:
<223> OTHER INFORMATION: glcT gRNA expression cassette

<400> SEQUENCE: 31

```
tcgctgataa acagctgaca tcaactaaaa gcttcattaa atactttgaa aaaagttgtt     60

gacttaaaag aagctaaatg ttatagtaat aaattttttc atcgacataa gtggttttag    120

agctagaaat agcaagttaa aataaggcta gtccgttatc aacttgaaaa agtggcaccg    180

agtcggtgcg actcctgttg atagatccag taatgacctc agaactccat ctggatttgt    240

tcagaacgct cggttgccgc cgggcgtttt ttattggtga gaat                     284
```

<210> SEQ ID NO 32
<211> LENGTH: 500
<212> TYPE: DNA
<213> ORGANISM: Bacillus licheniformis

<400> SEQUENCE: 32

```
taagctgtga caaccagccg atcagcgaag tgctcggcat ttcaacaatt gaaatcaata     60

taaaggaaat ggggaagcgc gcgtttcgcc ttctgcaaaa aagaatcggc ggcgccgggc    120

cggaaaaact gactgttcct tacaagctga tcaaaagggc gactgtgtaa tcaaaacatc    180

aatctttttc cagacagtga tcaaaattcg acatttttca tcaaaaacgt caaaataaat    240

tgacgcgctt tcatgagttt tgtacgatat gagagattga tgacaaaaag gagctgagga    300

tcgtgaacag atcctttacc gttgaaaagg tactcaacaa caacgtttta atcgctctcc    360

atgatgatta cagagaagtt gtcttgattg gcaaaggaat cggttttggt aaaaagcgcg    420

gagatcttat cgaacatgag aactacgaaa aaatgtttat cctggaaaat gataaggaac    480

aatcgcagta taagaagctc                                                500
```

<210> SEQ ID NO 33

<211> LENGTH: 38
<212> TYPE: DNA
<213> ORGANISM: Artificial Sequence
<220> FEATURE:
<223> OTHER INFORMATION: glcT 5' forward primer

<400> SEQUENCE: 33
tgagtaaact tggtctgaca taagctgtga caaccagc 38

<210> SEQ ID NO 34
<211> LENGTH: 45
<212> TYPE: DNA
<213> ORGANISM: Artificial Sequence
<220> FEATURE:
<223> OTHER INFORMATION: glcT 5' reverse primer

<400> SEQUENCE: 34 ccatttttc atcgacataa gtgaagagct tcttatactg cgatt 45

<210> SEQ ID NO 35
<211> LENGTH: 500
<212> TYPE: DNA
<213> ORGANISM: Bacillus licheniformis

<400> SEQUENCE: 35
tcacttatgt cgatgaaaaa atggttgata tcgccaatga tgtcatctac catatcgcgc 60
aaaaaatcgg ccagccgctg aacgaacaca ttcatgtcgc cctgacggac catatcgcat 120
ttgcagttaa gcgtctagaa aagggatttg atatgaaaaa tccgtttttg cttgagacgg 180
aatcgcttta tccgaaggaa tacgaagtcg ccaaggaagc cgtcgatatg attaatgaaa 240
aatccgacat tcagctgcct gaaggtgaaa tcgggttcat cgcgcttcat atccacagtg 300
cgatgacaaa ccgcccgctt tctgaagtca atcagcattc acaactgatc tccaggcttg 360
tccaggtcat cgaagattca ttccagatgc aagtcaacag ggaaagcgtg aactatttgc 420
ggctgatcag gcacttgcgc tttacgattg acaggataaa acgggacgag ccgattcagg 480
aaccggaaaa attaatgttg 500

<210> SEQ ID NO 36
<211> LENGTH: 45
<212> TYPE: DNA
<213> ORGANISM: Artificial Sequence
<220> FEATURE:
<223> OTHER INFORMATION: glcT 3' forward primer

<400> SEQUENCE: 36
aatcgcagta taagaagctc ttcacttatg tcgatgaaaa aatgg 45

<210> SEQ ID NO 37
<211> LENGTH: 46
<212> TYPE: DNA
<213> ORGANISM: Artificial Sequence
<220> FEATURE:
<223> OTHER INFORMATION: glcT 3' reverse primer

<400> SEQUENCE: 37
cagaagaaaa tggaggaatt ccaacattaa tttttccggt tcctga 46

<210> SEQ ID NO 38
<211> LENGTH: 9632
<212> TYPE: DNA
<213> ORGANISM: Artificial Sequence
<220> FEATURE:
<223> OTHER INFORMATION: pRF731

<400> SEQUENCE: 38

```
tcgctgataa acagctgaca tcaactaaaa gcttcattaa atactttgaa aaaagttgtt     60
gacttaaaag aagctaaatg ttatagtaat aaattttttc atcgacataa gtggttttag    120
agctagaaat agcaagttaa aataaggcta gtccgttatc aacttgaaaa agtggcaccg    180
agtcggtgcg actcctgttg atagatccag taatgacctc agaactccat ctggatttgt    240
tcagaacgct cggttgccgc cgggcgtttt ttattggtga gaatgaattc gcggccgcac    300
gcgtccatgg ggatccccgc gggtcgacct cgagagttac gctagggata acagggtaat    360
ataggagctc cagtcggctt aaaccagttt tcgctggtgc gaaaaaagag tgtcttgtga    420
cacctaaatt caaaatctat cggtcagatt tataccgatt tgattttata tattcttgaa    480
taacatacgc cgagttatca cataaaagcg ggaaccaatc ataaaattta aacttcattg    540
cataatccat taaactctta aattctacga ttccttgttc atcaataaac tcaatcattt    600
ctttaattaa tttatatcta tctgttgttg ttttctttaa taattcatta acatctacac    660
cgccataaac tatcatatct tctttttgat atttaaattt attaggatcg tccatgtgaa    720
gcatatatct cacaagacct ttcacacttc ctgcaatctg cggaatagtc gcattcaatt    780
cttctgttaa ttatttttat ctgttcataa gatttattac cctcatacat cactagaata    840
tgataatgct cttttttcat cctaccttct gtatcagtat ccctatcatg taatggagac    900
actacaaatt gaatgtgtaa ctcttttaaa tactctaacc actcggcttt tgctgattct    960
ggatataaaa caaatgtcca attacgtcct cttgaatttt tcttgttttc agtttctttt   1020
attacatttt cgctcatgat ataataacgg tgctaataca cttaacaaaa tttagtcata   1080
gataggcagc atgccagtgc tgtctatctt tttttgttta aaatgcaccg tattcctcct   1140
ttgcatattt ttttattaga ataccggttg catctgattt gctaatatta tatttttctt   1200
tgattctatt taatatctca ttttcttctg ttgtaagtct taaagtaaca gcaacttttt   1260
tctcttcttt tctatctaca actatcactg tacctcccaa catctgtttt tttcacttta   1320
acataaaaaa caacctttta acattaaaaa cccaatattt atttatttgt ttggacaatg   1380
gacactggac acctaggggg gaggtcgtag taccccccta tgttttctcc cctaaataac   1440
cccaaaaatc taagaaaaaa agacctcaaa aaggtcttta attaacatct caaatttcgc   1500
atttattcca atttcctttt tgcgtgtgat gcgagctcat cggctccgtc gatactatgt   1560
tatacgccaa ctttcaaaac aactttgaaa aagctgtttt ctggtattta aggttttaga   1620
atgcaaggaa cagtgaattg gagttcgtct tgttataatt agcttcttgg ggtatcttta   1680
aatactgtag aaaagaggaa ggaaataata aatggctaaa atgagaatat caccggaatt   1740
gaaaaaactg atcgaaaaat accgctgcgt aaaagatacg gaaggaatgt ctcctgctaa   1800
ggtatataag ctggtgggag aaaatgaaaa cctatattta aaaatgacgg acagccggta   1860
taaagggacc acctatgatg tggaacggga aaaggacatg atgctatggc tggaaggaaa   1920
gctgcctgtt ccaaaggtcc tgcactttga acggcatgat ggctggagca atctgctcat   1980
gagtgaggcc gatggcgtcc tttgctcgga agagtatgaa gatgaacaaa gccctgaaaa   2040
gattatcgag ctgtatgcgg agtgcatcag gctctttcac tccatcgaca tatcggattg   2100
tccctatacg aatagcttag acagccgctt agccgaattg gattacttac tgaataacga   2160
tctggccgat gtggattgcg aaaactggga agaagacact ccatttaaag atccgcgcga   2220
gctgtatgat tttttaaaga cggaaaagcc cgaagaggaa cttgtctttt cccacggcga   2280
```

```
cctgggagac agcaacatct ttgtgaaaga tggcaaagta agtggcttta ttgatcttgg   2340
gagaagcggc agggcggaca agtggtatga cattgccttc tgcgtccggt cgatcaggga   2400
ggatatcggg gaagaacagt atgtcgagct atttttgac ttactgggga tcaagcctga   2460
ttgggagaaa ataaaatatt atattttact ggatgaattg ttttagtgac tgcagtgaga   2520
tctggtaatg actctctagc ttgaggcatc aaataaaacg aaaggctcag tcgaaagact   2580
gggcctttcg ttttatctgt tgtttgtcgg tgaacgctct cctgagtagg acaaatccgc   2640
cgctctagct aagcagaagg ccatcctgac ggatggcctt tttgcgtttc tacaaactct   2700
tgttaactct agagctgcct gccgcgtttc ggtgatgaag atcttcccga tgattaatta   2760
attcagaacg ctcggttgcc gccgggcgtt ttttatgaag cttcgttgct ggcgtttttc   2820
cataggctcc gcccccctga cgagcatcac aaaaatcgac gctcaagtca gaggtggcga   2880
aacccgacag gactataaag ataccaggcg tttccccctg gaagctccct cgtgcgctct   2940
cctgttccga ccctgccgct taccggatac ctgtccgcct ttctcccttc gggaagcgtg   3000
gcgctttctc atagctcacg ctgtaggtat ctcagttcgg tgtaggtcgt tcgctccaag   3060
ctgggctgtg tgcacgaacc ccccgttcag cccgaccgct gcgccttatc cggtaactat   3120
cgtcttgagt ccaacccggt aagacacgac ttatcgccac tggcagcagc cactggtaac   3180
aggattagca gagcgaggta tgtaggcggt gctacagagt tcttgaagtg gtggcctaac   3240
tacggctaca ctagaaggac agtatttggt atctgcgctc tgctgaagcc agttaccttc   3300
ggaaaaagag ttggtagctc ttgatccggc aaacaaacca ccgctggtag cggtggtttt   3360
tttgtttgca agcagcagat tacgcgcaga aaaaaaggat ctcaagaaga tcctttgatc   3420
ttttctacgg ggtctgacgc tcagtggaac gaaaactcac gttaagggat tttggtcatg   3480
agattatcaa aaaggatctt cacctagatc cttttaaatt aaaaatgaag ttttaaatca   3540
atctaaagta tatatgagta aacttggtct gacataagct gtgacaacca gccgatcagc   3600
gaagtgctcg gcatttcaac aattgaaatc aatataaagg aaatggggaa gcgcgcgttt   3660
cgccttctgc aaaaaagaat cggcggcgcc gggccggaaa aactgactgt tccttacaag   3720
ctgatcaaaa gggcgactgt gtaatcaaaa catcaatctt tttccagaca gtgatcaaaa   3780
ttcgacattt ttcatcaaaa acgtcaaaat aaattgacgc gctttcatga gttttgtacg   3840
atatgagaga ttgatgacaa aaaggagctg aggatcgtga acagatcctt taccgttgaa   3900
aaggtactca acaacaacgt tttaatcgct ctccatgatg attacagaga agttgtcttg   3960
attggcaaag gaatcggttt tggtaaaaag cgcggagatc ttatcgaaca tgagaactac   4020
gaaaaaatgt ttatcctgga aaatgataag gaacaatcgc agtataagaa gctcttcact   4080
tatgtcgatg aaaaaatggt tgatatcgcc aatgatgtca tctaccatat cgcgcaaaaa   4140
atcggccagc cgctgaacga acacattcat gtcgccctga cggaccatat cgcatttgca   4200
gttaagcgtc tagaaaaggg atttgatatg aaaaatccgt tttgcttgga gacggaatcg   4260
ctttatccga aggaatacga agtcgccaag gaagccgtcg atatgattaa tgaaaaatcc   4320
gacattcagc tgcctgaagg tgaaatcggg ttcatcgcgc ttcatatcca cagtgcgatg   4380
acaaaccgcc cgctttctga agtcaatcag cattcacaac tgatctccag gcttgtccag   4440
gtcatcgaag attcattcca gatgcaagtc aacagggaaa gcgtgaacta tttgcggctg   4500
atcaggcact tgcgctttac gattgacagg ataaaacggg acgagccgat tcaggaaccg   4560
gaaaaattaa tgttggaatt cctccatttt cttctgctat caaaataaca gactcgtgat   4620
tttccaaacg agctttcaaa aaagcctctg ccccttgcaa atcggatgcc tgtctataaa   4680
```

```
attcccgata ttggttaaac agcggcgcaa tggcggccgc atctgatgtc tttgcttggc   4740
gaatgttcat cttatttctt cctccctctc aataattttt tcattctatc ccttttctgt   4800
aaagtttatt tttcagaata cttttatcat catgctttga aaaaatatca cgataatatc   4860
cattgttctc acggaagcac acgcaggtca tttgaacgaa ttttttcgac aggaatttgc   4920
cgggactcag gagcatttaa cctaaaaaag catgacattt cagcataatg aacatttact   4980
catgtctatt ttcgttcttt tctgtatgaa aatagttatt tcgagtctct acggaaatag   5040
cgagagatga tatacctaaa tagagataaa atcatctcaa aaaaatgggt ctactaaaat   5100
attattccat ctattacaat aaattcacag aatagtcttt taagtaagtc tactctgaat   5160
ttttttaaaa ggagagggta actagtggcc ccaaaaaaga aacgcaaggt tatggataaa   5220
aaatacagca ttggtctgga tatcggaacc aacagcgttg ggtgggcagt aataacagat   5280
gaatacaaag tgccgtcaaa aaaatttaag gttctgggga atacagatcg ccacagcata   5340
aaaaagaatc tgattggggc attgctgttt gattcgggtg agacagctga ggccacgcgt   5400
ctgaaacgta cagcaagaag acgttacaca cgtcgtaaaa atcgtatttg ctacttacag   5460
gaaatttttt ctaacgaaat ggccaaggta gatgatagtt tcttccatcg tctcgaagaa   5520
tctttttctgg ttgaggaaga taaaaaacac gaacgtcacc ctatctttgg caatatcgtg   5580
gatgaagtgg cctatcatga aaaataccct acgatttatc atcttcgcaa gaagttggtt   5640
gatagtacgg acaaagcgga tctgcgttta atctatcttg cgttagcgca catgatcaaa   5700
tttcgtggtc atttcttaat tgaaggtgat ctgaatcctg ataactctga tgtggacaaa   5760
ttgtttatac aattagtgca aacctataat cagctgttcg aggaaaaccc cattaatgcc   5820
tctggagttg atgccaaagc gattttaagc gcgagacttt ctaagtcccg gcgtctggag   5880
aatctgatcg cccagttacc aggggaaaag aaaaatggtc tgtttggtaa tctgattgcc   5940
ctcagtctgg ggcttacccc gaacttcaaa tccaatttttg acctggctga ggacgcaaag   6000
ctgcagctga gcaaagatac ttatgatgat gacctcgaca atctgctcgc ccagattggt   6060
gaccaatatg cggatctgtt tctggcagcg aagaatcttt cggatgctat cttgctgtcg   6120
gatattctgc gtgttaatac cgaaatcacc aaagcgcctc tgtctgcaag tatgatcaag   6180
agatacgacg agcaccacca ggacctgact cttcttaagg cactggtacg ccaacagctt   6240
ccggagaaat acaaagaaat attcttcgac cagtccaaga atggttacgc gggctacatc   6300
gatggtggtg catcacagga agagttctat aaatttatta aaccaatcct tgagaaaatg   6360
gatggcacgg aagagttact tgttaaactt aaccgcgaag acttgcttag aaagcaacgt   6420
acattcgaca acggctccat cccacaccag attcatttag gtgaacttca cgccatcttg   6480
cgcagacaag aagatttcta tcccttctta aaagacaatc gggagaaaat cgagaagatc   6540
ctgacgttcc gcattcccta ttatgtcggt cccctggcac gtggtaattc tcggtttgcc   6600
tggatgacgc gcaaaagtga ggaaaccatc accccttgga actttgaaga agtcgtggat   6660
aaaggtgcta gcgcgcagtc ttttatagaa agaatgacga acttcgataa aaacttgccc   6720
aacgaaaaag tcctgcccaa gcactctctt ttatatgagt actttactgt gtacaacgaa   6780
ctgactaaag tgaaatacgt tacggaaggt atgcgcaaac ctgcctttct tagtggcgag   6840
cagaaaaaag caattgtcga tcttctcttt aaaacgaatc gcaaggtaac tgtaaaacag   6900
ctgaaggaag attatttcaa aaagatcgaa tgctttgatt ctgtcgagat ctcgggtgtc   6960
gaagatcgtt tcaacgcttc cttagggacc tatcatgatt tgctgaagat aataaaagac   7020
```

```
aaagactttc tcgacaatga agaaaatgaa gatattctgg aggatattgt tttgaccttg   7080
accttattcg aagatagaga gatgatcgag gagcgcttaa aaacctatgc ccacctgttt   7140
gatgacaaag tcatgaagca attaaagcgc cgcagatata cggggtgggg ccgcttgagc   7200
cgcaagttga ttaacggtat tagagacaag cagagcggaa aaactatcct ggatttcctc   7260
aaatctgacg gatttgcgaa ccgcaatttt atgcagctta tacatgatga ttcgcttaca   7320
ttcaaagagg atattcagaa ggctcaggtg tctgggcaag gtgattcact ccacgaacat   7380
atagcaaatt tggccggctc tcctgcgatt aagaagggga tcctgcaaac agttaaagtt   7440
gtggatgaac ttgtaaaagt aatgggccgc cacaagccgg agaatatcgt gatagaaatg   7500
gcgcgcgaga atcaaacgac acaaaaaggt caaaagaact caagagagag aatgaagcgc   7560
attgaggagg ggataaagga acttggatct caaattctga aagaacatcc agttgaaaac   7620
actcagctgc aaaatgaaaa attgtacctg tactacctgc agaatggaag agacatgtac   7680
gtggatcagg aattggatat caatagactc tcggactatg acgtagatca cattgtccct   7740
cagagcttcc tcaaggatga ttctatagat aataaagtac ttacgagatc ggacaaaaat   7800
cgcggtaaat cggataacgt cccatcggag gaagtcgtta aaaagatgaa aaactattgg   7860
cgtcaactgc tgaacgccaa gctgatcaca cagcgtaagt ttgataatct gactaaagcc   7920
gaacgcggtg gtcttagtga actcgataaa gcaggattta taaaacggca gttagtagaa   7980
acgcgccaaa ttacgaaaca cgtggctcag atcctcgatt ctagaatgaa tacaaagtac   8040
gatgaaaacg ataaactgat ccgtgaagta aaagtcatta ccttaaaatc taaacttgtg   8100
tccgatttcc gcaaagattt tcagttttac aaggtccggg aaatcaataa ctatcaccat   8160
gcacatgatg catatttaaa tgcggttgta ggcacggccc ttattaagaa ataccctaaa   8220
ctcgaaagtg agtttgttta tggggattat aaagtgtatg acgttcgcaa aatgatcgcg   8280
aaatcagaac aggaaatcgg taaggctacc gctaaatact ttttttattc caacattatg   8340
aattttttta agaccgaaat aactctcgcg aatggtgaaa tccgtaaacg gcctcttata   8400
gaaaccaatg gtgaaacggg agaaatcgtt tgggataaag gtcgtgactt tgccaccgtt   8460
cgtaaagtcc tctcaatgcc gcaagttaac attgtcaaga agacggaagt tcaaacaggg   8520
ggattctcca aagaatctat cctgccgaag cgtaacagtg ataaacttat tgccagaaaa   8580
aaagattggg atccaaaaaa atacggaggc tttgattccc ctaccgtcgc gtatagtgtg   8640
ctggtggttg ctaaagtcga gaaagggaaa agcaagaaat tgaaatcagt taaagaactg   8700
ctgggtatta caattatgga aagatcgtcc tttgagaaaa atccgatcga ctttttagag   8760
gccaaggggt ataaggaagt gaaaaaagat ctcatcatca aattaccgaa gtatagtctt   8820
tttgagctgg aaaacggcag aaaaagaatg ctggcctccg cgggcgagtt acagaaggga   8880
aatgagctgg cgctgccttc caaatatgtt aattttctgt accttgccag tcattatgag   8940
aaactgaagg gcagccccga agataacgaa cagaaacaat tattcgtgga acagcataag   9000
cactatttag atgaaattat agagcaaatt agtgaatttt ctaagcgcgt tatcctcgcg   9060
gatgctaatt tagacaaagt actgtcagct tataataaac atcgggataa gccgattaga   9120
gaacaggccg aaaatatcat tcatttgttt accttaacca accttggagc accagctgcc   9180
ttcaaatatt tcgataccac aattgatcgt aaacggtata caagtacaaa agaagtcttg   9240
gacgcaaccc tcattcatca atctattact ggattatatg agacacgcat tgatctttca   9300
cagctgggcg gagacaagaa gaaaaaactg aaactgcacc atcatcacca tcatcatcac   9360
catcattgat aactcgagaa agcttacata aaaaaccggc cttggccccg ccggtttttt   9420
```

```
attatttttc ttcctccgca tgttcaatcc gctccataat cgacggatgg ctccctctga   9480

aaattttaac gagaaacggc gggttgaccc ggctcagtcc cgtaacggcc aagtcctgaa   9540

acgtctcaat cgccgcttcc cggtttccgg tcagctcaat gccgtaacgg tcggcggcgt   9600

tttcctgata ccgggagacg gcattcgtaa tc                                 9632
```

<210> SEQ ID NO 39
<211> LENGTH: 9632
<212> TYPE: DNA
<213> ORGANISM: Artificial Sequence
<220> FEATURE:
<223> OTHER INFORMATION: pRF724

<400> SEQUENCE: 39

```
gaattcctcc attttcttct gctatcaaaa taacagactc gtgattttcc aaacgagctt     60

tcaaaaaagc ctctgcccct tgcaaatcgg atgcctgtct ataaaattcc cgatattggt    120

taaacagcgg cgcaatggcg gccgcatctg atgtctttgc ttggcgaatg ttcatcttat    180

ttcttcctcc ctctcaataa tttttcatt ctatcccttt tctgtaaagt ttatttttca    240

gaatactttt atcatcatgc tttgaaaaaa tatcacgata atatccattg ttctcacgga    300

agcacacgca ggtcatttga acgaattttt tcgacaggaa tttgccggga ctcaggagca    360

tttaacctaa aaaagcatga catttcagca taatgaacat ttactcatgt ctattttcgt    420

tcttttctgt atgaaaatag ttatttcgag tctctacgga aatagcgaga gatgatatac    480

ctaaatagag ataaaatcat ctcaaaaaaa tgggtctact aaaatattat tccatctatt    540

acaataaatt cacagaatag tcttttaagt aagtctactc tgaatttttt taaaaggaga    600

gggtaactag tggccccaaa aaagaaacgc aaggttatgg ataaaaaata cagcattggt    660

ctggatatcg gaaccaacag cgttgggtgg gcagtaataa cagatgaata caaagtgccg    720

tcaaaaaaat ttaaggttct ggggaataca gatcgccaca gcataaaaaa gaatctgatt    780

ggggcattgc tgtttgattc gggtgagaca gctgaggcca cgcgtctgaa acgtacagca    840

agaagacgtt acacacgtcg taaaaatcgt atttgctact tacaggaaat tttttctaac    900

gaaatggcca aggtagatga tagtttcttc catcgtctcg aagaatcttt tctggttgag    960

gaagataaaa aacacgaacg tcaccctatc tttggcaata tcgtggatga agtggcctat   1020

catgaaaaat accctacgat ttatcatctt cgcaagaagt tggttgatag tacggacaaa   1080

gcggatctgc gtttaatcta tcttgcgtta gcgcacatga tcaaatttcg tggtcatttc   1140

ttaattgaag gtgatctgaa tcctgataac tctgatgtgg acaaattgtt tatacaatta   1200

gtgcaaacct ataatcagct gttcgaggaa aaccccatta atgcctctgg agttgatgcc   1260

aaagcgattt taagcgcgag actttctaag tcccggcgtc tggagaatct gatcgcccag   1320

ttaccagggg aaaagaaaaa tggtctgttt ggtaatctga ttgccctcag tctggggctt   1380

accccgaact tcaaatccaa ttttgacctg gctgaggacg caaagctgca gctgagcaaa   1440

gatacttatg atgatgacct cgacaatctg ctcgcccaga ttggtgacca atatgcggat   1500

ctgtttctgg cagcgaagaa tctttcggat gctatcttgc tgtcggatat tctgcgtgtt   1560

aataccgaaa tcaccaaagc gcctctgtct gcaagtatga tcaagagata cgacgagcac   1620

caccaggacc tgactcttct taaggcactg gtacgccaac agcttccgga gaaatacaaa   1680

gaaatattct tcgaccagtc caagaatggt tacgcgggct acatcgatgg tggtgcatca   1740

caggaagagt tctataaatt tattaaacca atccttgaga aaatggatgg cacggaagag   1800
```

-continued

```
ttacttgtta aacttaaccg cgaagacttg cttagaaagc aacgtacatt cgacaacggc   1860
tccatcccac accagattca tttaggtgaa cttcacgcca tcttgcgcag acaagaagat   1920
ttctatccct tcttaaaaga caatcgggag aaaatcgaga agatcctgac gttccgcatt   1980
ccctattatg tcggtcccct ggcacgtggt aattctcggt ttgcctggat gacgcgcaaa   2040
agtgaggaaa ccatcacccc ttggaacttt gaagaagtcg tggataaagg tgctagcgcg   2100
cagtctttta tagaaagaat gacgaacttc gataaaaact tgcccaacga aaaagtcctg   2160
cccaagcact ctcttttata tgagtacttt actgtgtaca acgaactgac taaagtgaaa   2220
tacgttacgg aaggtatgcg caaacctgcc tttcttagtg gcgagcagaa aaaagcaatt   2280
gtcgatcttc tctttaaaac gaatcgcaag gtaactgtaa aacagctgaa ggaagattat   2340
ttcaaaaaga tcgaatgctt tgattctgtc gagatctcgg gtgtcgaaga tcgtttcaac   2400
gcttccttag ggacctatca tgatttgctg aagataataa aagacaaaga ctttctcgac   2460
aatgaagaaa atgaagatat tctggaggat attgttttga ccttgacctt attcgaagat   2520
agagagatga tcgaggagcg cttaaaaacc tatgcccacc tgtttgatga caaagtcatg   2580
aagcaattaa agcgccgcag atatacgggg tggggccgct tgagccgcaa gttgattaac   2640
ggtattagag acaagcagag cggaaaaact atcctggatt tcctcaaatc tgacggattt   2700
gcgaaccgca attttatgca gcttatacat gatgattcgc ttacattcaa agaggatatt   2760
cagaaggctc aggtgtctgg gcaaggtgat tcactccacg aacatatagc aaatttggcc   2820
ggctctcctg cgattaagaa ggggatcctg caaacagtta aagttgtgga tgaacttgta   2880
aaagtaatgg gccgccacaa gccggagaat atcgtgatag aaatggcgcg cgagaatcaa   2940
acgacacaaa aaggtcaaaa gaactcaaga gagagaatga agcgcattga ggaggggata   3000
aaggaacttg gatctcaaat tctgaaagaa catccagttg aaaacactca gctgcaaaat   3060
gaaaaattgt acctgtacta cctgcagaat ggaagagaca tgtacgtgga tcaggaattg   3120
gatatcaata gactctcgga ctatgacgta gatcacattg tccctcagag cttcctcaag   3180
gatgattcta tagataataa agtacttacg agatcggaca aaaatcgcgg taaatcggat   3240
aacgtcccat cggaggaagt cgttaaaaag atgaaaaact attggcgtca actgctgaac   3300
gccaagctga tcacacagcg taagtttgat aatctgacta aagccgaacg cggtggtctt   3360
agtgaactcg ataaagcagg atttataaaa cggcagttag tagaaacgcg ccaaattacg   3420
aaacacgtgg ctcagatcct cgattctaga atgaatacaa agtacgatga aaacgataaa   3480
ctgatccgtg aagtaaaagt cattacctta aaatctaaac ttgtgtccga tttccgcaaa   3540
gattttcagt tttacaaggt ccgggaaatc aataactatc accatgcaca tgatgcatat   3600
ttaaatgcgg ttgtaggcac ggcccttatt aagaaatacc ctaaactcga aagtgagttt   3660
gtttatgggg attataaagt gtatgacgtt cgcaaaatga tcgcgaaatc agaacaggaa   3720
atcggtaagg ctaccgctaa atactttttt tattccaaca ttatgaattt ttttaagacc   3780
gaaataactc tcgcgaatgg tgaaatccgt aaacggcctc ttatagaaac caatggtgaa   3840
acgggagaaa tcgtttggga taaaggtcgt gactttgcca ccgttcgtaa agtcctctca   3900
atgccgcaag ttaacattgt caagaagacg gaagttcaaa caggggggatt ctccaaagaa   3960
tctatcctgc cgaagcgtaa cagtgataaa cttattgcca gaaaaaaaga ttgggatcca   4020
aaaaaatacg gaggctttga ttcccctacc gtcgcgtata gtgtgctggt ggttgctaaa   4080
gtcgagaaag ggaaaagcaa gaaattgaaa tcagttaaag aactgctggg tattacaatt   4140
atggaaagat cgtcctttga gaaaaatccg atcgactttt tagaggccaa ggggtataag   4200
```

```
gaagtgaaaa aagatctcat catcaaatta ccgaagtata gtctttttga gctggaaaac   4260
ggcagaaaaa gaatgctggc ctccgcgggc gagttacaga agggaaatga gctggcgctg   4320
ccttccaaat atgttaattt tctgtacctt gccagtcatt atgagaaact gaagggcagc   4380
cccgaagata acgaacagaa acaattattc gtggaacagc ataagcacta tttagatgaa   4440
attatagagc aaattagtga attttctaag cgcgttatcc tcgcggatgc taatttagac   4500
aaagtactgt cagcttataa taaacatcgg gataagccga ttagagaaca ggccgaaaat   4560
atcattcatt tgtttacctt aaccaacctt ggagcaccag ctgccttcaa atatttcgat   4620
accacaattg atcgtaaacg gtatacaagt acaaaagaag tcttggacgc aaccctcatt   4680
catcaatcta ttactggatt atatgagaca cgcattgatc tttcacagct gggcggagac   4740
aagaagaaaa aactgaaact gcaccatcat caccatcatc atcaccatca ttgataactc   4800
gagaaagctt acataaaaaa ccggccttgg ccccgccggt tttttattat ttttcttcct   4860
ccgcatgttc aatccgctcc ataatcgacg gatggctccc tctgaaaatt ttaacgagaa   4920
acggcgggtt gacccggctc agtcccgtaa cggccaagtc ctgaaacgtc tcaatcgccg   4980
cttcccggtt tccggtcagc tcaatgccgt aacggtcggc ggcgttttcc tgataccggg   5040
agacggcatt cgtaatcgta tgaggaactg atggcatctg caggctatat cagcgcgtct   5100
acagtccagg aagcaagaag cagctatgat tccatttacg acatcgtgtc acagtacgat   5160
ttagaggacc tttctctgtt tgacagcgaa aagtggaagg tgctttcaaa aaaagacatc   5220
gaaaacctgg acaaatattt cgactttctc gtgcaggaag caagcagccg aaacaaaaac   5280
tgaatacttc tccgcggcac actctcctct ctatcatttt cgtctgttta cgatcctgct   5340
gttattttat cccttatgtt aacttttgtc aatatttttc ctgtctaagt atttcctata   5400
gtcaacattt gtattaaaat gttcatatca tgaatttgcg ggggggatgg cgatgacaag   5460
gttcggcgag cggctcaaag agctgaggga acaaagaagc ctgtcggtta atcagcttgc   5520
catgtatgcc ggtgtgagcg ccgcagccat ttccagaatc gaaaacggcc accgcggcgt   5580
tcccaagccc gcgacgatca gaaaattggc cgaggctctg aaaatgccgt acgagcagct   5640
catggatatt gccggttata tgagagctga cgagattcgc gaacagccgc gcggctatgt   5700
cacgatgcag gagatcgcgg ccaagcacgg cgtcgaagac ctgtggctgt ttaaacccga   5760
gaaatgggac tgtttgtccc gcgaagacct gctcaacctc gaacagtatt ttcatttttt   5820
ggttaatgaa gcgaagaagc gccaatcata aaaagccgaa tttccctttt aggagaagtt   5880
cggctttttt cggctgcctt aagcggcatc cggattcggc gtcttgcctt tatgatgctt   5940
aacggggctc agcgcacgct cgagccatcc catgaacaga tcggcgatga tcgccatcag   6000
cgccgtcggg atcgcgcctg ctagaatgat cgctgttccg ttggtcgcgt ttgatcctcg   6060
ctgataaaca gctgacatca actaaaagct tcattaaata ctttgaaaaa agttgttgac   6120
ttaaaagaag ctaaatgtta tagtaataaa aaatggctgc ggctctggaa agttttagag   6180
ctagaaatag caagttaaaa taaggctagt ccgttatcaa cttgaaaaag tggcaccgag   6240
tcggtgcgac tcctgttgat agatccagta atgacctcag aactccatct ggatttgttc   6300
agaacgctcg gttgccgccg ggcgtttttt attggtgaga atgaattcgc ggccgcacgc   6360
gtccatgggg atccccgcgg gtcgacctcg agagttacgc tagggataac agggtaatat   6420
aggagctcca gtcggcttaa accagttttc gctggtgcga aaaaagagtg tcttgtgaca   6480
cctaaattca aaatctatcg gtcagattta taccgatttg attttatata ttcttgaata   6540
```

-continued

```
acatacgccg agttatcaca taaaagcggg aaccaatcat aaaatttaaa cttcattgca   6600
taatccatta aactcttaaa ttctacgatt ccttgttcat caataaactc aatcatttct   6660
ttaattaatt tatatctatc tgttgttgtt ttctttaata attcattaac atctacaccg   6720
ccataaacta tcatatcttc tttttgatat ttaaatttat taggatcgtc catgtgaagc   6780
atatatctca caagaccttt cacacttcct gcaatctgcg gaatagtcgc attcaattct   6840
tctgttaatt atttttatct gttcataaga tttattaccc tcatacatca ctagaatatg   6900
ataatgctct tttttcatcc taccttctgt atcagtatcc ctatcatgta atggagacac   6960
tacaaattga atgtgtaact cttttaaata ctctaaccac tcggcttttg ctgattctgg   7020
atataaaaca aatgtccaat tacgtcctct tgaatttttc ttgttttcag tttcttttat   7080
tacattttcg ctcatgatat aataacggtg ctaatacact taacaaaatt tagtcataga   7140
taggcagcat gccagtgctg tctatctttt tttgtttaaa atgcaccgta ttcctccttt   7200
gcatattttt ttattagaat accggttgca tctgatttgc taatattata tttttctttg   7260
attctattta atatctcatt ttcttctgtt gtaagtctta aagtaacagc aactttttttc  7320
tcttcttttc tatctacaac tatcactgta cctcccaaca tctgtttttt tcactttaac   7380
ataaaaaaca accttttaac attaaaaacc caatatttat ttatttgttt ggacaatgga   7440
cactggacac ctaggggggga ggtcgtagta cccccctatg ttttctcccc taaataaccc  7500
caaaaatcta agaaaaaaag acctcaaaaa ggtctttaat taacatctca aatttcgcat   7560
ttattccaat ttcctttttg cgtgtgatgc gagctcatcg gctccgtcga tactatgtta   7620
tacgccaact ttcaaaacaa ctttgaaaaa gctgttttct ggtatttaag gttttagaat   7680
gcaaggaaca gtgaattgga gttcgtcttg ttataattag cttcttgggg tatctttaaa   7740
tactgtagaa aagaggaagg aaataataaa tggctaaaat gagaatatca ccggaattga   7800
aaaaactgat cgaaaaatac cgctgcgtaa aagatacgga aggaatgtct cctgctaagg   7860
tatataagct ggtgggagaa aatgaaaacc tatatttaaa aatgacggac agccggtata   7920
aagggaccac ctatgatgtg gaacgggaaa aggacatgat gctatggctg gaaggaaagc   7980
tgcctgttcc aaaggtcctg cactttgaac ggcatgatgg ctggagcaat ctgctcatga   8040
gtgaggccga tggcgtcctt tgctcggaag agtatgaaga tgaacaaagc cctgaaaaga   8100
ttatcgagct gtatgcggag tgcatcaggc tctttcactc catcgacata tcggattgtc   8160
cctatacgaa tagcttagac agccgcttag ccgaattgga ttacttactg aataacgatc   8220
tggccgatgt ggattgcgaa aactgggaag aagacactcc atttaaagat ccgcgcgagc   8280
tgtatgattt tttaaagacg gaaaagcccg aagaggaact tgtcttttcc cacggcgacc   8340
tgggagacag caacatcttt gtgaaagatg gcaaagtaag tggctttatt gatcttggga   8400
gaagcggcag ggcggacaag tggtatgaca ttgccttctg cgtccggtcg atcagggagg   8460
atatcgggga agaacagtat gtcgagctat tttttgactt actggggatc aagcctgatt   8520
gggagaaaat aaaatattat attttactgg atgaattgtt ttagtgactg cagtgagatc   8580
tggtaatgac tctctagctt gaggcatcaa ataaaacgaa aggctcagtc gaaagactgg   8640
gcctttcgtt ttatctgttg tttgtcggtg aacgctctcc tgagtaggac aaatccgccg   8700
ctctagctaa gcagaaggcc atcctgacgg atggcctttt tgcgtttcta caaactcttg   8760
ttaactctag agctgcctgc cgcgtttcgg tgatgaagat cttcccgatg attaattaat   8820
tcagaacgct cggttgccgc cgggcgtttt ttatgaagct tcgttgctgg cgtttttcca   8880
taggctccgc ccccctgacg agcatcacaa aaatcgacgc tcaagtcaga ggtggcgaaa   8940
```

```
cccgacagga ctataaagat accaggcgtt tccccctgga agctccctcg tgcgctctcc   9000

tgttccgacc ctgccgctta ccggatacct gtccgccttt ctcccttcgg gaagcgtggc   9060

gctttctcat agctcacgct gtaggtatct cagttcggtg taggtcgttc gctccaagct   9120

gggctgtgtg cacgaacccc ccgttcagcc cgaccgctgc gccttatccg gtaactatcg   9180

tcttgagtcc aacccggtaa gacacgactt atcgccactg gcagcagcca ctggtaacag   9240

gattagcaga gcgaggtatg taggcggtgc tacagagttc ttgaagtggt ggcctaacta   9300

cggctacact agaaggacag tatttggtat ctgcgctctg ctgaagccag ttaccttcgg   9360

aaaaagagtt ggtagctctt gatccggcaa acaaaccacc gctggtagcg gtggtttttt   9420

tgtttgcaag cagcagatta cgcgcagaaa aaaaggatct caagaagatc ctttgatctt   9480

ttctacgggg tctgacgctc agtggaacga aaactcacgt taagggattt tggtcatgag   9540

attatcaaaa aggatcttca cctagatcct tttaaattaa aaatgaagtt ttaaatcaat   9600

ctaaagtata tatgagtaaa cttggtctga ca                                 9632
```

<210> SEQ ID NO 40
<211> LENGTH: 18
<212> TYPE: DNA
<213> ORGANISM: Bacillus licheniformis

<400> SEQUENCE: 40

```
gccgcagcca tttccaga                                                   18
```

<210> SEQ ID NO 41
<211> LENGTH: 417
<212> TYPE: DNA
<213> ORGANISM: Bacillus licheniformis

<400> SEQUENCE: 41

```
atgacaaggt tcggcgagcg gctcaaagag ctgagggaac aaagaagcct gtcggttaat     60

cagcttgcca tgtatgccgg tgtgagcgcc gcagccattt ccagagccgc agccatttcc    120

agaatcgaaa acggccaccg cggcgttccc aagcccgcga cgatcagaaa attggccgag    180

gctctgaaaa tgccgtacga gcagctcatg gatattgccg gttatatgag agctgacgag    240

attcgcgaac agccgcgcgg ctatgtcacg atgcaggaga tcgcggccaa gcacggcgtc    300

gaagacctgt ggctgtttaa acccgagaaa tgggactgtt tgtcccgcga agacctgctc    360

aacctcgaac agtattttca ttttttggtt aatgaagcga agaagcgcca atcataa       417
```

<210> SEQ ID NO 42
<211> LENGTH: 8347
<212> TYPE: DNA
<213> ORGANISM: Artificial Sequence
<220> FEATURE:
<223> OTHER INFORMATION: 8.3kb PCR of pRF694

<400> SEQUENCE: 42

```
gaattcgcgg ccgcacgcgt ccatggggat ccccgcgggt cgacctcgag agttacgcta     60

gggataacag ggtaatatag gagctccagt cggcttaaac cagttttcgc tggtgcgaaa    120

aaagagtgtc ttgtgacacc taaattcaaa atctatcggt cagatttata ccgatttgat    180

tttatatatt cttgaataac atacgccgag ttatcacata aaagcgggaa ccaatcataa    240

aatttaaact tcattgcata atccattaaa ctcttaaatt ctacgattcc ttgttcatca    300

ataaactcaa tcatttcttt aattaattta tatctatctg ttgttgtttt ctttaataat    360
```

```
tcattaacat ctacaccgcc ataaactatc atatcttctt tttgatattt aaatttatta    420
ggatcgtcca tgtgaagcat atatctcaca agacctttca cacttcctgc aatctgcgga    480
atagtcgcat tcaattcttc tgttaattat ttttatctgt tcataagatt tattaccctc    540
atacatcact agaatatgat aatgctcttt tttcatccta ccttctgtat cagtatccct    600
atcatgtaat ggagacacta caaattgaat gtgtaactct tttaaatact ctaaccactc    660
ggcttttgct gattctggat ataaaacaaa tgtccaatta cgtcctcttg aatttttctt    720
gttttcagtt tcttttatta cattttcgct catgatataa taacggtgct aatacactta    780
acaaaattta gtcatagata ggcagcatgc cagtgctgtc tatctttttt tgtttaaaat    840
gcaccgtatt cctcctttgc atattttttt attagaatac cggttgcatc tgatttgcta    900
atattatatt tttctttgat tctatttaat atctcatttt cttctgttgt aagtcttaaa    960
gtaacagcaa ctttttctc ttcttttcta tctacaacta tcactgtacc tcccaacatc   1020
tgtttttttc actttaacat aaaaaacaac cttttaacat taaaaaccca atatttattt   1080
atttgtttgg acaatggaca ctggacacct aggggggagg tcgtagtacc cccctatgtt   1140
ttctcccta aataacccca aaaatctaag aaaaaaagac ctcaaaaagg tctttaatta   1200
acatctcaaa tttcgcattt attccaattt cctttttgcg tgtgatgcga gctcatcggc   1260
tccgtcgata ctatgttata cgccaacttt caaaacaact ttgaaaaagc tgttttctgg   1320
tatttaaggt tttagaatgc aaggaacagt gaattggagt tcgtcttgtt ataattagct   1380
tcttggggta tctttaaata ctgtagaaaa gaggaaggaa ataataaatg gctaaaatga   1440
gaatatcacc ggaattgaaa aaactgatcg aaaaataccg ctgcgtaaaa gatacggaag   1500
gaatgtctcc tgctaaggta tataagctgg tgggagaaaa tgaaaaccta tatttaaaaa   1560
tgacggacag ccggtataaa gggaccacct atgatgtgga acgggaaaag gacatgatgc   1620
tatggctgga aggaaagctg cctgttccaa aggtcctgca ctttgaacgg catgatggct   1680
ggagcaatct gctcatgagt gaggccgatg gcgtcctttg ctcggaagag tatgaagatg   1740
aacaaagccc tgaaaagatt atcgagctgt atgcggagtg catcaggctc tttcactcca   1800
tcgacatatc ggattgtccc tatacgaata gcttagacag ccgcttagcc gaattggatt   1860
acttactgaa taacgatctg gccgatgtgg attgcgaaaa ctgggaagaa gacactccat   1920
ttaaagatcc gcgcgagctg tatgattttt taaagacgga aaagcccgaa gaggaacttg   1980
tcttttccca cggcgacctg ggagacagca acatctttgt gaaagatggc aaagtaagtg   2040
gctttattga tcttgggaga agcggcaggg cggacaagtg gtatgacatt gccttctgcg   2100
tccggtcgat cagggaggat atcggggaag aacagtatgt cgagctattt tttgacttac   2160
tggggatcaa gcctgattgg gagaaaataa aatattatat tttactggat gaattgtttt   2220
agtgactgca gtgagatctg gtaatgactc tctagcttga ggcatcaaat aaaacgaaag   2280
gctcagtcga aagactgggc ctttcgtttt atctgttgtt tgtcggtgaa cgctctcctg   2340
agtaggacaa atccgccgct ctagctaagc agaaggccat cctgacggat ggcctttttg   2400
cgtttctaca aactcttgtt aactctagag ctgcctgccg cgtttcggtg atgaagatct   2460
tcccgatgat taattaattc agaacgctcg gttgccgccg ggcgtttttt atgaagcttc   2520
gttgctggcg tttttccata ggctccgccc ccctgacgag catcacaaaa atcgacgctc   2580
aagtcagagg tggcgaaacc cgacaggact ataaagatac caggcgtttc cccctggaag   2640
ctccctcgtg cgctctcctg ttccgaccct gccgcttacc ggatacctgt ccgcctttct   2700
cccttcggga agcgtggcgc tttctcatag ctcacgctgt aggtatctca gttcggtgta   2760
```

```
ggtcgttcgc tccaagctgg gctgtgtgca cgaacccccc gttcagcccg accgctgcgc   2820

cttatccggt aactatcgtc ttgagtccaa cccggtaaga cacgacttat cgccactggc   2880

agcagccact ggtaacagga ttagcagagc gaggtatgta ggcggtgcta cagagttctt   2940

gaagtggtgg cctaactacg gctacactag aaggacagta tttggtatct gcgctctgct   3000

gaagccagtt accttcggaa aaagagttgg tagctcttga tccggcaaac aaaccaccgc   3060

tggtagcggt ggtttttttg tttgcaagca gcagattacg cgcagaaaaa aaggatctca   3120

agaagatcct ttgatctttt ctacggggtc tgacgctcag tggaacgaaa actcacgtta   3180

agggattttg gtcatgagat tatcaaaaag gatcttcacc tagatccttt taaattaaaa   3240

atgaagtttt aaatcaatct aaagtatata tgagtaaact tggtctgaca gaattcctcc   3300

atttcttct gctatcaaaa taacagactc gtgattttcc aaacgagctt tcaaaaaagc   3360

ctctgcccct tgcaaatcgg atgcctgtct ataaaattcc cgatattggt taaacagcgg   3420

cgcaatggcg gccgcatctg atgtctttgc ttggcgaatg ttcatcttat ttcttcctcc   3480

ctctcaataa ttttttcatt ctatcccttt tctgtaaagt ttatttttca gaatactttt   3540

atcatcatgc tttgaaaaaa tatcacgata atatccattg ttctcacgga agcacacgca   3600

ggtcatttga acgaattttt tcgacaggaa tttgccggga ctcaggagca tttaacctaa   3660

aaaagcatga catttcagca taatgaacat ttactcatgt ctattttcgt tcttttctgt   3720

atgaaaatag ttatttcgag tctctacgga aatagcgaga gatgatatac ctaaatagag   3780

ataaaatcat ctcaaaaaaa tgggtctact aaaatattat tccatctatt acaataaatt   3840

cacagaatag tcttttaagt aagtctactc tgaatttttt taaaaggaga gggtaactag   3900

tggccccaaa aaagaaacgc aaggttatgg ataaaaaata cagcattggt ctggatatcg   3960

gaaccaacag cgttgggtgg gcagtaataa cagatgaata caaagtgccg tcaaaaaaat   4020

ttaaggttct ggggaataca gatcgccaca gcataaaaaa gaatctgatt ggggcattgc   4080

tgtttgattc gggtgagaca gctgaggcca cgcgtctgaa acgtacagca agaagacgtt   4140

acacacgtcg taaaaatcgt atttgctact tacaggaaat tttttctaac gaaatggcca   4200

aggtagatga tagtttcttc catcgtctcg aagaatcttt tctggttgag gaagataaaa   4260

aacacgaacg tcaccctatc tttggcaata tcgtggatga agtggcctat catgaaaaat   4320

accctacgat ttatcatctt cgcaagaagt tggttgatag tacggacaaa gcggatctgc   4380

gtttaatcta tcttgcgtta gcgcacatga tcaaatttcg tggtcatttc ttaattgaag   4440

gtgatctgaa tcctgataac tctgatgtgg acaaattgtt tatacaatta gtgcaaacct   4500

ataatcagct gttcgaggaa aaccccatta atgcctctgg agttgatgcc aaagcgattt   4560

taagcgcgag actttctaag tcccggcgtc tggagaatct gatcgcccag ttaccagggg   4620

aaaagaaaaa tggtctgttt ggtaatctga ttgccctcag tctggggctt accccgaact   4680

tcaaatccaa ttttgacctg gctgaggacg caaagctgca gctgagcaaa gatacttatg   4740

atgatgacct cgacaatctg ctcgcccaga ttggtgacca atatgcggat ctgtttctgg   4800

cagcgaagaa tctttcggat gctatcttgc tgtcggatat tctgcgtgtt aataccgaaa   4860

tcaccaaagc gcctctgtct gcaagtatga tcaagagata cgacgagcac caccaggacc   4920

tgactcttct taaggcactg gtacgccaac agcttccgga gaaatacaaa gaaatattct   4980

tcgaccagtc caagaatggt tacgcgggct acatcgatgg tggtgcatca caggaagagt   5040

tctataaatt tattaaacca atccttgaga aaatggatgg cacggaagag ttacttgtta   5100
```

```
aacttaaccg cgaagacttg cttagaaagc aacgtacatt cgacaacggc tccatcccac   5160
accagattca tttaggtgaa cttcacgcca tcttgcgcag acaagaagat ttctatccct   5220
tcttaaaaga caatcgggag aaaatcgaga agatcctgac gttccgcatt ccctattatg   5280
tcggtcccct ggcacgtggt aattctcggt ttgcctggat gacgcgcaaa agtgaggaaa   5340
ccatcacccc ttggaacttt gaagaagtcg tggataaagg tgctagcgcg cagtctttta   5400
tagaaagaat gacgaacttc gataaaaact tgcccaacga aaaagtcctg cccaagcact   5460
ctcttttata tgagtacttt actgtgtaca acgaactgac taaagtgaaa tacgttacgg   5520
aaggtatgcg caaacctgcc tttcttagtg gcgagcagaa aaaagcaatt gtcgatcttc   5580
tctttaaaac gaatcgcaag gtaactgtaa aacagctgaa ggaagattat ttcaaaaaga   5640
tcgaatgctt tgattctgtc gagatctcgg gtgtcgaaga tcgtttcaac gcttccttag   5700
ggacctatca tgatttgctg aagataataa aagacaaaga ctttctcgac aatgaagaaa   5760
atgaagatat tctggaggat attgttttga ccttgacctt attcgaagat agagagatga   5820
tcgaggagcg cttaaaaacc tatgcccacc tgtttgatga caaagtcatg aagcaattaa   5880
agcgccgcag atatacgggg tggggccgct tgagccgcaa gttgattaac ggtattagag   5940
acaagcagag cggaaaaact atcctggatt tcctcaaatc tgacggattt gcgaaccgca   6000
attttatgca gcttatacat gatgattcgc ttacattcaa agaggatatt cagaaggctc   6060
aggtgtctgg gcaaggtgat tcactccacg aacatatagc aaatttggcc ggctctcctg   6120
cgattaagaa ggggatcctg caaacagtta aagttgtgga tgaacttgta aaagtaatgg   6180
gccgccacaa gccggagaat atcgtgatag aaatggcgcg cgagaatcaa acgacacaaa   6240
aaggtcaaaa gaactcaaga gagagaatga agcgcattga ggaggggata aaggaacttg   6300
gatctcaaat tctgaaagaa catccagttg aaaacactca gctgcaaaat gaaaaattgt   6360
acctgtacta cctgcagaat ggaagagaca tgtacgtgga tcaggaattg gatatcaata   6420
gactctcgga ctatgacgta gatcacattg tccctcagag cttcctcaag gatgattcta   6480
tagataataa agtacttacg agatcggaca aaaatcgcgg taaatcggat aacgtcccat   6540
cggaggaagt cgttaaaaag atgaaaaact attggcgtca actgctgaac gccaagctga   6600
tcacacagcg taagtttgat aatctgacta aagccgaacg cggtggtctt agtgaactcg   6660
ataaagcagg atttataaaa cggcagttag tagaaacgcg ccaaattacg aaacacgtgg   6720
ctcagatcct cgattctaga atgaatacaa agtacgatga aaacgataaa ctgatccgtg   6780
aagtaaaagt cattacctta aaatctaaac ttgtgtccga tttccgcaaa gattttcagt   6840
tttacaaggt ccgggaaatc aataactatc accatgcaca tgatgcatat ttaaatgcgg   6900
ttgtaggcac ggcccttatt aagaaatacc ctaaactcga aagtgagttt gtttatgggg   6960
attataaagt gtatgacgtt cgcaaaatga tcgcgaaatc agaacaggaa atcggtaagg   7020
ctaccgctaa atactttttt tattccaaca ttatgaattt tttaagacc gaaataactc    7080
tcgcgaatgg tgaaatccgt aaacggcctc ttatagaaac caatggtgaa acgggagaaa   7140
tcgtttggga taaaggtcgt gactttgcca ccgttcgtaa agtcctctca atgccgcaag   7200
ttaacattgt caagaagacg gaagttcaaa caggggatt ctccaaagaa tctatcctgc    7260
cgaagcgtaa cagtgataaa cttattgcca gaaaaaaaga ttgggatcca aaaaaatacg   7320
gaggctttga ttcccctacc gtcgcgtata gtgtgctggt ggttgctaaa gtcgagaaag   7380
ggaaaagcaa gaaattgaaa tcagttaaag aactgctggg tattacaatt atggaaagat   7440
cgtcctttga gaaaaatccg atcgactttt tagaggccaa ggggtataag gaagtgaaaa   7500
```

aagatctcat catcaaatta ccgaagtata gtctttttga gctggaaaac ggcagaaaaa 7560
gaatgctggc ctccgcgggc gagttacaga agggaaatga gctggcgctg ccttccaaat 7620
atgttaattt tctgtacctt gccagtcatt atgagaaact gaagggcagc cccgaagata 7680
acgaacagaa acaattattc gtggaacagc ataagcacta tttagatgaa attatagagc 7740
aaattagtga attttctaag cgcgttatcc tcgcggatgc taatttagac aaagtactgt 7800
cagcttataa taaacatcgg gataagccga ttagagaaca ggccgaaaat atcattcatt 7860
tgtttacctt aaccaacctt ggagcaccag ctgccttcaa atatttcgat accacaattg 7920
atcgtaaacg gtatacaagt acaaaagaag tcttggacgc aaccctcatt catcaatcta 7980
ttactggatt atatgagaca cgcattgatc tttcacagct gggcggagac aagaagaaaa 8040
aactgaaact gcaccatcat caccatcatc atcaccatca ttgataactc gagaaagctt 8100
acataaaaaa ccggccttgg ccccgccggt tttttattat ttttcttcct ccgcatgttc 8160
aatccgctcc ataatcgacg gatggctccc tctgaaaatt ttaacgagaa acggcgggtt 8220
gacccggctc agtcccgtaa cggccaagtc ctgaaacgtc tcaatcgccg cttcccggtt 8280
tccggtcagc tcaatgccgt aacggtcggc ggcgttttcc tgataccggg agacggcatt 8340
cgtaatc 8347

<210> SEQ ID NO 43
<211> LENGTH: 17
<212> TYPE: DNA
<213> ORGANISM: Artificial Sequence
<220> FEATURE:
<223> OTHER INFORMATION: pRF694 forward

<400> SEQUENCE: 43
gaattcgcgg ccgcacg 17

<210> SEQ ID NO 44
<211> LENGTH: 29
<212> TYPE: DNA
<213> ORGANISM: Artificial Sequence
<220> FEATURE:
<223> OTHER INFORMATION: pRF694 reverse

<400> SEQUENCE: 44
gattacgaat gccgtctccc ggtatcagg 29

<210> SEQ ID NO 45
<211> LENGTH: 1365
<212> TYPE: DNA
<213> ORGANISM: Artificial Sequence
<220> FEATURE:
<223> OTHER INFORMATION: rghR2 ET gRNA cassette

<400> SEQUENCE: 45
ggcggcgttt tcctgatacc gggagacggc attcgtaatc gtatgaggaa ctgatggcat 60
ctgcaggcta tatcagcgcg tctacagtcc aggaagcaag aagcagctat gattccattt 120
acgacatcgt gtcacagtac gatttagagg acctttctct gtttgacagc gaaaagtgga 180
aggtgctttc aaaaaaagac atcgaaaacc tggacaaata tttcgacttt ctcgtgcagg 240
aagcaagcag ccgaaacaaa aactgaatac ttctccgcgg cacactctcc tctctatcat 300
tttcgtctgt ttacgatcct gctgttattt tatcccttat gttaactttt gtcaatattt 360
ttcctgtcta agtatttcct atagtcaaca tttgtattaa aatgttcata tcatgaattt 420

```
gcggggggga tggcgatgac aaggttcggc gagcggctca aagagctgag ggaacaaaga    480

agcctgtcgg ttaatcagct tgccatgtat gccggtgtga gcgccgcagc catttccaga    540

atcgaaaacg gccaccgcgg cgttcccaag cccgcgacga tcagaaaatt ggccgaggct    600

ctgaaaatgc cgtacgagca gctcatggat attgccggtt atatgagagc tgacgagatt    660

cgcgaacagc cgcgcggcta tgtcacgatg caggagatcg cggccaagca cggcgtcgaa    720

gacctgtggc tgtttaaacc cgagaaatgg gactgtttgt cccgcgaaga cctgctcaac    780

ctcgaacagt attttcattt tttggttaat gaagcgaaga agcgccaatc ataaaaagcc    840

gaatttccct tttaggagaa gttcggcttt tttcggctgc cttaagcggc atccggattc    900

ggcgtcttgc ctttatgatg cttaacgggg ctcagcgcac gctcgagcca tcccatgaac    960

agatcggcga tgatcgccat cagcgccgtc gggatcgcgc ctgctagaat gatcgctgtt   1020

ccgttggtcg cgtttgatcc tcgctgataa acagctgaca tcaactaaaa gcttcattaa   1080

atactttgaa aaaagttgtt gacttaaaag aagctaaatg ttatagtaat aaaaaatggc   1140

tgcggctctg gaaagtttta gagctagaaa tagcaagtta aaataaggct agtccgttat   1200

caacttgaaa aagtggcacc gagtcggtgc gactcctgtt gatagatcca gtaatgacct   1260

cagaactcca tctggatttg ttcagaacgc tcggttgccg ccgggcgttt tttattggtg   1320

agaatgaatt cgcggccgca cgcgtccatg ggatccccg cgggt                    1365


<210> SEQ ID NO 46
<211> LENGTH: 1000
<212> TYPE: DNA
<213> ORGANISM: Artificial Sequence
<220> FEATURE:
<223> OTHER INFORMATION: rghR2 editing template

<400> SEQUENCE: 46

gtatgaggaa ctgatggcat ctgcaggcta tatcagcgcg tctacagtcc aggaagcaag     60

aagcagctat gattccattt acgacatcgt gtcacagtac gatttagagg acctttctct    120

gtttgacagc gaaaagtgga aggtgctttc aaaaaaagac atcgaaaacc tggacaaata    180

tttcgacttt ctcgtgcagg aagcaagcag ccgaaacaaa aactgaatac ttctccgcgg    240

cacactctcc tctctatcat tttcgtctgt ttacgatcct gctgttattt tatcccttat    300

gttaactttt gtcaatattt ttcctgtcta agtatttcct atagtcaaca tttgtattaa    360

aatgttcata tcatgaattt gcggggggga tggcgatgac aaggttcggc gagcggctca    420

aagagctgag ggaacaaaga agcctgtcgg ttaatcagct tgccatgtat gccggtgtga    480

gcgccgcagc catttccaga atcgaaaacg gccaccgcgg cgttcccaag cccgcgacga    540

tcagaaaatt ggccgaggct ctgaaaatgc cgtacgagca gctcatggat attgccggtt    600

atatgagagc tgacgagatt cgcgaacagc cgcgcggcta tgtcacgatg caggagatcg    660

cggccaagca cggcgtcgaa gacctgtggc tgtttaaacc cgagaaatgg gactgtttgt    720

cccgcgaaga cctgctcaac ctcgaacagt attttcattt tttggttaat gaagcgaaga    780

agcgccaatc ataaaaagcc gaatttccct tttaggagaa gttcggcttt tttcggctgc    840

cttaagcggc atccggattc ggcgtcttgc ctttatgatg cttaacgggg ctcagcgcac    900

gctcgagcca tcccatgaac agatcggcga tgatcgccat cagcgccgtc gggatcgcgc    960

ctgctagaat gatcgctgtt ccgttggtcg cgtttgatcc                         1000


<210> SEQ ID NO 47
<211> LENGTH: 285
```

<212> TYPE: DNA
<213> ORGANISM: Artificial Sequence
<220> FEATURE:
<223> OTHER INFORMATION: rghR2 gRNA expression cassette

<400> SEQUENCE: 47

```
tcgctgataa acagctgaca tcaactaaaa gcttcattaa atactttgaa aaaagttgtt     60

gacttaaaag aagctaaatg ttatagtaat aaaaaatggc tgcggctctg gaaagtttta    120

gagctagaaa tagcaagtta aaataaggct agtccgttat caacttgaaa aagtggcacc    180

gagtcggtgc gactcctgtt gatagatcca gtaatgacct cagaactcca tctggatttg    240

ttcagaacgc tcggttgccg ccgggcgttt tttattggtg agaat                    285
```

<210> SEQ ID NO 48
<211> LENGTH: 25
<212> TYPE: DNA
<213> ORGANISM: Artificial Sequence
<220> FEATURE:
<223> OTHER INFORMATION: rghR2 cassette forward primer

<400> SEQUENCE: 48

```
ggcggcgttt tcctgatacc gggag                                           25
```

<210> SEQ ID NO 49
<211> LENGTH: 20
<212> TYPE: DNA
<213> ORGANISM: Artificial Sequence
<220> FEATURE:
<223> OTHER INFORMATION: rghR2 cassette reverse primer

<400> SEQUENCE: 49

```
acccgcgggg atccccatgg                                                 20
```

<210> SEQ ID NO 50
<211> LENGTH: 6393
<212> TYPE: DNA
<213> ORGANISM: Artificial Sequence
<220> FEATURE:
<223> OTHER INFORMATION: plasmid pBL.comK

<400> SEQUENCE: 50

```
aagcttcata tgcaagggtt tattgttttc taaaatctga ttaccaatta gaatgaatat     60

ttcccaaata ttaaataata aaacaaaaaa attgaaaaaa gtgtttccac catttttttca   120

atttttttat aattttttta atctgttatt taaatagttt atagttaaat ttacattttc    180

attagtccat tcaatattct ctccaagata actacgaact gctaacaaaa ttctctccct    240

atgttctaat ggagaagatt cagccactgc atttcccgca atatcttttg gtatgatttt    300

acccgtgtcc atagttaaaa tcatacggca taaagttaat atagagttgg tttcatcatc    360

ctgataatta tctattaatt cctctgacga atccataatg gctcttctca catcagaaaa    420

tggaatatca ggtagtaatt cctctaagtc ataatttccg tatattcttt tatttttttcg   480

ttttgcttgg taaagcatta tggttaaatc tgaatttaat tccttctgag gaatgtatcc    540

ttgttcataa agctcttgta accattctcc ataaataaat tcttgtttgg gaggatgatt    600

ccacggtacc atttcttgct gaataataat tgttaattca atatatcgta agttgctttt    660

atctcctatt tttttgaaa taggtctaat tttttgtata agtatttctt tactttgatc     720

tgtcaatggt tcagatacga cgactaaaaa gtcaagatca ctatttggtt ttagtccact    780

ctcaactcct gatccaaaca tgtaagtacc aataaggtta ttttttaaat gtttccgaag    840
```

```
tattttttc actttattaa tttgttcgta tgtattcaaa tatatcctcc tcactatttt    900
gattagtacc tattttatat ccatagttgt taattaaata aacttaattt agtttattta    960
tggatttcat tggcttctaa attttttatc tagataataa ttattttagt taattttatt   1020
ctagattata tatgatatga tctttcattt ccataaaact aaagtaagtg taaacctatt   1080
cattgtttta aaaatatctc ttgccagtca cgttacgtta ttagttatag ttattataac   1140
atgtattcac gaacgggcgc gccggtatcc gcgcttcttg agcactattt attcaaagcc   1200
gctccagatc aatagcgctt tttcagctcc ctgaggatga attcgtatat cagctgattc   1260
cggtcttctt tcggatagag cataaattcc tgtttcttct gcatggggtt tccttcaatc   1320
ctgtcgataa attttgttct cagccatgcc gttcggtaaa cctggttttc gaaagatgag   1380
atggatacgg gcagctccag cgtttccccg ttgacaaacg tgacaaacgt gttgtcatac   1440
tttgccgcgc aaaactcgtg aacatgcgca tgggaaagcc acccgcactg aggacgagtt   1500
gaggaaaatg tggggaaaag aaaaatgttg tttgagtgat ccaccatgat cggcggttta   1560
tgggaaactt taatgacttc atatgtgccc gcttttcttc ccgcatagct cgatccgaaa   1620
tagcggcagc ttctttcgat aatttgaaac ggcttcatat tgacgcggaa agtcctgtcg   1680
gtctcaagta tttttgaggc ggatttctcc ccctcaccca gaggcaggac agccattgtc   1740
gaactgttta cttcatacgt atcctttgtc atatcctctg tgctcatgtg atttccccct   1800
taaaaataaa ttcattcaaa tacagatgca ttttatttca tatagtaagt acatcaccta   1860
ttagtttgtt gtttaaacaa actaacttat tttcatctta tataacctcg tcagtatttt   1920
caatattttt tttagttttt tatgaacaca ttagatttaa taaagggaag attcgctatg   1980
tactatgttg atacttaatt taaagattaa acaaatggag tggatgaagt ggatatcgct   2040
gatcaaacct ttgtcaaaaa agtaaatcaa aagttattat taaaagaaat ccttaaaaat   2100
tcacctattt caagagcaaa attatctgaa atgactggat taaataaatc aactgtctca   2160
tcacaggtaa acacgttaat gaaagaaagt atggtatttg aaataggtca aggacaatca   2220
agtggcggaa gaagacctgt catgcttgtt tttaataaaa aggcaggata ctccgttgga   2280
atagatgttg gtgtggatta tattaatggc attttaacag accttgaagg aacaatcgtt   2340
cttgatcaat accgccattt ggaatccaat tctccagaaa taacgaaaga cattttgatt   2400
gatatgattc atcactttat tacgcaaatg ccccaatctc cgtacgggtt tattggtata   2460
ggtacttgcg tgcctggact cattgataaa gatcaaaaaa ttgttttcac tccgaactcc   2520
aactggagag atattgactt aaaatcttcg atacaagaga agtacaatgt gtctgttttt   2580
attgaaaatg aggcaaatgc tggcgcatat ggagaaaaac tatttggagc tgcaaaaaat   2640
cacgataaca ttatttacgt aagtatcagc acaggaatag ggatcggtgt tattatcaac   2700
aatcatttat atagaggagt aagcggcttc tctggagaaa tgggacatat gacaatagac   2760
tttaatggtc ctaaatgcag ttgcggaaac cgaggatgct gggaattgta tgcttcagag   2820
aaggctttat ttaaatctct tcagaccaaa gagaaaaaac tgtcctatca agatatcata   2880
aacctcgccc atctgaatga tatcggaacc ttaaatgcat tacaaaattt tggattctat   2940
ttaggaatag gccttaccaa tattctaaat actctcaacc cacaagccgt aattttaaga   3000
aatagcataa ttgaatcgca tcctatggtt ttaaattcaa tgagaagtga agtatcatca   3060
agggtttatt cccaattagg caatagctat gaattattgc catcttcctt aggacagaat   3120
gcaccggcat taggaatgtc ctccattgtg attgatcatt ttctggacat gattacaatg   3180
taatttttta tggaatggac agctcatctt taaagatgag tttttttatt ctaggagtat   3240
```

```
ttctgaagca atagtgacat ggcaccttct catatgaaaa aggagttcta aaataaaaat   3300
ctccttttc atgtgcaaat tatttttctt tataacgaaa atatctaaat gacaatgcat   3360
atgcaagagg ggatcacata aatatatatt ttaaaaatat cccactttat ccaattttcg   3420
tttgttgaac taatgggtgc tttagttgaa gaataaaaga ccacattaaa aaatgtggtc   3480
ttttgtgttt ttttaaagga tttgagcgta gcgaaaaatc cttttcttc ttatcttgat   3540
actatataga aacaacatca tttttcaaaa ttaggtcaaa gccttgtgta tcaagggttt   3600
gatggttctt tgacaggtaa aaactccttc tgctattatt aaatactata tagaaacaac   3660
atcatttttc aaaattaggt caaagccttg tgtatcaagg gtttgatggt tctttgacag   3720
gtaaaaactc cttctgctat tattaaggtg tcgaatcaaa ataatagaat gctagagaac   3780
tagctcagaa ggagtttttt tgttgattta ttcatctgaa aatgattata gcatcctcga   3840
agataaaacc gcaacaggta aaaagcggga ttggaagggg aaaaagagac ggacgaacct   3900
catggcggag cattacgaag cgttagagag taagattggg gcaccttact atggcaaaaa   3960
ggctgaaaaa ctaattagtt gtgcagagta tctttcgttt aagagagacc cggagacggg   4020
caagttaaaa ctgtatcaag cccatttttg taaagtgagg ttatgtccga tgtgtgcgtg   4080
gcgcaggtcg ttaaaaattg cttatcacaa taagttgatc gtagaggaag ccaatagaca   4140
gtacggctgc ggatggattt ttctcacgct gacgattcga aatgtaaagg gagaacggct   4200
gaagccacaa atttctgcga tgatggaagg ctttaggaaa ctgttccagt acaaaaaagt   4260
aaaaacttcg gttcttggat ttttcagagc tttagagatt accaaaaatc atgaagaaga   4320
tacatatcat cctcattttc atgtgttgat accagtaagg aaaaattatt ttgggaaaaa   4380
ctatattaag caggcggagt ggacgagcct ttggaaaaag gcgatgaaat tggattacac   4440
tccaattgtc gatattcgtc gagtgaaagg taaagctaag attgacgctg aacagattga   4500
aaacgatgtg cggaacgcaa tgatggagca aaaagctgtt ctcgaaatct ctaaatatcc   4560
ggttaaggat acggatgttg tgcgcggtaa taaggtgact gaagacaatc tgaacacggt   4620
gctttacttg gatgatgcgt tggcagctcg aaggttaatt ggatacggtg gcattttgaa   4680
ggagatacat aaagagctga atcttggtga tgcggaggac ggcgatctgg tcaagattga   4740
ggaagaagat gacgaggttg caaatggtgc atttgaggtt atggcttatt ggcatcctgg   4800
cattaaaaat tacataatca aataaaaaaa gcagaccttt agaaggcctg ctttttaac   4860
taacccattt gtattgtgtt gaaatatgtt ttgtatggtg cactctcagt acaatctgct   4920
ctgatgccgc atagttaagc cagccccgac acccgccaac acccgctgac gcgccctgac   4980
gggcttgtct gctcccggca tccgcttaca gacaagctgt gaccgtctcc gggagctgca   5040
tgtgtcagag gttttcaccg tcatcaccga aacgcgcgag acgaaagggc ctcgtgatac   5100
gcctattttt ataggttaat gtcatgataa taatggtttc ttagcgattc acaaaaaata   5160
ggcacacgaa aaacaagtta agggatgcag tttatgcatc ccttaactta aaatactaaa   5220
aatgcccata ttttttcctc cttataaaat tagtataatt atagcacgag atctaaaagg   5280
atctaggtga agatcctttt tgataatctc atgaccaaaa tcccttaacg tgagttttcg   5340
ttccactgag cgtcagaccc cgtagaaaag atcaaaggat cttcttgaga tcctttttt   5400
ctgcgcgtaa tctgctgctt gcaaacaaaa aaaccaccgc taccagcggt ggtttgtttg   5460
ccggatcaag agctaccaac tctttttccg aaggtaactg gcttcagcag agcgcagata   5520
ccaaatactg ttcttctagt gtagccgtag ttaggccacc acttcaagaa ctctgtagca   5580
```

```
ccgcctacat acctcgctct gctaatcctg ttaccagtgg ctgctgccag tggcgataag   5640

tcgtgtctta ccgggttgga ctcaagacga tagttaccgg ataaggcgca gcggtcgggc   5700

tgaacggggg gttcgtgcac acagcccagc ttggagcgaa cgacctacac cgaactgaga   5760

tacctacagc gtgagctatg agaaagcgcc acgcttcccg aagggagaaa ggcggacagg   5820

tatccggtaa gcggcagggt cggaacagga gagcgcacga gggagcttcc agggggaaac   5880

gcctggtatc tttatagtcc tgtcgggttt cgccacctct gacttgagcg tcgatttttg   5940

tgatgctcgt caggggggcg gagcctatgg aaaaacgcca gcaacgcggc ctttttacgg   6000

ttcctggcct tttgctggcc ttttgctcac atgttctttc ctgcgttatc ccctgattct   6060

gtggataacc gtattaccgc ctttgagtga gctgataccg ctcgccgcag ccgaacgacc   6120

gagcgcagcg agtcagtgag cgaggaagcg gaagagcgcc caatacgcaa accgcctctc   6180

cccgcgcgtt ggccgattca ttaatgcagc tggcacgaca ggtttcccga ctggaaagcg   6240

ggcagtgagc gcaacgcaat taatgtgagt tagctcactc attaggcacc ccaggcttta   6300

cactttatgc ttccggctcg tatgttgtgt ggaattgtga gcggataaca atttcacaca   6360

ggaaacagct atgaccatga ttacgccgga tcc                                6393
```

<210> SEQ ID NO 51
<211> LENGTH: 1069
<212> TYPE: DNA
<213> ORGANISM: Bacillus licheniformis

<400> SEQUENCE: 51

```
cggcatcaag tggatattcc cggaagcctc gctattttaa gctgtgacaa ccagccgatc     60

agcgaagtgc tcggcatttc aacaattgaa atcaatataa aggaaatggg gaagcgcgcg    120

tttcgccttc tgcaaaaaag aatcggcggc gccgggccgg aaaaactgac tgttccttac    180

aagctgatca aaagggcgac tgtgtaatca aaacatcaat ctttttccag acagtgatca    240

aaattcgaca tttttcatca aaaacgtcaa aataaattga cgcgctttca tgagttttgt    300

acgatatgag agattgatga caaaaaggag ctgaggatcg tgaacagatc ctttaccgtt    360

gaaaaggtac tcaacaacaa cgttttaatc gctctccatg atgattacag agaagttgtc    420

ttgattggca aaggaatcgg ttttggtaaa aagcgcggag atcttatcga acatgagaac    480

tacgaaaaaa tgtttatcct ggaaaatgat aaggaacaat cgcagtataa gaagctcctc    540

acttatgtcg atgaaaaaat ggttgatatc gccaatgatg tcatctacca tatcgcgcaa    600

aaaatcggcc agccgctgaa cgaacacatt catgtcgccc tgacggacca tatcgcattt    660

gcagttaagc gtctagaaaa gggatttgat atgaaaaatc cgtttttgct tgagacggaa    720

tcgctttatc cgaaggaata cgaagtcgcc aaggaagccg tcgatatgat taatgaaaaa    780

tccgacattc agctgcctga aggtgaaatc gggttcatcg cgcttcatat ccacagtgcg    840

atgacaaacc gcccgctttc tgaagtcaat cagcattcac aactgatctc caggcttgtc    900

caggtcatcg aagattcatt ccagatgcaa gtcaacaggg aaagcgtgaa ctatttgcgg    960

ctgatcaggc acttgcgctt tacgattgac aggataaaac gggacgagcc gattcaggaa   1020

ccggaaaaat taatgttgtt gttgaaaacg gaatatccgc tgtgttaca              1069
```

<210> SEQ ID NO 52
<211> LENGTH: 20
<212> TYPE: DNA
<213> ORGANISM: Artificial Sequence
<220> FEATURE:
<223> OTHER INFORMATION: glcT locus forward primer

<400> SEQUENCE: 52
cggcatcaag tggatattcc 20

<210> SEQ ID NO 53
<211> LENGTH: 20
<212> TYPE: DNA
<213> ORGANISM: Artificial Sequence
<220> FEATURE:
<223> OTHER INFORMATION: glcT locus reverse primer

<400> SEQUENCE: 53
tgtaacacag cggatattcc 20

<210> SEQ ID NO 54
<211> LENGTH: 20
<212> TYPE: DNA
<213> ORGANISM: Artificial Sequence
<220> FEATURE:
<223> OTHER INFORMATION: glcT locus forward sequencing primer

<400> SEQUENCE: 54
tgaggatcgt gaacagatcc 20

<210> SEQ ID NO 55
<211> LENGTH: 281
<212> TYPE: PRT
<213> ORGANISM: Artificial Sequence
<220> FEATURE:
<223> OTHER INFORMATION: glcT L67F

<400> SEQUENCE: 55

```
Val Asn Arg Ser Phe Thr Val Glu Lys Val Leu Asn Asn Asn Val Leu
1               5                   10                  15

Ile Ala Leu His Asp Asp Tyr Arg Glu Val Val Leu Ile Gly Lys Gly
            20                  25                  30

Ile Gly Phe Gly Lys Lys Arg Gly Asp Leu Ile Glu His Glu Asn Tyr
        35                  40                  45

Glu Lys Met Phe Ile Leu Glu Asn Asp Lys Glu Gln Ser Gln Tyr Lys
    50                  55                  60

Lys Leu Phe Thr Tyr Val Asp Glu Lys Met Val Asp Ile Ala Asn Asp
65                  70                  75                  80

Val Ile Tyr His Ile Ala Gln Lys Ile Gly Gln Pro Leu Asn Glu His
                85                  90                  95

Ile His Val Ala Leu Thr Asp His Ile Ala Phe Ala Val Lys Arg Leu
            100                 105                 110

Glu Lys Gly Phe Asp Met Lys Asn Pro Phe Leu Leu Glu Thr Glu Ser
        115                 120                 125

Leu Tyr Pro Lys Glu Tyr Glu Val Ala Lys Glu Ala Val Asp Met Ile
    130                 135                 140

Asn Glu Lys Ser Asp Ile Gln Leu Pro Glu Gly Glu Ile Gly Phe Ile
145                 150                 155                 160

Ala Leu His Ile His Ser Ala Met Thr Asn Arg Pro Leu Ser Glu Val
                165                 170                 175

Asn Gln His Ser Gln Leu Ile Ser Arg Leu Val Gln Val Ile Glu Asp
            180                 185                 190

Ser Phe Gln Met Gln Val Asn Arg Glu Ser Val Asn Tyr Leu Arg Leu
        195                 200                 205

Ile Arg His Leu Arg Phe Thr Ile Asp Arg Ile Lys Arg Asp Glu Pro
```

```
    210                 215                 220

Ile Gln Glu Pro Glu Lys Leu Met Leu Leu Leu Lys Thr Glu Tyr Pro
225                 230                 235                 240

Leu Cys Tyr Asn Thr Ala Trp Lys Met Ile Lys Ile Leu Gln Gln Ala
                245                 250                 255

Leu Lys Lys Pro Val His Glu Ala Glu Ala Val Tyr Leu Thr Leu His
            260                 265                 270

Leu Tyr Arg Leu Thr Asn Lys Ile Ser
        275                 280


<210> SEQ ID NO 56
<211> LENGTH: 846
<212> TYPE: DNA
<213> ORGANISM: Artificial Sequence
<220> FEATURE:
<223> OTHER INFORMATION: glcT ORF encoding L67F

<400> SEQUENCE: 56

gtgaacagat cctttaccgt tgaaaaggta ctcaacaaca acgttttaat cgctctccat     60

gatgattaca gagaagttgt cttgattggc aaaggaatcg gttttggtaa aaagcgcgga    120

gatcttatcg aacatgagaa ctacgaaaaa atgtttatcc tggaaaatga taaggaacaa    180

tcgcagtata agaagctctt cacttatgtc gatgaaaaaa tggttgatat cgccaatgat    240

gtcatctacc atatcgcgca aaaaatcggc cagccgctga acgaacacat tcatgtcgcc    300

ctgacggacc atatcgcatt tgcagttaag cgtctagaaa agggatttga tatgaaaaat    360

ccgtttttgc ttgagacgga atcgctttat ccgaaggaat acgaagtcgc caaggaagcc    420

gtcgatatga ttaatgaaaa atccgacatt cagctgcctg aaggtgaaat cgggttcatc    480

gcgcttcata tccacagtgc gatgacaaac cgcccgcttt ctgaagtcaa tcagcattca    540

caactgatct ccaggcttgt ccaggtcatc gaagattcat tccagatgca agtcaacagg    600

gaaagcgtga actatttgcg gctgatcagg cacttgcgct ttacgattga caggataaaa    660

cgggacgagc cgattcagga accggaaaaa ttaatgttgt tgttgaaaac ggaatatccg    720

ctgtgttaca atactgcttg gaagatgatc aagatcttgc agcaagcgct caagaaaccg    780

gttcatgagg cagaagccgt ttatttgaca ttgcatttgt accgtttgac taataaaatt    840

tcataa                                                               846


<210> SEQ ID NO 57
<211> LENGTH: 1164
<212> TYPE: DNA
<213> ORGANISM: Bacillus licheniformis

<400> SEQUENCE: 57

gcgaatcgaa aacggaaagc gcggcgtgcc gaagccggcg acgatcagaa aactggcgga     60

cgctttgaaa gtcccgtatg aggaactgat ggcatctgca ggctatatca gcgcgtctac    120

agtccaggaa gcaagaagca gctatgattc catttacgac atcgtgtcac agtacgattt    180

agaggacctt tctctgtttg acagcgaaaa gtggaaggtg ctttcaaaaa aagacatcga    240

aaacctggac aaatatttcg actttctcgt gcaggaagca agcagccgaa acaaaaactg    300

aatacttctc cgcggcacac tctcctctct atcattttcg tctgtttacg atcctgctgt    360

tattttatcc cttatgttaa cttttgtcaa tatttttcct gtctaagtat ttcctatagt    420

caacatttgt attaaaatgt tcatatcatg aatttgcggg ggggatggcg atgacaaggt    480

tcggcgagcg gctcaaagag ctgagggaac aaagaagcct gtcggttaat cagcttgcca    540
```

tgtatgccgg tgtgagcgcc gcagccattt ccagagccgc agccatttcc agaatcgaaa 600
acggccaccg cggcgttccc aagcccgcga cgatcagaaa attggccgag gctctgaaaa 660
tgccgtacga gcagctcatg gatattgccg gttatatgag agctgacgag attcgcgaac 720
agccgcgcgg ctatgtcacg atgcaggaga tcgcggccaa gcacggcgtc gaagacctgt 780
ggctgtttaa acccgagaaa tgggactgtt tgtcccgcga agacctgctc aacctcgaac 840
agtattttca tttttggtt aatgaagcga agaagcgcca atcataaaaa gccgaatttc 900
ccttttagga gaagttcggc ttttttcggc tgccttaagc ggcatccgga ttcggcgtct 960
tgcctttatg atgcttaacg gggctcagcg cacgctcgag ccatcccatg aacagatcgg 1020
cgatgatcgc catcagcgcc gtcgggatcg cgcctgctag aatgatcgct gttccgttgg 1080
tcgcgtttga tcccctgaca atgatatccc cgaggccgcc tgcgccgaca aacgtgccga 1140
tggccgtaat gccgatcgcg atga 1164

<210> SEQ ID NO 58
<211> LENGTH: 20
<212> TYPE: DNA
<213> ORGANISM: Artificial Sequence
<220> FEATURE:
<223> OTHER INFORMATION: rghR2 locus forward primer

<400> SEQUENCE: 58
gcgaatcgaa aacggaaagc 20

<210> SEQ ID NO 59
<211> LENGTH: 20
<212> TYPE: DNA
<213> ORGANISM: Artificial Sequence
<220> FEATURE:
<223> OTHER INFORMATION: rghR2 locus reverse primer

<400> SEQUENCE: 59
tcatcgcgat cggcattacg 20

<210> SEQ ID NO 60
<211> LENGTH: 20
<212> TYPE: DNA
<213> ORGANISM: Artificial Sequence
<220> FEATURE:
<223> OTHER INFORMATION: rghR2 locus sequencing primer

<400> SEQUENCE: 60
tttcgacttt ctcgtgcagg 20

<210> SEQ ID NO 61
<211> LENGTH: 1146
<212> TYPE: DNA
<213> ORGANISM: Bacillus licheniformis

<400> SEQUENCE: 61
gcgaatcgaa aacggaaagc gcggcgtgcc gaagccggcg acgatcagaa aactggcgga 60
cgctttgaaa gtcccgtatg aggaactgat ggcatctgca ggctatatca gcgcgtctac 120
agtccaggaa gcaagaagca gctatgattc catttacgac atcgtgtcac agtacgattt 180
agaggacctt tctctgtttg acagcgaaaa gtggaaggtg ctttcaaaaa aagacatcga 240
aaacctggac aaatatttcg actttctcgt gcaggaagca agcagccgaa acaaaaactg 300
aatacttctc cgcggcacac tctcctctct atcattttcg tctgtttacg atcctgctgt 360

```
tattttatcc cttatgttaa cttttgtcaa tatttttcct gtctaagtat ttcctatagt    420

caacatttgt attaaaatgt tcatatcatg aatttgcggg ggggatggcg atgacaaggt    480

tcggcgagcg gctcaaagag ctgagggaac aaagaagcct gtcggttaat cagcttgcca    540

tgtatgccgg tgtgagcgcc gcagccattt ccagaatcga aaacggccac cgcggcgttc    600

ccaagcccgc gacgatcaga aaattggccg aggctctgaa aatgccgtac gagcagctca    660

tggatattgc cggttatatg agagctgacg agattcgcga acagccgcgc ggctatgtca    720

cgatgcagga gatcgcggcc aagcacggcg tcgaagacct gtggctgttt aaacccgaga    780

aatgggactg tttgtcccgc gaagacctgc tcaacctcga acagtatttt catttttttgg   840

ttaatgaagc gaagaagcgc caatcataaa aagccgaatt tcccttttag gagaagttcg    900

gctttttttcg gctgccttaa gcggcatccg gattcggcgt cttgccttta tgatgcttaa   960

cggggctcag cgcacgctcg agccatccca tgaacagatc ggcgatgatc gccatcagcg   1020

ccgtcgggat cgcgcctgct agaatgatcg ctgttccgtt ggtcgcgttt gatcccctga   1080

caatgatatc cccgaggccg cctgcgccga caaacgtgcc gatggccgta atgccgatcg   1140

cgatga                                                               1146
```

<210> SEQ ID NO 62
<211> LENGTH: 58
<212> TYPE: DNA
<213> ORGANISM: Bacillus subtilis

<400> SEQUENCE: 62

```
acagaatagt cttttaagta agtctactct gaattttttt aaaaggagag ggtaaaga      58
```

<210> SEQ ID NO 63
<211> LENGTH: 57
<212> TYPE: DNA
<213> ORGANISM: Artificial Sequence
<220> FEATURE:
<223> OTHER INFORMATION: aprE mod-5' UTR

<400> SEQUENCE: 63

```
acagaatagt cttttaagta agtctactct gaattttttt aaaaggagag ggtaaag       57
```

<210> SEQ ID NO 64
<211> LENGTH: 6208
<212> TYPE: DNA
<213> ORGANISM: Artificial Sequence
<220> FEATURE:
<223> OTHER INFORMATION: WT 5' UTR expression construct

<400> SEQUENCE: 64

```
ggctatgacg aaacgattgc agcctatgag gcgagtctcg aaaagctcgg acttgactac     60

cttgatttat acctgatcca ctggcctgtt gaaggacgct acaaagcggc gtggaaagcg    120

cttgaaacac tttatgaaca aggacgcgta aaagcaatcg gagtgagcaa ttttcagatt    180

caccatctgg aagacttgct gaaagatgcc gccgtcaaac cggcgatcaa ccaggttgag    240

tatcatccgc ggctgacgca gaaagagctg caagcgtttt gccgtgcgca cggcatccag    300

ctgcaagcat ggtcgccgct gatgcaaggc caattgctca gccatccact gctgaaagat    360

atcgcggaca agtacggcaa gacaccggcc caagtcattt tgcgctggga tttgcaaaac    420

ggggtcgtta cgattccgaa gtcgactaaa gcggagcgga ttgcccaaaa cgcggacata    480

tttgattttg aactgaccac cgaggaaatg aagcaaattg acgcgctgaa tgaaaacacc    540

cgtgtcggcc ctgatcccga taactttgac ttttaacaaa acggccccgt tcgacattcg    600
```

```
aacggggctt taattgaatt gtgcggttac accgccggac tccatcatca tcagttcttt    660
tttcatatcc aatccgcccc ggtatcccgt gagctgcccg cttttaccga taacccgatg    720
gcaaggcacc accattaaca gcggatttgc gccgatcgcc gcgcctactg cccgcacagc    780
ggcctgcttt tcaatatgct cggcgatatc ggaataggag caagtgctgc cgtaagggat    840
ttcggagagc gccttccaca ctgccagctg aaaaggcgtg ccggcaaggt cgacaggaaa    900
gctgaaatga gttcgcttgc cgttcaaata cgcctgcagc tgctcggcgt attctgccaa    960
tcctttgtca tcccgaatga aaactggctg tgtaaatctt ttttcagccc aagcggccaa   1020
atcctcgaag ccttgattcc atccccctgt aaaacagagc ccgcgggcag tcgccccaat   1080
gtgaatctgc caacctcggc aaataagcgt acgccagtat acgatttgat cgtccatatg   1140
tttacctccg tttcatttgc cggtacgacg tcggcgattg cccagtcttc tttttaaaca   1200
aagaggcaaa atattccgca ttcgcaatgc ctaccattga agcgatttct gcgatcgatc   1260
gttctgaatg agcaagcaaa tcgaccgctt tctcaatcct tttctgcagg atgtattctg   1320
ccggcgagac gcctttgatt cgtttaaatg tccgctgcag gtgaaaaggg ctgatatggc   1380
acctgtcagc caaagcttgc agagacagcg gatcgcgata agattcctcg atgatttcca   1440
ccacacgctg tgccagctct tcatccggca gcagcgcccc ggccggattg cagcgtttgc   1500
aggggcggta cccttctgat aaagcatctt ttgcattgaa aaagatctgc acattgtcga   1560
tttgcggaac tctcgatttg caggaagggc ggcaaaatat gccggtcgtt ttgaccgcgt   1620
aataaaaaac tccgtcatag gcggaatcgt tttccgtaat cgcccgccac atttcaggcg   1680
tcaatcgtga tttgctgttc atatcttcac cccgatctat gtcagtataa cctatatgac   1740
agccggaggt ggagaggcgg agaacggcac agcaagaaga caaagaagaa gagagactgt   1800
tgcctggacc tccgaaacgc gctacaattc atttacaaca caggatgggg tgagaatatt   1860
gccggaatca gtgaagcagg cctcctaaaa taaaaatcta tattttagga ggtaaaacat   1920
gaattttcaa acaatcgagc ttgacacatg gtatagaaaa tcttattttg accattacat   1980
gaaggaagcg aaatgttctt tcagcatcac ggcaaacgtc aatgtgacaa atttgctcgc   2040
cgtgctcaag aaaaagaagc tcaagctgta tccggctttt atttatatcg tatcaagggt   2100
cattcattcg cgccctgagt ttagaacaac gtttgatgac aaaggacagc tgggttattg   2160
ggaacaaatg catccgtgct atgcgatttt tcatcaggac gaccaaacgt tttccgccct   2220
ctggacggaa tactcagacg atttttcgca gttttatcat caatatcttc tggacgccga   2280
gcgctttgga gacaaaaggg gcctttgggc taagccggac atcccgccca atacgttttc   2340
agtttcttct attccatggg tgcgcttttc aaacttcaat ttaaaccttg ataacagcga   2400
acacttgctg ccgattatta caaacgggaa atacttttca gaaggcaggg aaacattttt   2460
gcccgtttcc ttgcaagttc accatgcagt gtgtgacggc tatcatgccg gcgcttttat   2520
aaacgagttg gaacggcttg ccgccgattg tgaggagtgg cttgtgtgac agaggaaagg   2580
ccgatatgat tcggcctttt ttatatgtac ttcttagcgg gtctcttaac ccccctcgag   2640
gtcgctgata aacagctgac atcaatatcc tattttttca aaaaatattt taaaaagttg   2700
ttgacttaaa agaagctaaa tgttatagta ataaaacaga atagtctttt aagtaagtct   2760
actctgaatt tttttaaaag gagagggtaa agaatgaaac aacaaaaacg gctttacgcc   2820
cgattgctga cgctgttatt tgcgctcatc ttcttgctgc ctcattctgc agctagcgca   2880
gccgcaccgt ttaacggtac catgatgcag tattttgaat ggtacttgcc ggatgatggc   2940
```

```
acgttatgga ccaaagtggc caatgaagcc aacaacttat ccagccttgg catcaccgct   3000
ctttggctgc cgcccgctta caaaggaaca agccgcagcg acgtagggta cggagtatac   3060
gacttgtatg acctcggcga attcaatcaa aaagggaccg tccgcacaaa atatggaaca   3120
aaagctcaat atcttcaagc cattcaagcc gcccacgccg ctggaatgca agtgtacgcc   3180
gatgtcgtgt tcgaccataa aggcggcgct gacggcacgg aatgggtgga cgccgtcgaa   3240
gtcaatccgt ccgaccgcaa ccaagaaatc tcgggcacct atcaaatcca agcatggacg   3300
aaatttgatt ttcccgggcg gggcaacacc tactccagct ttaagtggcg ctggtaccat   3360
tttgacggcg ttgattggga cgaaagccga aaattaagcc gcatttacaa attcaggggc   3420
atcggcaaag cgtgggattg gccggtagac acagaaaacg gaaactatga ctacttaatg   3480
tatgccgacc ttgatatgga tcatcccgaa gtcgtgaccg agctgaaaaa ctgggggaaa   3540
tggtatgtca acacaacgaa cattgatggg ttccggcttg atgccgtcaa gcatattaag   3600
ttcagttttt ttcctgattg gttgtcgtat gtgcgttctc agactggcaa gccgctattt   3660
accgtcgggg aatattggag ctatgacatc aacaagttgc acaattacat tacgaaaaca   3720
aacggaacga tgtctttgtt tgatgccccg ttacacaaca aattttatac cgcttccaaa   3780
tcagggggcg catttgatat gcgcacgtta atgaccaata ctctcatgaa agatcaaccg   3840
acattggccg tcaccttcgt tgataatcat gacaccgaac ccggccaagc gcttcagtca   3900
tgggtcgacc catggttcaa accgttggct tacgccttta ttctaactcg gcaggaagga   3960
tacccgtgcg tcttttatgg tgactattat ggcattccac aatataacat tccttcgctg   4020
aaaagcaaaa tcgatccgct cctcatcgcg cgcagggatt atgcttacgg aacgcaacat   4080
gattatcttg atcactccga catcatcggg tggacaaggg aaggggtcac tgaaaaacca   4140
ggatccgggc tggccgcact gatcaccgat gggccgggag gaagcaaatg gatgtacgtt   4200
ggcaaacaac acgctggaaa agtgttctat gaccttaccg gcaaccggag tgacaccgtc   4260
accatcaaca gtgatggatg gggggaattc aaagtcaatg gcggttcggt ttcggtttgg   4320
gttcctagaa aaacgaccta aaagcttctc gaggttaaca gaggacggat ttcctgaagg   4380
aaatccgttt ttttattttt aacatctctc actgctgtgt gattttactc acggcatttg   4440
gaacgccggc tctcaacaaa ctttctgtag tgaaaatcat gaaccaaacg gatcgtcggc   4500
ctgattaaca gctgaaagct gccgatcaca aacatccata gtcccgccgg cttcagttcc   4560
tcggagaaaa agcagaagct cccgacaagg aataaaaggc cgatgagaaa atcgtttaat   4620
gtatgtagaa ctttgtatct ttttttgaaa aagagttcat atcgattgtt attgttttgc   4680
ggcattgctt gatcactcca atccttttat ttaccctgcc ggaagccgga gtgaaacgcc   4740
ggtatacata ggatttatga attaggaaaa catatgggga aataaaccat ccaggagtga   4800
aaaatatgcg gttattcata tgtgcatcgt gcctgttcgg cttgattgtt ccgtcatttg   4860
aaacgaaagc gctgacgttt gaagaattgc cggttaaaca agcttcaaaa caatgggaag   4920
ttcaaatcgg taaagccgaa gccggaaacg gaatggcgaa accggaaaaa ggagcgtttc   4980
atacttatgc tgtcgaaatc aaaaacattg gacacgatgt ggcttcggcg gaaatttttg   5040
tctatcggaa cgagcctaat tcttcaacga aattttcgct ttggaacatt cctcacgaaa   5100
atccggtttc tttagccaaa agcttaaatc acggaagctc tgtcaagcac cgcaatctgc   5160
ttatggcaga gaatgcgacc gaattggaag tggacatgat ttggacggaa aaaggaagcg   5220
aaggcagact tttaaaggaa acgttcattt tcaagggaga tgaatcatga agaaaaaatg   5280
gccgttcatc gtcaacggtc tttttttaat gacttaggca gccgatcgtt cggccatacg   5340
```

```
atatcgaagc gacctcgaac cagcagagct cgtcacaaaa catttgcatt taaagaaaaa   5400

tacaggatgt tttcaccaat atttttctca atgatgatac actattgaca agctgctact   5460

ttgggagggt gtttccatag atgccgatga agcaaaaaca ccaaatgtgt catgagagct   5520

ctctctaatc gatataaaag tagggtgaac cggggttgtc aatctgtaaa agatcttttt   5580

ttatcccgtg atacgctttt ggaattctga atcttcaaga aagtccccag ccttttgctg   5640

atcaatcgag aacaaaggat gatacatatg aaaagaatag ataaaatcta ccatcagctg   5700

ctggataatt ttcgcgaaaa gaatatcaat cagcttttaa agatacaagg gaattcggct   5760

aaagaaatcg ccgggcagct gcaaatggag cgttccaatg tcagctttga attaaacaat   5820

ctggttcggg ccaaaaaggt gatcaagatt aaaacgttcc ccgtccgcta catcccggtg   5880

gaaattgttg aaaacgtctt gaacatcaaa tggaattcag agttgatgga ggttgaagaa   5940

ctgaggcggc tggctgacgg ccaaaaaaag ccggcgcgca atatatccgc cgatcccctc   6000

gagctcatga tcggggctaa agggagcttg aaaaaggcaa tttctcaggc gaaagcggca   6060

gtcttttatc ctccgcacgg cttgcatatg ctgctgctcg ggccgacggg ttcggggaaa   6120

tcgctgtttg cgaatcggat ctaccagttc gccgtttatt ctgacatatt gaagcccgat   6180

tccccgttca tcacattcaa ctgtgcag                                      6208
```

```
<210> SEQ ID NO 65
<211> LENGTH: 6207
<212> TYPE: DNA
<213> ORGANISM: Artificial Sequence
<220> FEATURE:
<223> OTHER INFORMATION: Mod 5' UTR expression construct

<400> SEQUENCE: 65

ggctatgacg aaacgattgc agcctatgag gcgagtctcg aaaagctcgg acttgactac     60

cttgatttat acctgatcca ctggcctgtt gaaggacgct acaaagcggc gtggaaagcg    120

cttgaaacac tttatgaaca aggacgcgta aaagcaatcg gagtgagcaa ttttcagatt    180

caccatctgg aagacttgct gaaagatgcc gccgtcaaac cggcgatcaa ccaggttgag    240

tatcatccgc ggctgacgca gaaagagctg caagcgtttt gccgtgcgca cggcatccag    300

ctgcaagcat ggtcgccgct gatgcaaggc caattgctca gccatccact gctgaaagat    360

atcgcggaca agtacggcaa gacaccggcc caagtcattt tgcgctggga tttgcaaaac    420

ggggtcgtta cgattccgaa gtcgactaaa gcggagcgga ttgcccaaaa cgcggacata    480

tttgattttg aactgaccac cgaggaaatg aagcaaattg acgcgctgaa tgaaaacacc    540

cgtgtcggcc ctgatcccga taactttgac ttttaacaaa acggccccgt tcgacattcg    600

aacggggctt taattgaatt gtgcggttac accgccggac tccatcatca tcagttcttt    660

tttcatatcc aatccgcccc ggtatcccgt gagctgcccg cttttaccga taacccgatg    720

gcaaggcacc accattaaca gcggatttgc gccgatcgcc gcgcctactg cccgcacagc    780

ggcctgcttt tcaatatgct cggcgatatc ggaataggag caagtgctgc cgtaagggat    840

ttcggagagc gccttccaca ctgccagctg aaaaggcgtg ccggcaaggt cgacaggaaa    900

gctgaaatga gttcgcttgc cgttcaaata cgcctgcagc tgctcggcgt attctgccaa    960

tcctttgtca tcccgaatga aaactggctg tgtaaatctt ttttcagccc aagcggccaa   1020

atcctcgaag ccttgattcc atccccctgt aaaacagagc ccgcgggcag tcgccccaat   1080

gtgaatctgc caacctcggc aaataagcgt acgccagtat acgatttgat cgtccatatg   1140
```

```
tttacctccg tttcatttgc cggtacgacg tcggcgattg cccagtcttc tttttaaaca   1200
aagaggcaaa atattccgca ttcgcaatgc ctaccattga agcgatttct gcgatcgatc   1260
gttctgaatg agcaagcaaa tcgaccgctt tctcaatcct tttctgcagg atgtattctg   1320
ccggcgagac gcctttgatt cgtttaaatg tccgctgcag gtgaaaaggg ctgatatggc   1380
acctgtcagc caaagcttgc agagacagcg gatcgcgata agattcctcg atgatttcca   1440
ccacacgctg tgccagctct tcatccggca gcagcgcccc ggccggattg cagcgtttgc   1500
aggggcggta cccttctgat aaagcatctt ttgcattgaa aaagatctgc acattgtcga   1560
tttgcggaac tctcgatttg caggaagggc ggcaaaatat gccggtcgtt ttgaccgcgt   1620
aataaaaaac tccgtcatag gcggaatcgt tttccgtaat cgcccgccac atttcaggcg   1680
tcaatcgtga tttgctgttc atatcttcac cccgatctat gtcagtataa cctatatgac   1740
agccggaggt ggagaggcgg agaacggcac agcaagaaga caaagaagaa gagagactgt   1800
tgcctggacc tccgaaacgc gctacaattc atttacaaca caggatgggg tgagaatatt   1860
gccggaatca gtgaagcagg cctcctaaaa taaaaatcta tattttagga ggtaaaacat   1920
gaattttcaa acaatcgagc ttgacacatg gtatagaaaa tcttattttg accattacat   1980
gaaggaagcg aaatgttctt tcagcatcac ggcaaacgtc aatgtgacaa atttgctcgc   2040
cgtgctcaag aaaaagaagc tcaagctgta tccggctttt atttatatcg tatcaagggt   2100
cattcattcg cgccctgagt ttagaacaac gtttgatgac aaaggacagc tgggttattg   2160
ggaacaaatg catccgtgct atgcgatttt tcatcaggac gaccaaacgt tttccgccct   2220
ctggacggaa tactcagacg atttttcgca gttttatcat caatatcttc tggacgccga   2280
gcgctttgga gacaaaaggg gcctttgggc taagccggac atcccgccca atacgttttc   2340
agtttcttct attccatggg tgcgcttttc aaacttcaat ttaaaccttg ataacagcga   2400
acacttgctg ccgattatta caaacgggaa atacttttca gaaggcaggg aaacattttt   2460
gcccgtttcc ttgcaagttc accatgcagt gtgtgacggc tatcatgccg gcgcttttat   2520
aaacgagttg gaacggcttg ccgccgattg tgaggagtgg cttgtgtgac agaggaaagg   2580
ccgatatgat tcggcctttt ttatatgtac ttcttagcgg gtctcttaac ccccctcgag   2640
gtcgctgata aacagctgac atcaatatcc tattttttca aaaaatattt taaaaagttg   2700
ttgacttaaa agaagctaaa tgttatagta ataaaacaga atagtctttt aagtaagtct   2760
actctgaatt tttttaaaag gagagggtaa agatgaaaca acaaaaacgg ctttacgccc   2820
gattgctgac gctgttattt gcgctcatct tcttgctgcc tcattctgca gctagcgcag   2880
ccgcaccgtt taacggtacc atgatgcagt attttgaatg gtacttgccg gatgatggca   2940
cgttatggac caaagtggcc aatgaagcca acaacttatc cagccttggc atcaccgctc   3000
tttggctgcc gcccgcttac aaaggaacaa gccgcagcga cgtagggtac ggagtatacg   3060
acttgtatga cctcggcgaa ttcaatcaaa aagggaccgt ccgcacaaaa tatggaacaa   3120
aagctcaata tcttcaagcc attcaagccg cccacgccgc tggaatgcaa gtgtacgccg   3180
atgtcgtgtt cgaccataaa ggcggcgctg acggcacgga atgggtggac gccgtcgaag   3240
tcaatccgtc cgaccgcaac caagaaatct cgggcaccta tcaaatccaa gcatggacga   3300
aatttgattt tcccgggcgg ggcaacacct actccagctt taagtggcgc tggtaccatt   3360
ttgacggcgt tgattgggac gaaagccgaa aattaagccg catttacaaa ttcaggggca   3420
tcggcaaagc gtgggattgg ccggtagaca cagaaaacgg aaactatgac tacttaatgt   3480
atgccgacct tgatatggat catcccgaag tcgtgaccga gctgaaaaac tgggggaaat   3540
```

```
ggtatgtcaa cacaacgaac attgatgggt tccggcttga tgccgtcaag catattaagt   3600
tcagtttttt tcctgattgg ttgtcgtatg tgcgttctca gactggcaag ccgctattta   3660
ccgtcgggga atattggagc tatgacatca acaagttgca caattacatt acgaaaacaa   3720
acggaacgat gtctttgttt gatgccccgt tacacaacaa attttatacc gcttccaaat   3780
cagggggcgc atttgatatg cgcacgttaa tgaccaatac tctcatgaaa gatcaaccga   3840
cattggccgt caccttcgtt gataatcatg acaccgaacc cggccaagcg cttcagtcat   3900
gggtcgaccc atggttcaaa ccgttggctt acgcctttat tctaactcgg caggaaggat   3960
acccgtgcgt cttttatggt gactattatg gcattccaca atataacatt ccttcgctga   4020
aaagcaaaat cgatccgctc ctcatcgcgc gcagggatta tgcttacgga acgcaacatg   4080
attatcttga tcactccgac atcatcgggt ggacaaggga aggggtcact gaaaaaccag   4140
gatccgggct ggccgcactg atcaccgatg ggccgggagg aagcaaatgg atgtacgttg   4200
gcaaacaaca cgctggaaaa gtgttctatg accttaccgg caaccggagt gacaccgtca   4260
ccatcaacag tgatggatgg ggggaattca aagtcaatgg cggttcggtt tcggtttggg   4320
ttcctagaaa aacgacctaa aagcttctcg aggttaacag aggacggatt tcctgaagga   4380
aatccgtttt tttatttta acatctctca ctgctgtgtg atttactca cggcatttgg   4440
aacgccggct ctcaacaaac tttctgtagt gaaaatcatg aaccaaacgg atcgtcggcc   4500
tgattaacag ctgaaagctg ccgatcacaa acatccatag tcccgccggc ttcagttcct   4560
cggagaaaaa gcagaagctc ccgacaagga ataaaaggcc gatgagaaaa tcgtttaatg   4620
tatgtagaac tttgtatctt tttttgaaaa agagttcata tcgattgtta ttgttttgcg   4680
gcattgcttg atcactccaa tccttttatt taccctgccg gaagccggag tgaaacgccg   4740
gtatacatag gatttatgaa ttaggaaaac atatggggaa ataaaccatc caggagtgaa   4800
aaatatgcgg ttattcatat gtgcatcgtg cctgttcggc ttgattgttc cgtcatttga   4860
aacgaaagcg ctgacgtttg aagaattgcc ggttaaacaa gcttcaaaac aatgggaagt   4920
tcaaatcggt aaagccgaag ccggaaacgg aatggcgaaa ccggaaaaag gagcgtttca   4980
tacttatgct gtcgaaatca aaaacattgg acacgatgtg gcttcggcgg aaatttttgt   5040
ctatcggaac gagcctaatt cttcaacgaa attttcgctt tggaacattc ctcacgaaaa   5100
tccggtttct ttagccaaaa gcttaaatca cggaagctct gtcaagcacc gcaatctgct   5160
tatggcagag aatgcgaccg aattggaagt ggacatgatt tggacggaaa aaggaagcga   5220
aggcagactt ttaaaggaaa cgttcatttt caagggagat gaatcatgaa gaaaaaatgg   5280
ccgttcatcg tcaacggtct ttttttaatg acttaggcag ccgatcgttc ggccatacga   5340
tatcgaagcg acctcgaacc agcagagctc gtcacaaaac atttgcattt aaagaaaaat   5400
acaggatgtt ttcaccaata tttttctcaa tgatgataca ctattgacaa gctgctactt   5460
tgggagggtg tttccataga tgccgatgaa gcaaaaacac caaatgtgtc atgagagctc   5520
tctctaatcg atataaaagt agggtgaacc ggggttgtca atctgtaaaa gatctttttt   5580
tatcccgtga tacgcttttg gaattctgaa tcttcaagaa agtccccagc cttttgctga   5640
tcaatcgaga acaaaggatg atacatatga aaagaataga taaaatctac catcagctgc   5700
tggataattt tcgcgaaaag aatatcaatc agcttttaaa gatacaaggg aattcggcta   5760
aagaaatcgc cgggcagctg caaatggagc gttccaatgt cagctttgaa ttaaacaatc   5820
tggttcgggc caaaaaggtg atcaagatta aaacgttccc cgtccgctac atcccggtgg   5880
```

```
aaattgttga aaacgtcttg aacatcaaat ggaattcaga gttgatggag gttgaagaac   5940

tgaggcggct ggctgacggc caaaaaaagc cggcgcgcaa tatatccgcc gatcccctcg   6000

agctcatgat cggggctaaa gggagcttga aaaaggcaat ttctcaggcg aaagcggcag   6060

tcttttatcc tccgcacggc ttgcatatgc tgctgctcgg gccgacgggt tcggggaaat   6120

cgctgtttgc gaatcggatc taccagttcg ccgtttattc tgacatattg aagcccgatt   6180

ccccgttcat cacattcaac tgtgcag                                       6207
```

<210> SEQ ID NO 66
<211> LENGTH: 1703
<212> TYPE: DNA
<213> ORGANISM: Bacillus licheniformis

<400> SEQUENCE: 66

```
ggctatgacg aaacgattgc agcctatgag gcgagtctcg aaaagctcgg acttgactac     60

cttgatttat acctgatcca ctggcctgtt gaaggacgct acaaagcggc gtggaaagcg    120

cttgaaacac tttatgaaca aggacgcgta aaagcaatcg gagtgagcaa ttttcagatt    180

caccatctgg aagacttgct gaaagatgcc gccgtcaaac cggcgatcaa ccaggttgag    240

tatcatccgc ggctgacgca gaaagagctg caagcgtttt gccgtgcgca cggcatccag    300

ctgcaagcat ggtcgccgct gatgcaaggc caattgctca gccatccact gctgaaagat    360

atcgcggaca agtacggcaa gacaccggcc caagtcattt tgcgctggga tttgcaaaac    420

ggggtcgtta cgattccgaa gtcgactaaa gcggagcgga ttgcccaaaa cgcggacata    480

tttgattttg aactgaccac cgaggaaatg aagcaaattg acgcgctgaa tgaaaacacc    540

cgtgtcggcc ctgatcccga taactttgac ttttaacaaa acggccccgt tcgacattcg    600

aacggggctt taattgaatt gtgcggttac accgccggac tccatcatca tcagttcttt    660

tttcatatcc aatccgcccc ggtatcccgt gagctgcccg cttttaccga taacccgatg    720

gcaaggcacc accattaaca gcggatttgc gccgatcgcc gcgcctactg cccgcacagc    780

ggcctgcttt tcaatatgct cggcgatatc ggaataggag caagtgctgc cgtaagggat    840

ttcggagagc gccttccaca ctgccagctg aaaaggcgtg ccggcaaggt cgacaggaaa    900

gctgaaatga gttcgcttgc cgttcaaata cgcctgcagc tgctcggcgt attctgccaa    960

tcctttgtca tcccgaatga aaactggctg tgtaaatctt ttttcagccc aagcggccaa   1020

atcctcgaag ccttgattcc atccccctgt aaaacagagc ccgcgggcag tcgccccaat   1080

gtgaatctgc caacctcggc aaataagcgt acgccagtat acgatttgat cgtccatatg   1140

tttacctccg tttcatttgc cggtacgacg tcggcgattg cccagtcttc tttttaaaca   1200

aagaggcaaa atattccgca ttcgcaatgc ctaccattga agcgatttct gcgatcgatc   1260

gttctgaatg agcaagcaaa tcgaccgctt tctcaatcct tttctgcagg atgtattctg   1320

ccggcgagac gcctttgatt cgtttaaatg tccgctgcag gtgaaaaggg ctgatatggc   1380

acctgtcagc caaagcttgc agagacagcg gatcgcgata agattcctcg atgatttcca   1440

ccacacgctg tgccagctct tcatccggca gcagcgcccc ggccggattg cagcgtttgc   1500

aggggcggta cccttctgat aaagcatctt ttgcattgaa aaagatctgc acattgtcga   1560

tttgcggaac tctcgatttg caggaagggc ggcaaaatat gccggtcgtt ttgaccgcgt   1620

aataaaaaac tccgtcatag gcggaatcgt tttccgtaat cgcccgccac atttcaggcg   1680

tcaatcgtga tttgctgttc ata                                           1703
```

<210> SEQ ID NO 67
<211> LENGTH: 937
<212> TYPE: DNA
<213> ORGANISM: Bacillus licheniformis

<400> SEQUENCE: 67

```
atcttcaccc cgatctatgt cagtataacc tatatgacag ccggaggtgg agaggcggag     60

aacggcacag caagaagaca aagaagaaga gagactgttg cctggacctc cgaaacgcgc    120

tacaattcat ttacaacaca ggatggggtg agaatattgc cggaatcagt gaagcaggcc    180

tcctaaaata aaaatctata ttttaggagg taaaacatga attttcaaac aatcgagctt    240

gacacatggt atagaaaatc ttattttgac cattacatga aggaagcgaa atgttctttc    300

agcatcacgg caaacgtcaa tgtgacaaat ttgctcgccg tgctcaagaa aaagaagctc    360

aagctgtatc cggcttttat ttatatcgta tcaagggtca ttcattcgcg ccctgagttt    420

agaacaacgt ttgatgacaa aggacagctg ggttattggg aacaaatgca tccgtgctat    480

gcgatttttc atcaggacga ccaaacgttt tccgccctct ggacggaata ctcagacgat    540

ttttcgcagt tttatcatca atatcttctg gacgccgagc gctttggaga caaaaggggc    600

ctttgggcta agccggacat cccgcccaat acgttttcag tttcttctat tccatgggtg    660

cgcttttcaa acttcaattt aaaccttgat aacagcgaac acttgctgcc gattattaca    720

aacgggaaat acttttcaga aggcagggaa acatttttgc ccgtttcctt gcaagttcac    780

catgcagtgt gtgacggcta tcatgccggc gcttttataa acgagttgga acggcttgcc    840

gccgattgtg aggagtggct tgtgtgacag aggaaaggcc gatatgattc ggcctttttt    900

atatgtactt cttagcgggt ctcttaaccc ccctcga                              937
```

<210> SEQ ID NO 68
<211> LENGTH: 95
<212> TYPE: DNA
<213> ORGANISM: Artificial Sequence
<220> FEATURE:
<223> OTHER INFORMATION: spoVGrrnIp hybrid promoter

<400> SEQUENCE: 68

```
gtcgctgata aacagctgac atcaatatcc tatttttca aaaaatattt taaaaagttg      60

ttgacttaaa agaagctaaa tgttatagta ataaa                               95
```

<210> SEQ ID NO 69
<211> LENGTH: 87
<212> TYPE: DNA
<213> ORGANISM: Bacillus licheniformis

<400> SEQUENCE: 69

```
atgaaacaac aaaaacggct ttacgcccga ttgctgacgc tgttatttgc gctcatcttc     60

ttgctgcctc attctgcagc tagcgca                                          87
```

<210> SEQ ID NO 70
<211> LENGTH: 1461
<212> TYPE: DNA
<213> ORGANISM: G. stearothermophilus

<400> SEQUENCE: 70

```
gccgcaccgt ttaacggtac catgatgcag tattttgaat ggtacttgcc ggatgatggc     60

acgttatgga ccaaagtggc caatgaagcc aacaacttat ccagccttgg catcaccgct    120

ctttggctgc cgcccgctta caaaggaaca agccgcagcg acgtagggta cggagtatac    180
```

```
gacttgtatg acctcggcga attcaatcaa aaagggaccg tccgcacaaa atatggaaca    240
aaagctcaat atcttcaagc cattcaagcc gcccacgccg ctggaatgca agtgtacgcc    300
gatgtcgtgt tcgaccataa aggcggcgct gacggcacgg aatgggtgga cgccgtcgaa    360
gtcaatccgt ccgaccgcaa ccaagaaatc tcgggcacct atcaaatcca agcatggacg    420
aaatttgatt ttcccgggcg gggcaacacc tactccagct ttaagtggcg ctggtaccat    480
tttgacggcg ttgattggga cgaaagccga aaattaagcc gcatttacaa attcaggggc    540
atcggcaaag cgtgggattg gccggtagac acagaaaacg gaaactatga ctacttaatg    600
tatgccgacc ttgatatgga tcatcccgaa gtcgtgaccg agctgaaaaa ctgggggaaa    660
tggtatgtca acacaacgaa cattgatggg ttccggcttg atgccgtcaa gcatattaag    720
ttcagttttt ttcctgattg gttgtcgtat gtgcgttctc agactggcaa gccgctattt    780
accgtcgggg aatattggag ctatgacatc aacaagttgc acaattacat tacgaaaaca    840
aacggaacga tgtctttgtt tgatgccccg ttacacaaca aattttatac cgcttccaaa    900
tcagggggcg catttgatat gcgcacgtta atgaccaata ctctcatgaa agatcaaccg    960
acattggccg tcaccttcgt tgataatcat gacaccgaac ccggccaagc gcttcagtca   1020
tgggtcgacc catggttcaa accgttggct tacgccttta ttctaactcg gcaggaagga   1080
tacccgtgcg tcttttatgg tgactattat ggcattccac aatataacat tccttcgctg   1140
aaaagcaaaa tcgatccgct cctcatcgcg cgcagggatt atgcttacgg aacgcaacat   1200
gattatcttg atcactccga catcatcggg tggacaaggg aagggggtcac tgaaaaacca   1260
ggatccgggc tggccgcact gatcaccgat gggccgggag gaagcaaatg gatgtacgtt   1320
ggcaaacaac acgctggaaa agtgttctat gaccttaccg gcaaccggag tgacaccgtc   1380
accatcaaca gtgatggatg gggggaattc aaagtcaatg gcggttcggt ttcggtttgg   1440
gttcctagaa aaacgaccta a                                                1461
```

```
<210> SEQ ID NO 71
<211> LENGTH: 34
<212> TYPE: DNA
<213> ORGANISM: Bacillus licheniformis

<400> SEQUENCE: 71

cggatttcct gaaggaaatc cgttttttta tttt                                    34


<210> SEQ ID NO 72
<211> LENGTH: 1809
<212> TYPE: DNA
<213> ORGANISM: Bacillus licheniformis

<400> SEQUENCE: 72

taacatctct cactgctgtg tgattttact cacggcattt ggaacgccgg ctctcaacaa      60
actttctgta gtgaaaatca tgaaccaaac ggatcgtcgg cctgattaac agctgaaagc     120
tgccgatcac aaacatccat agtcccgccg gcttcagttc ctcggagaaa aagcagaagc     180
tcccgacaag gaataaaagg ccgatgagaa aatcgtttaa tgtatgtaga actttgtatc     240
ttttttgaa aaagagttca tatcgattgt tattgttttg cggcattgct tgatcactcc      300
aatcctttta tttaccctgc cggaagccgg agtgaaacgc cggtatacat aggatttatg     360
aattaggaaa acatatgggg aaataaacca tccaggagtg aaaaatatgc ggttattcat     420
atgtgcatcg tgcctgttcg gcttgattgt tccgtcattt gaaacgaaag cgctgacgtt     480
tgaagaattg ccggttaaac aagcttcaaa acaatgggaa gttcaaatcg gtaaagccga     540
```

```
agccggaaac ggaatggcga aaccggaaaa aggagcgttt catacttatg ctgtcgaaat    600

caaaaacatt ggacacgatg tggcttcggc ggaaattttt gtctatcgga acgagcctaa    660

ttcttcaacg aaattttcgc tttggaacat tcctcacgaa aatccggttt ctttagccaa    720

aagcttaaat cacggaagct ctgtcaagca ccgcaatctg cttatggcag agaatgcgac    780

cgaattggaa gtggacatga tttggacgga aaaaggaagc gaaggcagac ttttaaagga    840

aacgttcatt ttcaagggag atgaatcatg aagaaaaaat ggccgttcat cgtcaacggt    900

ctttttttaa tgacttaggc agccgatcgt tcggccatac gatatcgaag cgacctcgaa    960

ccagcagagc tcgtcacaaa acatttgcat ttaaagaaaa atacaggatg ttttcaccaa   1020

tatttttctc aatgatgata cactattgac aagctgctac tttgggaggg tgtttccata   1080

gatgccgatg aagcaaaaac accaaatgtg tcatgagagc tctctctaat cgatataaaa   1140

gtagggtgaa ccggggttgt caatctgtaa aagatctttt tttatcccgt gatacgcttt   1200

tggaattctg aatcttcaag aaagtcccca gccttttgct gatcaatcga gaacaaagga   1260

tgatacatat gaaaagaata gataaaatct accatcagct gctggataat tttcgcgaaa   1320

agaatatcaa tcagctttta aagatacaag ggaattcggc taaagaaatc gccgggcagc   1380

tgcaaatgga gcgttccaat gtcagctttg aattaaacaa tctggttcgg gccaaaaagg   1440

tgatcaagat taaaacgttc cccgtccgct acatcccggt ggaaattgtt gaaaacgtct   1500

tgaacatcaa atggaattca gagttgatgg aggttgaaga actgaggcgg ctggctgacg   1560

gccaaaaaaa gccggcgcgc aatatatccg ccgatcccct cgagctcatg atcggggcta   1620

aagggagctt gaaaaaggca atttctcagg cgaaagcggc agtcttttat cctccgcacg   1680

gcttgcatat gctgctgctc gggccgacgg gttcggggaa atcgctgttt gcgaatcgga   1740

tctaccagtt cgccgtttat tctgacatat tgaagcccga ttccccgttc atcacattca   1800

actgtgcag                                                           1809
```

<210> SEQ ID NO 73
<211> LENGTH: 486
<212> TYPE: PRT
<213> ORGANISM: G. stearothermophilus

<400> SEQUENCE: 73

```
Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140
```

```
Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Pro Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr
                485
```

<210> SEQ ID NO 74
<211> LENGTH: 1967
<212> TYPE: DNA
<213> ORGANISM: Artificial Sequence
<220> FEATURE:
<223> OTHER INFORMATION: catH locus WT construct

<400> SEQUENCE: 74

```
tgtgtgacgg ctatcatgcc ggcgctttta taaacgagtt ggaacggctt gccgccgatt     60
```

```
gtgaggagtg gcttgtgtga cagaggaaag gccgatatga ttcggccttt tttatatgta    120

cttcttagcg ggtctcttaa ccccccctcga ggtcgctgat aaacagctga catcaatatc    180

ctatttttc aaaaaatatt ttaaaaagtt gttgacttaa aagaagctaa atgttatagt    240

aataaaacag aatagtcttt taagtaagtc tactctgaat ttttttaaaa ggagagggta    300

aagaatgaaa caacaaaaac ggctttacgc ccgattgctg acgctgttat ttgcgctcat    360

cttcttgctg cctcattctg cagctagcgc agccgcaccg tttaacggta ccatgatgca    420

gtattttgaa tggtacttgc cggatgatgg cacgttatgg accaaagtgg ccaatgaagc    480

caacaactta tccagccttg gcatcaccgc tctttggctg ccgcccgctt acaaaggaac    540

aagccgcagc gacgtagggt acggagtata cgacttgtat gacctcggcg aattcaatca    600

aaaagggacc gtccgcacaa aatatggaac aaaagctcaa tatcttcaag ccattcaagc    660

cgcccacgcc gctggaatgc aagtgtacgc cgatgtcgtg ttcgaccata aaggcggcgc    720

tgacggcacg gaatgggtgg acgccgtcga agtcaatccg tccgaccgca accaagaaat    780

ctcgggcacc tatcaaatcc aagcatggac gaaatttgat tttcccgggc ggggcaacac    840

ctactccagc tttaagtggc gctggtacca ttttgacggc gttgattggg acgaaagccg    900

aaaattaagc cgcatttaca aattcagggg catcggcaaa gcgtgggatt ggccggtaga    960

cacagaaaac ggaaactatg actacttaat gtatgccgac cttgatatgg atcatcccga   1020

agtcgtgacc gagctgaaaa actgggggaa atggtatgtc aacacaacga acattgatgg   1080

gttccggctt gatgccgtca agcatattaa gttcagtttt tttcctgatt ggttgtcgta   1140

tgtgcgttct cagactggca agccgctatt taccgtcggg gaatattgga gctatgacat   1200

caacaagttg cacaattaca ttacgaaaac aaacggaacg atgtctttgt ttgatgcccc   1260

gttacacaac aaattttata ccgcttccaa atcagggggc gcatttgata tgcgcacgtt   1320

aatgaccaat actctcatga aagatcaacc gacattggcc gtcaccttcg ttgataatca   1380

tgacaccgaa cccggccaag cgcttcagtc atgggtcgac ccatggttca aaccgttggc   1440

ttacgccttt attctaactc ggcaggaagg atacccgtgc gtcttttatg gtgactatta   1500

tggcattcca caatataaca ttccttcgct gaaaagcaaa atcgatccgc tcctcatcgc   1560

gcgcagggat tatgcttacg gaacgcaaca tgattatctt gatcactccg acatcatcgg   1620

gtggacaagg gaaggggtca ctgaaaaacc aggatccggg ctggccgcac tgatcaccga   1680

tgggccggga ggaagcaaat ggatgtacgt tggcaaacaa cacgctggaa aagtgttcta   1740

tgaccttacc ggcaaccgga gtgacaccgt caccatcaac agtgatggat ggggggaatt   1800

caaagtcaat ggcggttcgg tttcggtttg ggttcctaga aaaacgacct aaaagcttct   1860

cgaggttaac agaggacgga tttcctgaag gaaatccgtt tttttatttt taacatctct   1920

cactgctgtg tgattttact cacggcattt ggaacgccgg ctctcaa                 1967
```

<210> SEQ ID NO 75
<211> LENGTH: 1966
<212> TYPE: DNA
<213> ORGANISM: Artificial Sequence
<220> FEATURE:
<223> OTHER INFORMATION: catH locus mod 5'-UTR construct

<400> SEQUENCE: 75

```
tgtgtgacgg ctatcatgcc ggcgctttta taaacgagtt ggaacggctt gccgccgatt     60

gtgaggagtg gcttgtgtga cagaggaaag gccgatatga ttcggccttt tttatatgta    120

cttcttagcg ggtctcttaa ccccccctcga ggtcgctgat aaacagctga catcaatatc    180
```

```
ctatttttc aaaaaatatt ttaaaaagtt gttgacttaa aagaagctaa atgttatagt    240

aataaaacag aatagtcttt taagtaagtc tactctgaat ttttttaaaa ggagagggta    300

aagatgaaac aacaaaaacg gctttacgcc cgattgctga cgctgttatt tgcgctcatc    360

ttcttgctgc ctcattctgc agctagcgca gccgcaccgt ttaacggtac catgatgcag    420

tattttgaat ggtacttgcc ggatgatggc acgttatgga ccaaagtggc caatgaagcc    480

aacaacttat ccagccttgg catcaccgct ctttggctgc cgcccgctta caaaggaaca    540

agccgcagcg acgtagggta cggagtatac gacttgtatg acctcggcga attcaatcaa    600

aaagggaccg tccgcacaaa atatggaaca aaagctcaat atcttcaagc cattcaagcc    660

gcccacgccg ctggaatgca agtgtacgcc gatgtcgtgt tcgaccataa aggcggcgct    720

gacggcacgg aatgggtgga cgccgtcgaa gtcaatccgt ccgaccgcaa ccaagaaatc    780

tcgggcacct atcaaatcca agcatggacg aaatttgatt ttcccgggcg gggcaacacc    840

tactccagct ttaagtggcg ctggtaccat tttgacggcg ttgattggga cgaaagccga    900

aaattaagcc gcatttacaa attcaggggc atcggcaaag cgtgggattg gccggtagac    960

acagaaaacg gaaactatga ctacttaatg tatgccgacc ttgatatgga tcatcccgaa   1020

gtcgtgaccg agctgaaaaa ctgggggaaa tggtatgtca acacaacgaa cattgatggg   1080

ttccggcttg atgccgtcaa gcatattaag ttcagttttt ttcctgattg gttgtcgtat   1140

gtgcgttctc agactggcaa gccgctattt accgtcgggg aatattggag ctatgacatc   1200

aacaagttgc acaattacat tacgaaaaca aacggaacga tgtctttgtt tgatgccccg   1260

ttacacaaca aattttatac cgcttccaaa tcagggggcg catttgatat gcgcacgtta   1320

atgaccaata ctctcatgaa agatcaaccg acattggccg tcaccttcgt tgataatcat   1380

gacaccgaac ccggccaagc gcttcagtca tgggtcgacc catggttcaa accgttggct   1440

tacgccttta ttctaactcg gcaggaagga tacccgtgcg tcttttatgg tgactattat   1500

ggcattccac aatataacat tccttcgctg aaaagcaaaa tcgatccgct cctcatcgcg   1560

cgcagggatt atgcttacgg aacgcaacat gattatcttg atcactccga catcatcggg   1620

tggacaaggg aaggggtcac tgaaaaacca ggatccgggc tggccgcact gatcaccgat   1680

gggccgggag gaagcaaatg gatgtacgtt ggcaaacaac acgctggaaa agtgttctat   1740

gaccttaccg gcaaccggag tgacaccgtc accatcaaca gtgatggatg gggggaattc   1800

aaagtcaatg gcggttcggt ttcggtttgg gttcctagaa aaacgaccta aaagcttctc   1860

gaggttaaca gaggacggat ttcctgaagg aaatccgttt ttttattttt aacatctctc   1920

actgctgtgt gattttactc acggcatttg gaacgccggc tctcaa                  1966
```

<210> SEQ ID NO 76
<211> LENGTH: 20
<212> TYPE: DNA
<213> ORGANISM: Artificial Sequence
<220> FEATURE:
<223> OTHER INFORMATION: catH locus forward primer

<400> SEQUENCE: 76

```
tgtgtgacgg ctatcatgcc                                                 20
```

<210> SEQ ID NO 77
<211> LENGTH: 17
<212> TYPE: DNA
<213> ORGANISM: Artificial Sequence
<220> FEATURE:

<223> OTHER INFORMATION: catH locus reverse primer

<400> SEQUENCE: 77
ttgagagccg gcgttcc 17

<210> SEQ ID NO 78
<211> LENGTH: 20
<212> TYPE: DNA
<213> ORGANISM: Artificial Sequence
<220> FEATURE:
<223> OTHER INFORMATION: catH forward sequencing primer 1

<400> SEQUENCE: 78
aacgagttgg aacggcttgc 20

<210> SEQ ID NO 79
<211> LENGTH: 20
<212> TYPE: DNA
<213> ORGANISM: Artificial Sequence
<220> FEATURE:
<223> OTHER INFORMATION: catH forward sequencing primer 2

<400> SEQUENCE: 79
ggcaacacct actccagctt 20

<210> SEQ ID NO 80
<211> LENGTH: 20
<212> TYPE: DNA
<213> ORGANISM: Artificial Sequence
<220> FEATURE:
<223> OTHER INFORMATION: catH forward sequencing primer 3

<400> SEQUENCE: 80
gatcactccg acatcatcgg 20

<210> SEQ ID NO 81
<211> LENGTH: 1205
<212> TYPE: DNA
<213> ORGANISM: Bacillus licheniformis

<400> SEQUENCE: 81
catcaatctt tttccagaca gtgatcaaaa ttcgacattt ttcatcaaaa acgtcaaaat 60
aaattgacgc gctttcatga gttttgtacg atatgagaga ttgatgacaa aaaggagctg 120
aggatcgtga acagatcctt taccgttgaa aaggtactca acaacaacgt tttaatcgct 180
ctccatgatg attacagaga agttgtcttg attggcaaag gaatcggttt tggtaaaaag 240
cgcggagatc ttatcgaaca tgagaactac gaaaaaatgt ttatcctgga aaatgataag 300
gaacaatcgc agtataagaa gctcctcact tatgtcgatg aaaaaatggt tgatatcgcc 360
aatgatgtca tctaccatat cgcgcaaaaa atcggccagc cgctgaacga acacattcat 420
gtcgccctga cggaccatat cgcatttgca gttaagcgtc tagaaaaggg atttgatatg 480
aaaaatccgt tttgcttgga gacggaatcg ctttatccga aggaatacga agtcgccaag 540
gaagccgtcg atatgattaa tgaaaaatcc gacattcagc tgcctgaagg tgaaatcggg 600
ttcatcgcgc ttcatatcca cagtgcgatg acaaaccgcc cgctttctga agtcaatcag 660
cattcacaac tgatctccag gcttgtccag gtcatcgaag attcattcca gatgcaagtc 720
aacagggaaa gcgtgaacta tttgcggctg atcaggcact tgcgctttac gattgacagg 780
ataaaacggg acgagccgat tcaggaaccg gaaaaattaa tgttgttgtt gaaaacggaa 840
tatccgctgt gttacaatac tgcttggaag atgatcaaga tcttgcagca agcgctcaag 900

```
aaaccggttc atgaggcaga agccgtttat ttgacattgc atttgtaccg tttgactaat    960

aaaatttcat aacgccttta taacgtgtta ctgattcgat caggcatgag tgaaaaaagg   1020

ggagaaatga agacgctgtc ttttgtttct tagtgtaccc gctttcacca tgccttttttt   1080

gtcgttctaa aggcgaaatg taaacggttt atttagatga aaaagcagtc ttttgaacga   1140

agttgtcatg aatttttgct gtaaggtcaa actattctta gagggggtta aaaaatgttt   1200

aaatc                                                                1205
```

<210> SEQ ID NO 82
<211> LENGTH: 281
<212> TYPE: PRT
<213> ORGANISM: Bacillus licheniformis

<400> SEQUENCE: 82

```
Val Asn Arg Ser Phe Thr Val Glu Lys Val Leu Asn Asn Asn Val Leu
1               5                   10                  15

Ile Ala Leu His Asp Asp Tyr Arg Glu Val Val Leu Ile Gly Lys Gly
            20                  25                  30

Ile Gly Phe Gly Lys Lys Arg Gly Asp Leu Ile Glu His Glu Asn Tyr
        35                  40                  45

Glu Lys Met Phe Ile Leu Glu Asn Asp Lys Glu Gln Ser Gln Tyr Lys
    50                  55                  60

Lys Leu Leu Thr Tyr Val Asp Glu Lys Met Val Asp Ile Ala Asn Asp
65                  70                  75                  80

Val Ile Tyr His Ile Ala Gln Lys Ile Gly Gln Pro Leu Asn Glu His
                85                  90                  95

Ile His Val Ala Leu Thr Asp His Ile Ala Phe Ala Val Lys Arg Leu
            100                 105                 110

Glu Lys Gly Phe Asp Met Lys Asn Pro Phe Leu Leu Glu Thr Glu Ser
        115                 120                 125

Leu Tyr Pro Lys Glu Tyr Glu Val Ala Lys Glu Ala Val Asp Met Ile
    130                 135                 140

Asn Glu Lys Ser Asp Ile Gln Leu Pro Glu Gly Glu Ile Gly Phe Ile
145                 150                 155                 160

Ala Leu His Ile His Ser Ala Met Thr Asn Arg Pro Leu Ser Glu Val
                165                 170                 175

Asn Gln His Ser Gln Leu Ile Ser Arg Leu Val Gln Val Ile Glu Asp
            180                 185                 190

Ser Phe Gln Met Gln Val Asn Arg Glu Ser Val Asn Tyr Leu Arg Leu
        195                 200                 205

Ile Arg His Leu Arg Phe Thr Ile Asp Arg Ile Lys Arg Asp Glu Pro
    210                 215                 220

Ile Gln Glu Pro Glu Lys Leu Met Leu Leu Leu Lys Thr Glu Tyr Pro
225                 230                 235                 240

Leu Cys Tyr Asn Thr Ala Trp Lys Met Ile Lys Ile Leu Gln Gln Ala
                245                 250                 255

Leu Lys Lys Pro Val His Glu Ala Glu Ala Val Tyr Leu Thr Leu His
            260                 265                 270

Leu Tyr Arg Leu Thr Asn Lys Ile Ser
        275                 280
```

<210> SEQ ID NO 83
<211> LENGTH: 140
<212> TYPE: PRT

```
<213> ORGANISM: Bacillus licheniformis

<400> SEQUENCE: 83

Met Ala Met Thr Arg Phe Gly Glu Arg Leu Lys Glu Leu Arg Glu Gln
1               5                   10                  15

Arg Ser Leu Ser Val Asn Gln Leu Ala Met Tyr Ala Gly Val Ser Ala
            20                  25                  30

Ala Ala Ile Ser Arg Ala Ala Ala Ile Ser Arg Ile Glu Asn Gly His
        35                  40                  45

Arg Gly Val Pro Lys Pro Ala Thr Ile Arg Lys Leu Ala Glu Ala Leu
    50                  55                  60

Lys Met Pro Tyr Glu Gln Leu Met Asp Ile Ala Gly Tyr Met Arg Ala
65                  70                  75                  80

Asp Glu Ile Arg Glu Gln Pro Arg Gly Tyr Val Thr Met Gln Glu Ile
                85                  90                  95

Ala Ala Lys His Gly Val Glu Asp Leu Trp Leu Phe Lys Pro Glu Lys
            100                 105                 110

Trp Asp Cys Leu Ser Arg Glu Asp Leu Leu Asn Leu Glu Gln Tyr Phe
        115                 120                 125

His Phe Leu Val Asn Glu Ala Lys Lys Arg Gln Ser
    130                 135                 140


<210> SEQ ID NO 84
<211> LENGTH: 134
<212> TYPE: PRT
<213> ORGANISM: Bacillus licheniformis

<400> SEQUENCE: 84

Met Ala Met Thr Arg Phe Gly Glu Arg Leu Lys Glu Leu Arg Glu Gln
1               5                   10                  15

Arg Ser Leu Ser Val Asn Gln Leu Ala Met Tyr Ala Gly Val Ser Ala
            20                  25                  30

Ala Ala Ile Ser Arg Ile Glu Asn Gly His Arg Gly Val Pro Lys Pro
        35                  40                  45

Ala Thr Ile Arg Lys Leu Ala Glu Ala Leu Lys Met Pro Tyr Glu Gln
    50                  55                  60

Leu Met Asp Ile Ala Gly Tyr Met Arg Ala Asp Glu Ile Arg Glu Gln
65                  70                  75                  80

Pro Arg Gly Tyr Val Thr Met Gln Glu Ile Ala Ala Lys His Gly Val
                85                  90                  95

Glu Asp Leu Trp Leu Phe Lys Pro Glu Lys Trp Asp Cys Leu Ser Arg
            100                 105                 110

Glu Asp Leu Leu Asn Leu Glu Gln Tyr Phe His Phe Leu Val Asn Glu
        115                 120                 125

Ala Lys Lys Arg Gln Ser
    130
```